(12) United States Patent
Li

(10) Patent No.: US 10,654,906 B2
(45) Date of Patent: May 19, 2020

(54) HIGH-STABILITY T-CELL RECEPTOR AND PREPARATION METHOD AND APPLICATION THEREOF

(71) Applicant: Guangdong Xiangxue Life Sciences, Ltd., Luogang District, Guangzhou (CN)

(72) Inventor: Yi Li, Guangzhou (CN)

(73) Assignee: Guangdong Xiangxue Life Sciences, Ltd., Luogang District, Guangzhou (CN)

( * ) Notice: Subject to any disclaimer, the term of this patent is extended or adjusted under 35 U.S.C. 154(b) by 233 days.

(21) Appl. No.: 14/901,344

(22) PCT Filed: Jun. 25, 2014

(86) PCT No.: PCT/CN2014/080773
§ 371 (c)(1),
(2) Date: Dec. 28, 2015

(87) PCT Pub. No.: WO2014/206304
PCT Pub. Date: Dec. 31, 2014

(65) Prior Publication Data
US 2016/0130319 A1 May 12, 2016

(30) Foreign Application Priority Data
Jun. 26, 2013 (CN) .......................... 2013 1 0263384

(51) Int. Cl.
| C07K 1/00 | (2006.01) |
| C07K 14/725 | (2006.01) |
| A61K 47/64 | (2017.01) |
| A61K 38/17 | (2006.01) |
| A61K 49/00 | (2006.01) |
| C07K 16/28 | (2006.01) |
| A61K 38/00 | (2006.01) |

(52) U.S. Cl.
CPC ...... *C07K 14/7051* (2013.01); *A61K 38/1774* (2013.01); *A61K 47/6425* (2017.08); *A61K 49/00* (2013.01); *C07K 16/2809* (2013.01); *A61K 38/00* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| 2012/0027739 A1 | 2/2012 | Jakobsen et al. |
| 2012/0225481 A1 | 9/2012 | Jakobsen et al. |

FOREIGN PATENT DOCUMENTS

| CN | 102574906 A | 7/2012 |
| CN | 103097407 A | 5/2013 |
| WO | 2005/113595 A2 | 12/2005 |
| WO | 2005/116075 A1 | 12/2005 |
| WO | 2006/037960 A2 | 4/2006 |
| WO | 2007/106894 A2 | 9/2007 |
| WO | 2012/013913 A1 | 2/2012 |
| WO | 2013/041865 A1 | 3/2013 |
| WO | 2013/067517 A2 | 5/2013 |
| WO | 2014/206304 A1 | 12/2014 |

OTHER PUBLICATIONS

Hare et al., 1999, Nat. Struct. Biol. vol. 6: 574-581.*
Aggen et al., 2010, Prote. Engineering Design and Selection, vol. 24: 361-372.*
IMGT scientific chart, 2018, pp. 1-2.*
Kieke et al., 1999, PNAS, vol. 96: 5651-5656.*
Brawley et al., 2002, J.Immunol. vol. 168: 38943901.*
Robbins et al., 2008, J. Immunol. vol. 180: 6116-6131.*
International Search Report (and English translation) dated Jun. 25, 2014 in PCT/CN2014/080773; 10 pages.
Boulter, J.M. et al.; "Stable, soluble T-cell receptor molecules for crystallization and therapeutics"; *Protein Engineering*; vol. 19, No. 9; 2003; pp. 707-711.
Kieke, M.C. et al.; "Selection of functional T cell receptor mutants from a yeast surface-display library"; *Proc. Natl. Acad. Sci. USA*; vol. 96, May 1999; pp. 5651-5656.
Lefranc, M.-P.; "Immunoglobulin and T cell receptor genes: IMGT and the birth and rise of immunoinformatics"; *Frontiers in Immunology*; vol. 5, Article 22; Feb. 5, 2014; 22 pages.
Li, Y. et al.; "Directed evolution of human T-cell receptors with picomolar affinities by phage display"; *Nature Biotechnology*; vol. 23, No. 3; Mar. 2005; pp. 349-354.
Liddy, N. et al.; "Monoclonal TCR-redirected tumor cell killing"; *Nature Medicine*; May 6, 2012; 9 pages.
Richman, S.A. et al.; "Structural features of T cell receptor variable regions that enhance domain stability and enable expression as single-chain VαVβ fragments"; *Molecular Immunology*; vol. 46; 2009; pp. 902-916.
Shusta, E.V. et al.; "Directed evolution of a stable scaffold for T-cell receptor engineering"; *Nature Biotechnology*; vol. 18; Jul. 2000; pp. 754-759.

\* cited by examiner

*Primary Examiner* — Amy E Juedes
(74) *Attorney, Agent, or Firm* — Kilpatrick Townsend & Stockton LLP

(57) ABSTRACT

The present invention provides a high-stability T cell receptor. The T cell receptor has mutations in its hydrophobic core domain causing the enhancement of stability thereof. The present invention additionally provides a preparation method and an application of the T-cell receptor.

11 Claims, 20 Drawing Sheets
Specification includes a Sequence Listing.

KQEVTQSPSS LSVPEGENLV LNCSFTDSAI YNLQWFRQDP GKGLTSLLLV RPYQREQTSG 60
RLNASLDKSS GRSTLYIESS QPGDSATYLC AVRPGGAGSY QLTFGKGTKL SVTP 114
(SEQ ID NO: 9)

Figure 2a

```
aaacaggagg tgacgcagtc tccttcatct ctgagtgtcc cagaaggaga aaacttgtct  60
ctcaactgca gtttcactga tagcgctatt tacaacctcc agtggtttag gcaggaccct 120
gggaaaggtc tcacatctct gttgttagtg cgtccgtatc agagagagca aacaagtgga 180
agacttaatg cctcgctgga taaatcatca ggacgtagta ctttatacat tgaatcttct 240
cagcccgggg actcagccac ctacctctgt gctgtgaggc cggaggggc tgggagttac 300
caactcactt cgggaaggg gaccaaactc tcggtcactc ca 342
```
(SEQ ID NO: 10)

Figure 2b

KAGVTQTPRY LSKTRGQQVT LSCSPISGHR SVSWYQQTPG QGLQFLFEYF SETQRNKGNF 60
PGRFSGRQFS NSRSEMNVST LELGDSALYL CASSPNMADE QYFGPGTRLT VT 112
(SEQ ID NO: 11)

Figure 3a

```
aaggctggag tcactcaaac tccaagatat ctgtccaaaa cgagaggaca gcaagtgaca  60
ctgagctgct cccctatctc tgggcatagg agtgtatcct ggtaccaaca gacccagga 120
cagggccttc agttcctctt tgaatacttc agtgagacac agagaaacaa aggaaacttc 180
cctggtcgat tctcagggcg ccagttctct aactctcgct ctgagatgaa tgtgagcacc 240
ttggagctgg gggactcggc cctttatctt tgcgccagca gcccgaacat ggccgacgag 300
cagtacttcg gcccgggcac caggctcacg gtcaca 336
```
(SEQ ID NO: 12)

Figure 3b

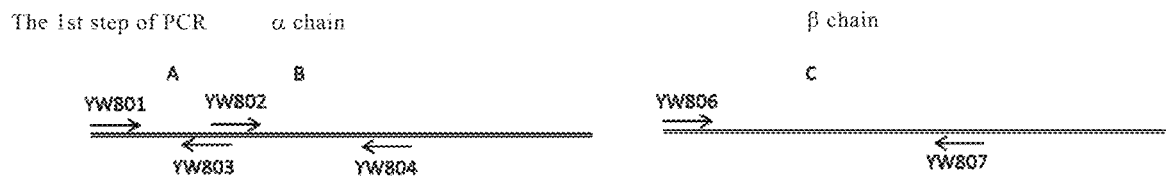

Figure 4

GPGGSGGGGE GGGGSGGGGE GGSGG                                                25
(SEQ ID NO: 13)

<p align="center">Figure 5a</p> gggcccggtg gatctggcgg tggcggtgaa ggcggtggtg gaagcggcgg cggaggcgaa      60
ggaggctccg gaggc                                                         75
(SEQ ID NO: 14)

<p align="center">Figure 5b</p>

KQEVTQSPSS LSVPEGENVS INCSFTDSAI YNLQWFRQDP GKGLTSLLLV RPYQREQTSG       60
RLNASLDKSS GRSTLYLESS QPGDSATYLC AVRPGGAGSY QLTFGKGTKL SVTP            114
(SEQ ID NO: 15)

<p align="center">Figure 6a</p>

KAGVTQTPRY LSKTRGQQVT LSCSPISGHR SVSWYQQTPG QGLQFLFEYF SETQRNKGNF       60
PGRFSGRQFS NSRSEMNFST LELGDSALYL CASSPNMADE QYFGPGTRMT VT              112
(SEQ ID NO: 16)

<p align="center">Figure 6b</p>

KQEVTQSPSS LSVPEGENVS INCSFTDSAI YNLQWFRQDP GKGLTSLLLV RPYQREQTSG       60
RLNASLDKSS GRSTLYIESS QPGDSATYLC AVRPGGAGSY QLTFGKGTKL SVTP            114
(SEQ ID NO: 17)

<p align="center">Figure 7a</p>

KAGVTQTPRY LSKTRGQQVT LSCSPISGHR SVSWYQQTPG QGLQFLFEYF SETQRNKGNF       60
PGRFSGRQFS NSRSEMNIST LELGDSALYL CASSPNMADE QYFGPGTRLT VT              112
(SEQ ID NO: 18)

<p align="center">Figure 7b</p>

KQEVTQSPSS LSVPEGENVS INCSFTDSAI YNLQWFRQDP GKGLTSLLLV RPYQREQTSG       60
RLNASLDKSS GRSTLYLESS QPGDSATYLC AVRPGGAGSY QLTFGKGTKL SVTP            114
(SEQ ID NO: 15)

<p align="center">Figure 8a</p>

KAGVTQTPRY LSKTRGQQVT LSCSPISGHR SVSWYQQTPG QGLQFLFEYF SETQRNKGNF       60
PGRFSGRQFS NSRSEMNIST LELGDSALYL CASSPNMADE QYFGPGTRLT VT              112
(SEQ ID NO: 18)

<p align="center">Figure 8b</p>

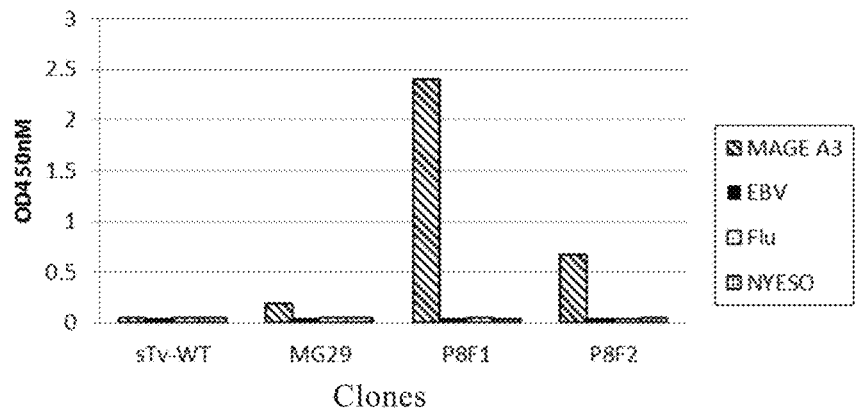

Figure 9

DAKTTQPNSMESNEEEPVHLPCNHSTISGTDYIHWYRQLPSQGPEYVIHGLTSNVNNRMASLAIAEDRKSSTLIL
HRATLRDAAVYYCILRDAGGTSYGKLTFGQGTILTVHP (SEQ ID NO: 29)

Figure 10a

GAGVSQSPRYKVAKRGQDVALRCDPISGHVSLFWYQQALGQGPEFLTYFQNEAQLDKSGLPSDRFFAERPEGSVS
TLKIQRTQQEDSAVYLCASSLGQSYEQYFGPGTRLTVT (SEQ ID NO: 30)

Figure 10b

TQLLEQSPQFLSIQEGENLTVYCNSSSVFSSLQWYRQEPGEGPVLLVTVVTGGEVKKLKRLTFQFGDARKDSSLH
ITAAQPGDTGLYLCAGGGSQGNLIFGKGTKLSVKP (SEQ ID NO: 31)

Figure 11a

DGGITQSPKYLFRKEGQNVTLSCEQNLNHDAMYWYRQDPGQGLRLIYYSQIVNDFQKGDIAEGYSVSREKKESFPLTVT
SAQKNPTAFYLCASSIRSSYEQYFGPGTRLTVT (SEQ ID NO: 32)

Figure 11b

KQEVTQIPAALSVPEGENLVLNCSFTDSAIYNLQWFRQDPGKGLTSLLLIQSSQREQTSGRLNASLDKSSGRSTLYIAA
SQPGDSATYLCAVRPASGGSYIPTFGRGTSLIVHP (SEQ ID NO: 33)

Figure 12a

NAGVTQTPKFQVLKTGQSMTLQCAQDMNHEYMSWYRQDPGMGLRLIHYSVGAGITDQGEVPNGYNVSRSTTEDFPLRLL
SAAPSQTSVYFCASSYVGNTGELFFGEGSRLTVL (SEQ ID NO: 34)

Figure 12b

DAKTTQPNSLEVNEEEPVHIPCNHSTISGTDYIHWYRQLPSQGPEYVIHGLTSNVNNRMASLAIAEDRKSSTLYI
HRATPRDSATYFCAVPLAGGTSYGKLTFGKGTKLSVTP(SEQ ID NO: 35)

Figure 13a

GAGVSQSPRYKSAKRGQDVTLRCDPISGHVSLFWYQQAPGQGPEFLTYFQNEAQLDKSGLPSDRFSAERPEGSVS
TLKIQRLQPEDSAVYLCASSLGQAYEQYFGPGTRLTVT(SEQ ID NO: 36)

Figure 13b

TQLLEQSPQSLSIQEGENVTIYCNSSSVFSSLQWYRQEPGEGPTLLVTVVTGGEVKKLKRLTFQFGDARKDSSLH
ITSAQPGDSGTYFCAVAGSQGNLIFGKGTKLSVTP(SEQ ID NO: 37)

Figure 14a

DGGITQSPKYLSRKEGQNVTLSCEQNLNHDAMYWYRQDPGQGLRLIYYSQIVNDFQKGDIAEGYSVSREKKESFP
LTITSLQKNDSAVYLCASSSRSSYEQYFGPGTRLTVT(SEQ ID NO: 38)

Figure 14b

KQEVTQSPSSLSVPEGENVSINCSFTDSAIYNLQWFRQDPGKGLTSLLLIQSSQREQTSGRLNASLDKSS
GRSTLYIESSQPGDSATYFCAVRPTSGGSYIPTFGKGTKLSVTP(SEQ ID NO: 39)

Figure 15a

NAGVTQTPKYQSLKTGQSVTLQCAQDMNHEYMSWYRQDPGQGLRLIHYSVGAGITDQGEVPNGYNVSRSTT
EDFPLRIESLTPSDSAVYLCASSYVGNTGELFFGPGTRLTVT(SEQ ID NO: 40)

Figure 15b

GGGSEGGGSEGGGSEGGGSEGGTG(SEQ ID NO: 41)

Figure 16

KQEVTQSPSSLSVPEGENVSINCSFTDSAIYNLQWFRQDPGKGLTSLLLIQSSQREQTSGRLNASLDKSSGRSTL
YIESSQPGDSATYFCAVRPTSGGSYIPTFGKGTKLSVTPGGGSEGGGSEGGGSEGGGSEGGTGNAGVTQTPKYQS
LKTGQSVTLQCAQDMNHEYMSWYRQDPGQGLRLIHYSVGAGITDQGEVPNGYNVSRSTTEDFPLRIESLTPSDSA
VYLCASSYVGNTGELFFGPGTRLTVT (SEQ ID NO: 42)

KQELTQSPSSLNRPESENVSINCSFTDSAIYNLQWFRQDPGKGLTSLLLIQSSQREQTSGRLNASLDKSSGRSTLYIENVQPNDSGTYFCSVRPTSGGSYIPTFGKGTKLSVTN(SEQ ID NO: 75)

KQEVTQSPSSMNVPESENVSINCSFTDSAIYNLQWFRQDPGKGLTSLLLIQSSQREQTSGRLNASLDKSSGRSTLYIENVQPNDSGTYFCAVRPTSGGSYIPTFGKGTKLSVTN(SEQ ID NO: 76)

KQELTQSPSSENVPESENVSINCSFTDSAIYNLQWFRQDPGKGLTSLLLIQSSQREQTSGRLNASLDKSSGRSTLYIENVQPNDSGTYFCSVRPTSGGSYIPTFGKGTKLSVTN(SEQ ID NO: 77)

KQELTQSPSSLNVPESENVSINCSFTDSAIYNLQWFRQDPGKGLTSLLLIQSSQREQTSGRLNASLDKSSGRSTLYIENVQPNDSGTYFCSVRPTSGGSYIPTFGKGTKLSVTN(SEQ ID NO: 78)

KQEVTQSPSSLNKPESENVSINCSFTDSAIYNLQWFRQDPGKGLTSLLLIQSSQREQTSGRLNASLDKSSGRSTLYIENVQPNDSGTYFCSVRPTSGGSYIPTFGKGTKLSVTN(SEQ ID NO: 79)

KQEVTQSPSSMSVPESENVSINCSFTDSAIYNLQWFRQDPGKGLTSLLLIQSSQREQTSGRLNASLDKSSGRSTLYIERIQPNDSGTYFCAVRPTSGGSYIPTFGKGTKLSVTN(SEQ ID NO: 80)

KQEVTQSPSSESVPESENVSINCSFTDSAIYNLQWFRQDPGKGLTSLLLIQSSQREQTSGRLNASLDKSSGRSTLYIERIQPNDSGTYFCAVRPTSGGSYIPTFGKGTKLSVTN(SEQ ID NO: 81)

KQEVTQSPSSLSVPESENVSINCSFTDSAIYNLQWFRQDPGKGLTSLLLIQSSQREQTSGRLNASLDKSSGRSTLYIERIQPNDSGTYFCAVRPTSGGSYIPTFGKGTKLSVTN(SEQ ID NO: 82)

KQEVTQSPSSLSKPESENVSINCSFTDSAIYNLQWFRQDPGKGLTSLLLIQSSQREQTSGRLNASLDKSSGRSTLYIERIQPNDSGTYFCAVRPTSGGSYIPTFGKGTKLSVTN(SEQ ID NO: 83)

KQEVTQSPSSLNVPESENVSINCSFTDSAIYNLQWFRQDPGKGLTSLLLIQSSQREQTSGRLNASLDKSSGRSTLYIENVQPNDSGTYFCSVRPTSGGSYIPTFGKGTKLSVTN(SEQ ID NO: 84)

KQEVTQSPSSLSVPESENVSINCSFTDSAIYNLQWFRQDPGKGLTSLLLIQSSQREQTSGRLNASLDKSSGRSTLYIERIQPNDSGTYFCAVRPTSGGSYIPTFGKGTKLSVTN(SEQ ID NO: 85)

Figure 25

NAGITQTPKYLSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 86)

NAGITQTPKYLSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 87)

NAGVTQTPKYLSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 88)

NAGVTQTPKYLSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 89)

NAGITQTPKYLSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 90)

NAGITQTPKYVSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 91)

NAGVTQTPKYVSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 92)

NAGVTQTPKYVSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 93)

NAGITQTPKYVSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 94)

NAGITQTPKYLSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 95)

NAGITQTPKYVSVKTGQSVTLQCAQDMNHEYMSWYRQDPGQGLRLIHYSVGAGITDQGEVPNGYNVSRSTTEDFPLRIESVTPSDSALYLCASSYVGNTGELFFGPGTRLEVD(SEQ ID NO: 96)

Figure 26

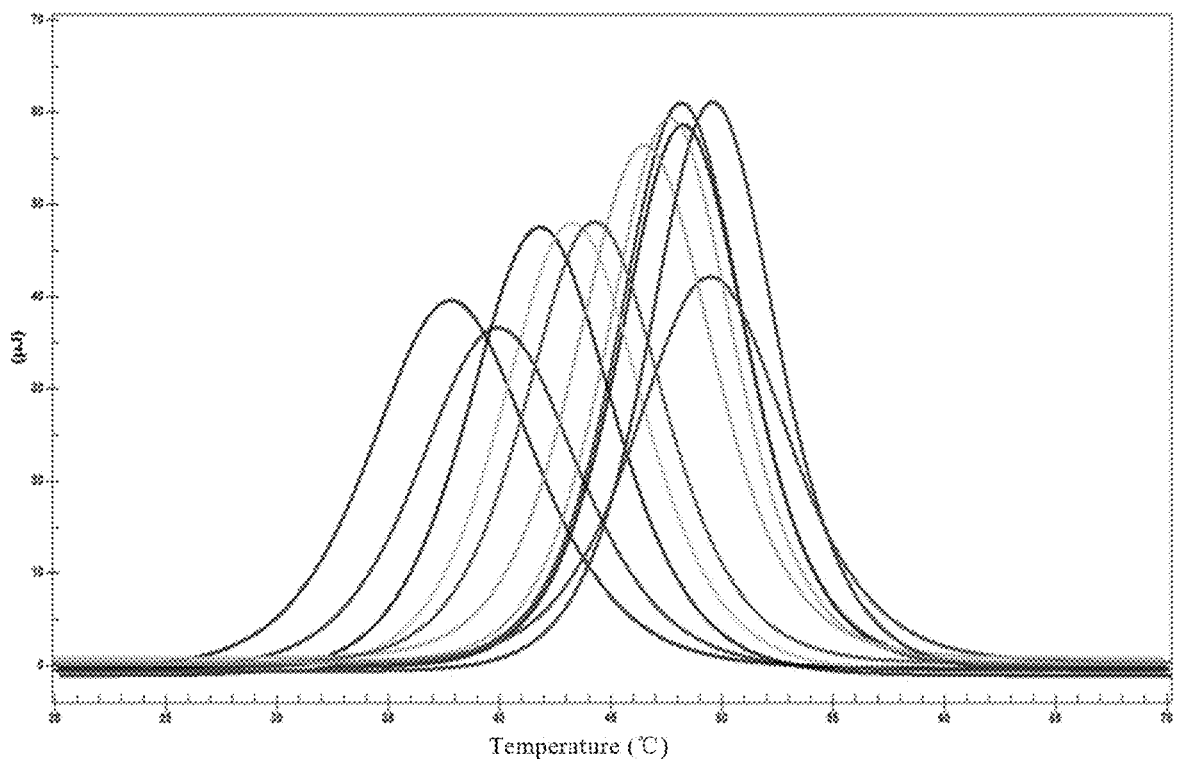
Figure 27
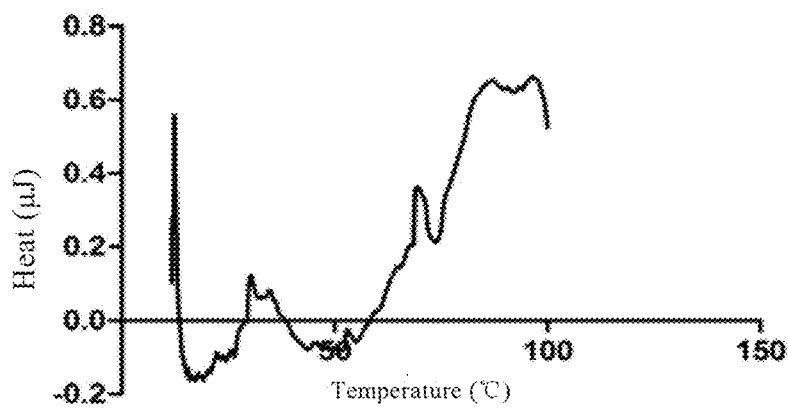
Figure 28
KQEVTQSPSSLNVPESENVSINCSFTDSAIYNLQWFRQDPGKGLTSLLLIQSSQRE
QTSGRLNASLDKSSGRSTLYIERIQPNDSGTYFCAVRPTSGGSYIPTFGKGTKLS
VTN(SEQ ID NO: 97)
Figure 29a
NAGITQTPKYLSVKTGQSVTLQCAQDMNHEYMSWYRQDPGQGLRLIHYSVGA
GITDQGEVPNRYNVSRSTTEDFPLRIESVTPSDSAVYLCASSYVGNTGELFFGPG
TRLEVD(SEQ ID NO: 98)
Figure 29b

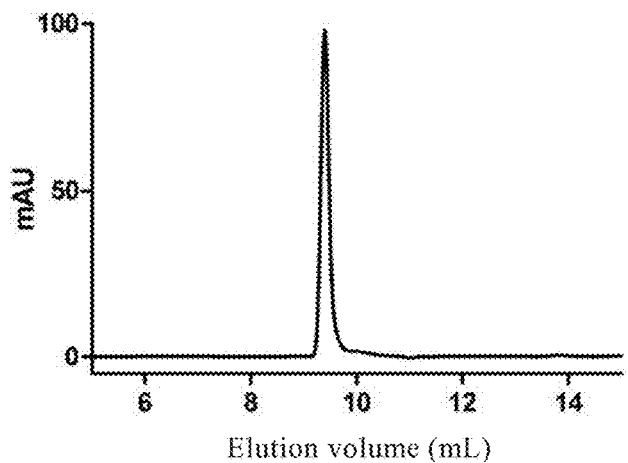

Figure 31c

DAKTTQPNSMS_V_NEEEPVS_I_PCNHSTISGTDYIHWYRQLPSQGPEYVIHGLTSNV
NNRRASLAIAEDRKSSTLY_I_HR_I_TPNDSGTYFCAVPLAGGTSYGKLTFGKGTKLS
VTN (SEQ ID NO: 99)

Figure 32a

GAGISQSPRY_V_S_V_KRGQDVTLRCDPISGHVSLFWYQQAPGQGPEFLTYFQNEAQ
LDKSGLPSDRFSAERPEGSVSTLKIQS_V_TPSDSALYLCASSLGQAYEQYFGPGTR
LEVD (SEQ ID NO: 100)

Figure 32b

DAKVTQPNS_L_N_V_NEEEPVS_I_PCNHSTISGTDYIHWYRQLPSQGPEYVIHGLTSNV
NNGRLSLAIAEDRKSSTLY_I_ER_I_TPNDSGTYFCAVPLAGGTSYGKLTFGKGTKLS
VTN (SEQ ID NO: 101)

Figure 33a

GAGISQSPRY_L_S_V_KTGQDVTLRCDPISGHVSLFWYQQAPGQGPEFLTYFQNEAQ
LDKSGLPSDRFSAERPEGSVSTLKIQS_V_TPSDSAVYLCASSLGQAYEQYFGPGTR
LEVD (SEQ ID NO: 102)

Figure 33b

TQLLEQSPQS_M_S_V_QESEN_V_T_I_YCNSSSVFSSLQWYRQEPGEGPTLLVTVVTGGE
VKKLKRLTFQFGDARKDSSLHIT_R_I_QPNDSGTYFCAVAGSQGNLIFGKGTKLSV
TN (SEQ ID NO: 103)

Figure 34a

DGGITQSPKY_V_S_V_KEGQNVTLSCEQNLNHDAMYWYRQDPGQGLRLIYYSQIVN
DFQKGDIAEGYSVSREKKESFPLT_I_TS_V_TKSDSALYLCASSSRSSYEQYFGPGTR
LEVD (SEQ ID NO: 104)

Figure 34b

TQLVEQSPQSLN_V_QESEN_V_T_I_YCNSSSVFSSLQWYRQEPGEGPTLLVTVVTGGE
VKKLKRLTFQFGDARKDSSLHIER_I_QPNDSGTYFCAVAGSQGNLIFGKGTKLSV
TN (SEQ ID NO: 105)

Figure 35a

DGGITQSPKYLSVKTGQSVTLSCEQNLNHDAMYWYRQDPGQGLRLIYYSQIVN
DFQKGDIAERYSVSREKKESFPLTITSVTKSDSAVYLCASSSRSSYEQYFGPGTR
LEVD (SEQ ID NO: 106)
Figure 35b
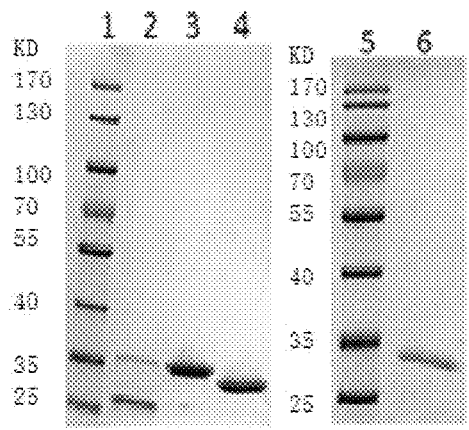
Figure 36
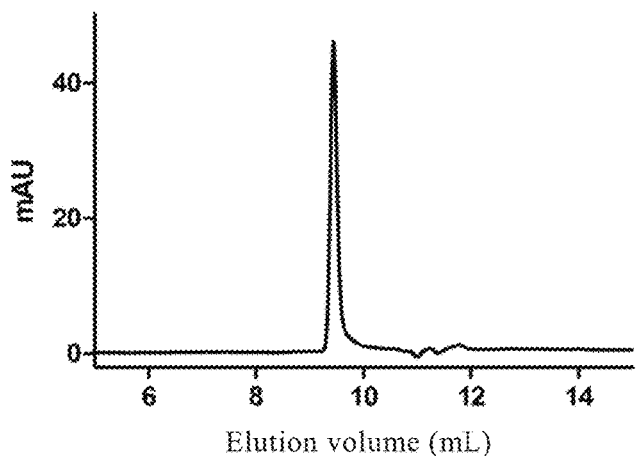
Figure 37
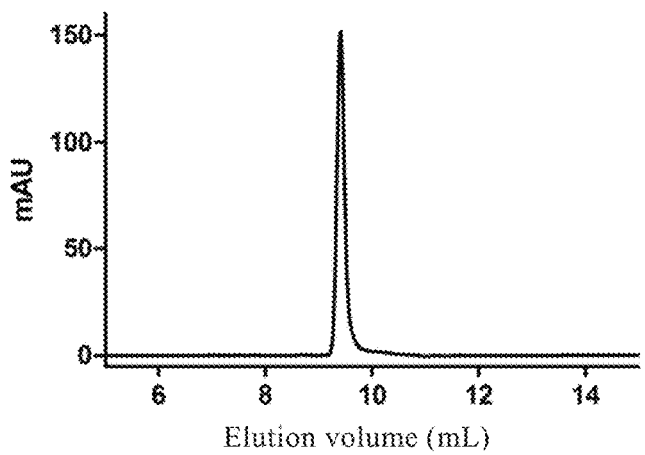
Figure 38

DQEVTQSPSSLNVPEGEN<u>V</u>S<u>I</u>NCSFTDSAIYNLQWFRQDPGKGLTSLLLVRPYQ
REQTSGRLNASLDKSSGRSTLYIER<u>I</u>QPNDSGTYFCAVRPGGAGSYQLTFGKGT
KLSVTD(SEQ ID NO: 107)
Figure 42a
KAGITQTPRYLS<u>V</u>KTGQSVTLSCSPISGHRSVSWYQQTPGQGLQFLFEYFSETQR
NKGNFPGRFSGRQFSNSRSELN<u>I</u>ES<u>V</u>TPSDSALYLCASSPNMADEQYFGPGTRLE
VD(SEQ ID NO: 108)
Figure 42b
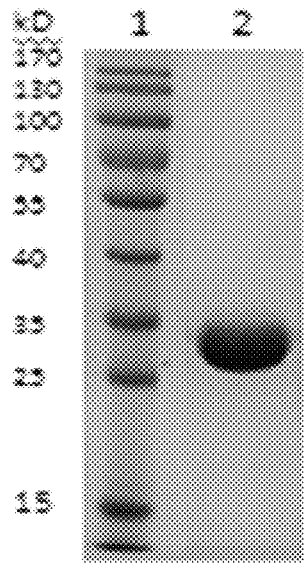
Figure 43
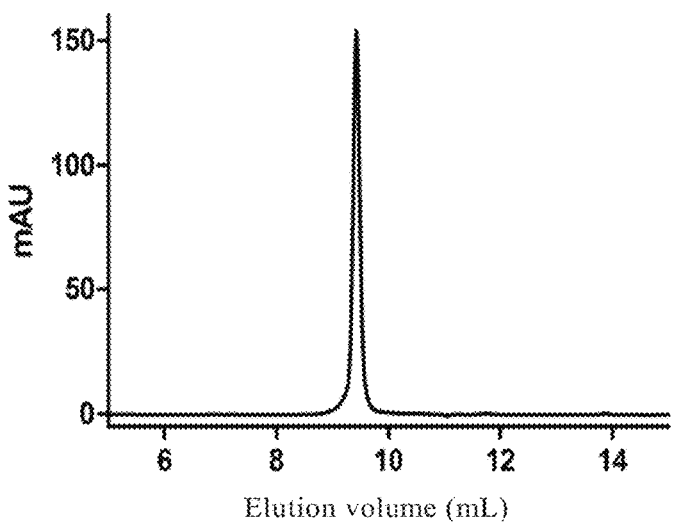
Figure 44

HIGH-STABILITY T-CELL RECEPTOR AND PREPARATION METHOD AND APPLICATION THEREOF

CROSS REFERENCE TO RELATED APPLICATIONS

This application is a national phase application under 35 U.S.C. 371 claiming priority to PCT/CN2014/080773, filed Jun. 25, 2014, which application claims priority to CN201310263384.1, filed Jun. 26, 2013, the teachings of which are hereby incorporated by reference in their entireties for all purposes.

TECHNICAL FIELD

The present invention relates to field of biotechnology, and particularly relates to a high-stability and soluble T cell receptor (TCR) mutated in its hydrophobic core domain. The present invention also relates to preparation and application of the receptor.

BACKGROUND ART

There are only two types of molecules that can recognize antigens in a specific manner. One is immunoglobulin or antibody and the other is T cell receptor (TCR), which is α/β or γ/δ heterodimeric glycoprotein on cell membrane. The physical repertoire of TCR of immune system is generated in thymus through V (D)J recombination, followed by positive and negative selections. In peripheral environment, TCRs mediate the recognition of specific Major Histocompatibility Complex-peptide complexes (pMHC) by T cells and, as such, are essential to the immunological functioning of cells in the immune system.

TCR is the only receptor for presenting particular peptide antigens in Major Histocompatibility Complex (MHC). The exogenous or endogenous peptides may be the only sign of abnormality in a cell. In the immune system, once antigen-specific TCRs bind with pMHC complexes, it causes direct physical contact of a T-cell and an antigen presenting cell (APC). Then, the interaction of other membrane molecules in T cell and APC occurs and the subsequent cell signaling and other physiological responses are initiated so that a range of different antigen-specific T cells exert immune effects on their targets.

On T cell membrane, the TCR is associated with invariant proteins of CD3 involved in mediating signal transduction to form a complex. TCRs exist in many forms, which are structurally similar but T cells expressing them have quite distinct anatomical locations and probably have different functions. The extracellular portion of TCR consists of two membrane-proximal constant domains, and two membrane-distal variable domains. The variable domains contain polymorphic loops analogous to the complementary determining regions (CDRs) of antibodies. It is these loops that form the binding site of the TCR molecule and determine peptide specificity. The MHC class I and class II ligands corresponding to TCR are also immunoglobulin superfamily proteins but are specialized for antigen presentation, with a polymorphic peptide binding site which enables them to present a diverse array of short peptide fragments at the APC cell surface.

Like immunoglobulin (antibody) as a kind of antigen recognition molecule, TCR can be developed for diagnostic and therapeutic applications. However, it is difficult to produce proteins in (water) soluble form which are made up of more than one polypeptide subunit and have a transmembrane domain because, in many cases, the proteins are stabilized by their transmembrane region. This is the case for TCR, and is reflected in scientific literatures. It is reported that a truncated form of TCR containing either only extracellular domains or only extracellular and cytoplasmic domains can be recognized by TCR-specific antibodies, thus indicating that a partial region of recombinant TCR recognized by antibodies is correctly folded. However, the production is not high, and it is not stable and/or cannot recognize MHC-peptide complexes at a low concentration.

A Soluble TCR is useful, not only for research of TCR-pMHC interactions, but also potentially as a diagnostic tool to detect infection or as a marker for autoimmune diseases. Similarly, soluble TCRs can be used to deliver a therapeutic agent, e.g., a cytotoxic compound or an immunostimulating compound, to cells presenting a particular antigen, or to inhibit T cells, e.g., those reacting with an autoimmune peptide antigen. For these purposes, modification of TCR protein is important. Especially, it is very important for heterogeneous expression of TCRs in prokaryote or eukaryote systems.

As for expression of soluble TCR in *E. coli*, when TCR is separated from the membrane, instability and low protein yield are major hurdles for developing therapeutic or diagnostic reagents with TCR or its fragment. In order to overcome inherent instability of single-chain TCRs, production of a TCR heterodimer is described in some literatures, which includes a native disulfide bridge linking the respective subunits (Garboczi, et al., (1996), *Nature* 384 (6605): 134-41; Garboczi, et al., (1996), *J Immunol* 157(12): 5403-10; Chang et al., (1994), PNAS USA 91: 11408-11412; Davodeau et al., (1993), *J. Biol. Chem.* 268(21): 15455-15460; Golden et al., (1997), *J. Imm. Meth.* 206: 163-169; U.S. Pat. No. 6,080,840). However, although such TCRs can be recognized by TCR-specific antibodies, they can only recognize a native ligand at a relatively high concentration, suggesting that the recognition is instable.

Furthermore, for production of TCRs with original antigen specificity, there are many investigations on how to improve stability of water soluble TCR fragments, including variable domains of a single-chain TCR (Novotny, et al (1991) PNAS USA 88:8646-8650), extracellular domains in a heterodimeric TCR (Garcial et al (1996) Science 274:209-219), or modification of such molecules (Shusta et al (2000) *Nature Biotechnology* 18:754-759), Boulter et al (2003) *Protein Engineering* 16:707-711). In these researches, Novotny et al used a flexible peptide for linking variable domains to construct a single-chain TCR. However, stable molecules could be obtained only after replacing hydrophobic residues exposed on surface with hydrophilic residues containing water soluble side chains. Shusta et al modified the single-chain TCR variable domain structure by introducing random mutations into the whole molecule and by displaying on yeast surface and selection with FACS. Garcia et al constructed extracellular domain 2C of an α/β TCR and native inter-chain disulfide bonds were kept in the structure. Boulter et al improved α/β heterodimer construct by introducing an artificial disulfide bond buried between two constant domains.

The approach of using disulfide between constant domains has been used for phage display of TCR vectors which have been used for generation of many high affinity TCRs (Li et al (2005) *Nature Biotechnology* 34:349-354; Liddy et al (2012) *Nature Medicine* 18:980-987). However, the inventors have found that the probability for successful production of a high-affinity TCR using such constructs is still very low, and it is difficult to obtain TCR with both high affinity and high stability. So it is necessary to develop new strategies for producing a TCR and fragments thereof having water solubility, high affinity and high stability

SUMMARY OF THE INVENTION

The object of the present invention is to provide a high-stability T cell receptor (TCR).

Another object of the present invention is to provide preparation and application of said high-stability T cell receptor.

In the first aspect of the invention, it provides a T cell receptor (TCR) having the following features:

(i) the hydrophobic core domain of the TCR is mutated; and (ii) the TCR has a stability higher than that of a corresponding TCR with wild-type hydrophobic core.

In one preferred embodiment, "mutated" refers to the hydrophobic core domain of the TCR of the present invention has mutation relative to the corresponding wild-type hydrophobic core domain of TCR.

In one preferred embodiment, "a stability higher than" refers to the stability of the TCR of the present invention increases by at least 5%, preferably at least 30%, and more preferably at least 80%, compared with the TCR having a wild-type hydrophobic core.

In one preferred embodiment, "wild-type hydrophobic core" refers to a hydrophobic core which is identical in amino acid sequence to the hydrophobic core of a naturally-occurring TCR and is not mutated.

In one preferred embodiment, "a corresponding TCR having a wild-type hydrophobic core" refers to a TCR which is identical in sequence of the other domains to those of the TCR of the present invention, except that its hydrophobic core is wild-type, compared to the TCR of the present invention whose hydrophobic core is mutated. Additionally or preferably, the "corresponding TCR with wild-type hydrophobic core" refers to a wild-type TCR which is naturally-occurring and does not contain any mutation site, and especially to sTv molecule having a wild-type α chain variable domain and β chain variable domain. The representative examples include LC13-WT.

In one preferred embodiment, the CDRs regions of the TCR are wild-type, or comprise mutations rendering increased affinity.

In one preferred embodiment, "affinity" refers to binding affinity between the TCR molecule and its corresponding antigen.

In one preferred embodiment, in TCR variable domain framework and constant domain, the hydrophobic residues whose side chain points toward surface are mutated. That is that amino acid residues exposed on surface in variable domain framework and constant domain of the TCR are mutated. Preferably, the amino acid residues mutated are amino acid residues exposing on surface in α chain and/or β chain variable domain of TCR. More specifically, the amino acid positions exposing on surface comprise positions 4, 12, 16, 93, 97, 100, and 105 in TCR α chain variable domain and the last position of α chain J gene; positions 4 and 101 in TCR β chain variable domain, and the last position of β chain J gene, and position of 3rd from the last of β chain J gene. The position numbering of amino acid is the numbering shown in IMGT (international immunogenetics database).

In one preferred embodiment, mutations of hydrophobic residues whose side chain point toward surface in variable domain framework of TCR include (but are not limited to) in α chain: 17S, A9S, A10S, V20S, A92E, A93S; I→T in position 2nd from the last of J gene short chain peptide; in β chain: I12S; or any combination thereof; wherein the numbering of amino acid position is the numbering shown in IMGT.

In one preferred embodiment, the TCR is soluble.

In one preferred embodiment, the TCR is a membrane protein.

In one preferred embodiment, the TCR comprises (a) all or part of a TCR α chain, except the transmembrane domain thereof; and (b) all or part of a TCR β chain, except the transmembrane domain thereof;

and each of (a) and (b) independently comprises a functional variable domain, or a functional variable domain and at least a part of the constant domain of TCR chain.

In one preferred embodiment, the TCR is a single-chain TCR consisting of TCR α chain variable domain and TCR β chain variable domain linked by a flexible peptide linker.

In one preferred embodiment, the mutations comprise at least one mutation at hydrophobic core.

In one preferred embodiment, the TCR has one or more mutations at the following positions: positions at hydrophobic core of α and/or β chain variable domain amino acid sequence, i.e., amino acid positions 11, 13, 19, 21, 53, 76, 89, 91, 94 of variable domain, and/or amino acid positions of the 3rd, 5th or 7th from the last of α chain J gene short chain peptide, and/or amino acid positions of 2nd, 4th or 6th from the last of β chain J gene short chain peptide, wherein the numbering of amino acid position is the numbering shown in IMGT.

In one preferred embodiment, one or more following positions in α chain variable domain of the TCR are mutated: amino acid positions 11, 13, 19, 21, 53, 76, 89, 91, or 94 of α chain variable domain, and/or amino acid positions of the 3rd, 5th or 7th from the last of α chain J gene short chain peptide, wherein the numbering of amino acid position is the numbering shown in IMGT (international immunogenetics database).

In one preferred embodiment, one or more following positions in α chain variable domain shown in SEQ ID NO:9 or SEQ ID NO:29 or SEQ ID NO:31 or SEQ ID NO:33 of the TCR are mutated: amino acid positions 11, 13, 19, 21, 53, 76, 89, 91, or 94 of α chain variable domain, and/or amino acid positions of the 3rd, 5th or 7th from the last of α chain J gene short peptide, wherein the numbering of amino acid position is the numbering shown in IMGT.

In one preferred embodiment, one or more following positions in β chain variable domain of the TCR are mutated: amino acid positions 11, 13, 19, 21, 53, 76, 89, 91, or 94 of β chain variable domain, and/or amino acid positions of 2nd, 4th or 6th from the last of β chain J gene short peptide, wherein the numbering of amino acid position is the numbering shown in IMGT.

In one preferred embodiment, one or more following positions in β chain variable domain shown in SEQ ID NO:11 or SEQ ID NO:30 or SEQ ID NO:32 or SEQ ID NO:34 of the TCR are mutated: amino acid positions 11, 13, 19, 21, 53, 76, 89, 91, or 94 of β chain variable domain, and/or amino acid positions of 2nd, 4th or 6th from the last of β chain J gene short peptide, wherein the numbering of amino acid position is the numbering shown in IMGT.

In one preferred embodiment, the α chain variable domain of the TCR comprises one or more amino acid residues selected from the group consisting of: 11L, 11M or 11E; 13V, 13R or 13K; 19V; 21I; 91L or 91I; and 94V or 94I; and/or the β chain variable domain of the TCR comprises one or more amino acid residues selected from the group consisting of: 11L or 11V; 13V; 19V; 89L; 91F or 91I; 94V or 94I; the position of 6th from the last of β chain J gene is T; and the position of 4th from the last of β chain J gene is M; wherein the numbering of amino acid position is the numbering shown in IMGT.

In one preferred embodiment, an amino acid residue of the TCR in α chain and/or β chain variable domain and exposed on surface is mutated.

In one preferred embodiment, the TCR comprises one or more amino acid residues of α chain variable domain selected from the group consisting of: 4L; 12N; 16S; 93N or 93R; 97N; 100G; 105S; and the last position of α chain J gene is D; and/or the TCR comprises one or more amino acid residues of β chain variable domain selected from the group consisting of: 4I; 101L; the last position of β chain J gene is D; and the position of 3rd from the last of β chain J gene is E.

In one preferred embodiment, wherein the TCR comprises an α chain variable domain whose amino acid sequence is selected from the group consisting of SEQ ID NOs: 15, 17, 35, 37, 39, 75, 76, 77, 78, 79, 80, 81, 82, 83, 84, 85, 97, 99, 101, 103, 105 and 107.

In one preferred embodiment, the TCR comprises a β chain variable domain whose amino acid sequence is selected from the group consisting of SEQ ID NOs: 16, 18, 36, 38, 40, 86, 87, 88, 89, 90, 91, 92, 93, 94, 95, 96, 98, 100, 102, 104, 106 and 108.

In one preferred embodiment, a combination of α chain variable domain and β chain variable domain of the TCR is selected from the group consisting of (a) α chain variable domain having amino acid sequence of SEQ ID NO: 15 and β chain variable domain having amino acid sequence of SEQ ID NO: 16;

(b) α chain variable domain having amino acid sequence of SEQ ID NO: 17 and β chain variable domain having amino acid sequence of SEQ ID NO: 18;

(c) α chain variable domain having amino acid sequence of SEQ ID NO: 15 and β chain variable domain having amino acid sequence of SEQ ID NO: 18;

(d) α chain variable domain having amino acid sequence of SEQ ID NO: 35 and β chain variable domain having amino acid sequence of SEQ ID NO: 36;

(e) α chain variable domain having amino acid sequence of SEQ ID NO: 37 and β chain variable domain having amino acid sequence of SEQ ID NO:38;

(f) α chain variable domain having amino acid sequence of SEQ ID NO:39 and β chain variable domain having amino acid sequence of SEQ ID NO:40;

(g) α chain variable domain having amino acid sequence of SEQ ID NO:75 and β chain variable domain having amino acid sequence of SEQ ID NO:86;

(h) α chain variable domain having amino acid sequence of SEQ ID NO:76 and β chain variable domain having amino acid sequence of SEQ ID NO:87;

(i) α chain variable domain having amino acid sequence of SEQ ID NO:77 and β chain variable domain having amino acid sequence of SEQ ID NO:88;

(j) α chain variable domain having amino acid sequence of SEQ ID NO:78 and β chain variable domain having amino acid sequence of SEQ ID NO:89;

(k) α chain variable domain having amino acid sequence of SEQ ID NO:79 and β chain variable domain having amino acid sequence of SEQ ID NO:90;

(l) α chain variable domain having amino acid sequence of SEQ ID NO:80 and β chain variable domain having amino acid sequence of SEQ ID NO:91;

(m) α chain variable domain having amino acid sequence of SEQ ID NO:81 and β chain variable domain having amino acid sequence of SEQ ID NO:92;

(n) α chain variable domain having amino acid sequence of SEQ ID NO:82 and β chain variable domain having amino acid sequence of SEQ ID NO:93;

(o) α chain variable domain having amino acid sequence of SEQ ID NO:83 and β chain variable domain having amino acid sequence of SEQ ID NO:94;

(p) α chain variable domain having amino acid sequence of SEQ ID NO:84 and β chain variable domain having amino acid sequence of SEQ ID NO:95;

(q) α chain variable domain having amino acid sequence of SEQ ID NO:85 and β chain variable domain having amino acid sequence of SEQ ID NO:96;

(r) α chain variable domain having amino acid sequence of SEQ ID NO:97 and β chain variable domain having amino acid sequence of SEQ ID NO:98;

(s) α chain variable domain having amino acid sequence of SEQ ID NO:99 and β chain variable domain having amino acid sequence of SEQ ID NO:100;

(t) α chain variable domain having amino acid sequence of SEQ ID NO:101 and β chain variable domain having amino acid sequence of SEQ ID NO:102;

(u) α chain variable domain having amino acid sequence of SEQ ID NO:103 and β chain variable domain having amino acid sequence of SEQ ID NO:104;

(v) α chain variable domain having amino acid sequence of SEQ ID NO:105 and β chain variable domain having amino acid sequence of SEQ ID NO:106; and (w) α chain variable domain having amino acid sequence of SEQ ID NO:107 and β chain variable domain having amino acid sequence of SEQ ID NO:108.

In one preferred embodiment, the hydrophobic core domain of α chain variable domain of the TCR has at least one following mutation: amino acid of position 19 is mutated to V, amino acid of position 21 is mutated to I, amino acid of position 91 is mutated to L, and/or the hydrophobic core domain of β chain variable domain has at least one following mutation: amino acid of position 91 is mutated to F or I, and/or amino acid at position of 4th from the last of amino acid sequence of β chain J gene short peptide is mutated to M.

In one preferred embodiment, the mutations are selected from the group consisting of:

(i) in α chain variable domain, amino acid of position 19 mutated to V, amino acid of position 21 mutated to I, amino acid of position 91 mutated to L; in β chain variable domain, amino acid of position 91 mutated to F, amino acid at position of 4th from the last of amino acid sequence of β chain J gene short peptide mutated to M; or (ii) in α chain variable domain, amino acid of position 19 mutated to V, amino acid of position 21 mutated to I, and in β chain variable domain, amino acid of position 91 mutated to I; or (iii) in α chain variable domain, amino acid of position 19 mutated to V, amino acid of position 21 mutated to I, amino acid of position 91 mutated to L; in β chain variable domain, amino acid of position 91 mutated to F.

In one preferred embodiment, the hydrophobic core domain of α chain variable domain of the TCR has at least one following mutation: L19V, L21I, I91L; and/or the hydrophobic core domain of β chain variable domain has at least one following mutation: V91F or V91I; and/or amino acid at position of 4th from the last of amino acid sequence of β chain J gene short peptide mutated from L to M.

In one preferred embodiment, the mutations are selected from the group consisting of:

(i) L19V, L21I, I91L in α chain variable domain, V91F in β chain variable domain, and amino acid at position of 4th from the last of amino acid sequence of β chain J gene short peptide mutated from L to M; or (ii) L19V, L21I in α chain variable domain, and V91I in β chain variable domain; or (ii) L19V, L21I, I91L in α chain variable domain, and V91I in β chain variable domain;

wherein the numbering of amino acid position is the numbering shown in IMGT.

In one preferred embodiment, the TCR further has a disulfide bond linking α chain constant domain and β chain constant domain.

In one preferred embodiment, the disulfide bond is present in natural TCR or artificially introduced.

In one preferred embodiment, the disulfide bond artificially introduced is located between α and β chains constant domains of the TCR.

In one preferred embodiment, the artificially introduced cysteine residues to form a interchain disulfide bond replace at least one pair of amino acid residues of α and β chains, which include but are not limited to:

(a) T of α chain constant domain at position 48 and S of β chain constant domain at position 57; or (b) T of α chain constant domain at position 45 and S of β chain constant domain at position 77; or (c) T of α chain constant domain at position 10 and S of β chain constant domain at position 17; or (d) T of α chain constant domain at position 45 and D of β chain constant domain at position 59; or (e) S of α chain constant domain at position 15 and E of β chain constant domain at position 15; or (f) S of α chain constant domain at position 61 and S of β chain constant domain at position 57; or (g) L of α chain constant domain at position 50 and S of β chain constant domain at position 57; or (h) S of α chain constant domain at position 15 and V of β chain constant domain at position 13; or (i) L of α chain constant domain at position 12 and S of β chain constant domain at position 17; or (j) S of α chain constant domain at position 61 and R of β chain constant domain at position 79; or (k) L of α chain constant domain at position 12 and F of β chain constant domain at position 14; or (l) V of α chain constant domain at position 22 and F of β chain constant domain at position 14; or (m) Y of α chain constant domain at position 43 and L of β chain constant domain at position 63; or (n) Y of α chain constant domain at position 10 and S of β chain constant domain at position 17.

The numbering of amino acid position replaced in α chain and β chain constant domain as used herein is the position numbering shown in reference of *Stable, souble T-cell receptor molecules for crystallization and therapeutics* (Jonathan M. Boulter et al., 2003, Protein Engineering 16 (9): 707-711).

In one preferred embodiment, the TCR is screened out by phage display technology.

In one preferred embodiment, the TCR is bound with a conjugate (covalently or by other means).

In one preferred embodiment, the conjugate is one or more selected from the group consisting of:

(1) a detectable marker;
(2) a therapeutic agent; and
(3) a PK modifying moiety.

Preferably, the detectable marker comprises: a fluorescent or luminescent label, a radiolabel, a MRI (magnetic resonance imaging) or CT (computer tomography X-ray) contrast agent, or an enzyme capable of producing a detectable product.

Preferably, the therapeutic agent comprises: a radionuclide, a biotoxin, a cytokine (e.g., IL-2, etc.), an antibody, an antibody Fc fragment, a scFv antibody fragment, a gold nanoparticle/nanorod, a virus particle, a liposome, a nanomagnetic particle, a prodrug activating enzyme (e.g., DT-diaphorase (DTD) or a biphenyl hydrolase-like protein (BPHL)), a chemotherapeutic agent (e.g., cisplatin) or a nano-particle in any form.

In one preferred embodiment, the conjugate is an antibody against CD3 and linked to C- or N-terminal of the TCR α and/or β chains.

In the second aspect of the invention, it provides a nucleic acid molecule comprising a sequence encoding a TCR according to the first aspect of the invention, or its complementary sequence.

In the third aspect of the invention, it provides a vector comprising a nucleic acid molecule according to the second aspect of the invention.

In the fourth aspect of the invention, it provides a host cell which comprises a vector according to the third aspect of the invention or in which an exogenous nucleic acid molecule according to the second aspect of the invention is integrated in chromosome.

In one preferred embodiment, the host cell is selected from the group consisting of: a prokaryotic and an eukaryotic cell, such as an *Escherichia coli*, a yeast, a CHO cell and so on In the fifth aspect of the invention, it provides a method for preparing the TCR according to the first aspect of the invention, which comprises:

(i) incubating the host cell according to the fourth aspect of the invention, thereby expressing the TCR according to the first aspect of the invention; and (ii) isolating or purifying the TCR.

In the sixth aspect of the invention, it provides a TCR complex comprising one or more TCR molecules in the first aspect of the invention.

In one preferred embodiment, the complex comprises a complex formed by the TCR of the invention bound with a therapeutic agent or a detectable marker.

In one preferred embodiment, the complex comprises two or more TCR molecules.

In the seventh aspect of the invention, it provides a use of the TCR of the first aspect of the invention for manufacture of a medicine for treating tumor, viral infection or autoimmune disease.

In the eighth aspect of the invention, it provides a pharmaceutical composition comprising a pharmaceutically acceptable carrier and a safe and effective dosage of any TCR of the first aspect of the invention.

In the ninth aspect of the invention, it provides a method for treating a disease which comprises administering the TCR of the first aspect of the invention, or the TCR complex of the sixth aspect of the invention, or a pharmaceutical composition of the eighth aspect of the invention to a subject in need of.

In one preferred embodiment, the disease includes tumor, autoimmune disease and viral infection.

In the tenth aspect of the invention, it provides a method for preparing the TCR of the first aspect of the invention, which comprises:

9

(i) introducing a mutation of amino acid residue in a hydrophobic core domain of a TCR; and (ii) screening a TCR whose stability is enhanced significantly, thereby obtaining a TCR of the first aspect of the invention.

In one preferred embodiment, the screening method includes but is not limited to phage display technique.

In one preferred embodiment, in step (ii), the TCR having a mutated hydrophobic core domain is displayed by phage display technique, and then selected.

In one preferred embodiment, the method further comprises a step of determining sequence, activities and/or other features of TCR screened out.

It should be understood that in the present invention, the technical features specifically described above and below (such as the examples) can be combined with each other, thereby constituting a new or preferred technical solution, which needs not be specified one by one.

DESCRIPTION OF FIGURES

FIGS. 2a and 2b respectively show amino acid sequence and nucleic acid sequence (SEQ ID NO: 9 and 10) of TCR α chain variable domain after site direct mutation. The amino acid sequence is an optimization of the TCR α chain variable domain amino acid sequence disclosed in patent literature (WO2012/013913). Specifically, the hydrophobic residues in variable domain having side chains point toward surface are mutated into hydrophilic or polar residues. The bold and underlined letters are amino acid residues after mutation.

FIGS. 3a and 3b respectively show amino acid sequence and nucleic acid sequence (SEQ ID NO:11 and 12) of TCR β chain variable domain after site direct mutation. The amino acid sequence is an optimization of the TCR beta chain variable domain amino acid sequence disclosed in patent literature (WO2012/013913). Specifically, the hydrophobic residues in variable domain having side chains point toward surface are mutated into hydrophilic or polar residues. The bold and underlined letters are amino acid residues after mutation.

FIG. 4 shows the ligation manner of each primer in the process of constructing MAGE-sTv-WT.

FIGS. 5a and 5b respectively show the amino acid sequence and nucleic acid sequence (SEQ ID NO: 13 and 14) of the linker between α and β chain in the process of constructing sTv mutant strains libraries.

FIGS. 6a and 6b respectively show the α and β chain variable domain amino acid sequence (SEQ ID NO: 15 and 16) of sTv mutant strain MG29. The mutated residues relative to reference MAGE-sTv-WT are bold and underlined.

FIGS. 7a and 7b respectively show the α and β chain variable domain amino acid sequence (SEQ ID NO: 17 and 18) of sTv mutant strain E8F1. The mutated residues relative to reference MAGE-sTv-WT are bold and underlined.

FIGS. 8a and 8b respectively show the α and β chain variable domain amino acid sequence (SEQ ID NO: 15 and 18) of sTv mutant strain P8F2. The mutated residues relative to reference MAGE-sTv-WT are bold and underlined.

FIG. 9 shows OD values of different mutant strains screened out and MAGE-sTv-WT in ELISA against antigen MAGEA3, EBV, Flu, NY-ESO.

10

FIGS. 10a and 10b respectively show amino acid sequences of the α chain variable domain (SEQ ID NO: 29) and β chain variable domain (SEQ ID NO: 30) of LC13-WT.

FIGS. 11a and 11b respectively show amino acid sequences of the α chain variable domain (SEQ ID NO: 31) and β chain variable domain (SEQ ID NO: 32) of JM22-WT.

FIGS. 12a and 12b respectively show amino acid sequences of the α chain variable domain (SEQ ID NO: 33) and β chain variable domain (SEQ ID NO: 34) of 1G4-WT.

FIGS. 13a and 13b respectively show amino acid sequences of the α chain variable domain (SEQ ID NO: 35) and β chain variable domain (SEQ ID NO: 36) of LC13-sTv.

FIGS. 14a and 14b respectively show amino acid sequences of the α chain variable domain (SEQ ID NO: 37) and β chain variable domain (SEQ ID NO: 38) of JM22-sTv.

FIGS. 15a and 15b respectively show amino acid sequences of the α chain variable domain (SEQ ID NO: 39) and β chain variable domain (SEQ ID NO: 40) of 1 G4-sTv.

FIG. 16 shows amino acid sequence of a linker (SEQ ID NO: 41) used for constructing a sTV single-chain molecule.

Figure 17:
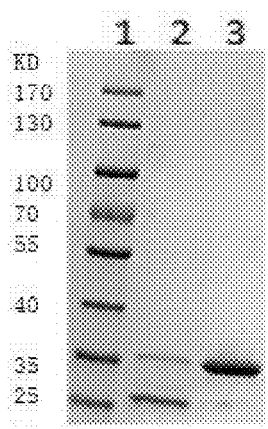

FIG. 17 shows SDS-PAGE result of purified proteins LC13-WT and LC13-sTv. Lane 1: molecular weight markers, Lane 2: LC13-WT, lane 3: LC13-sTv.

Figure 18A:
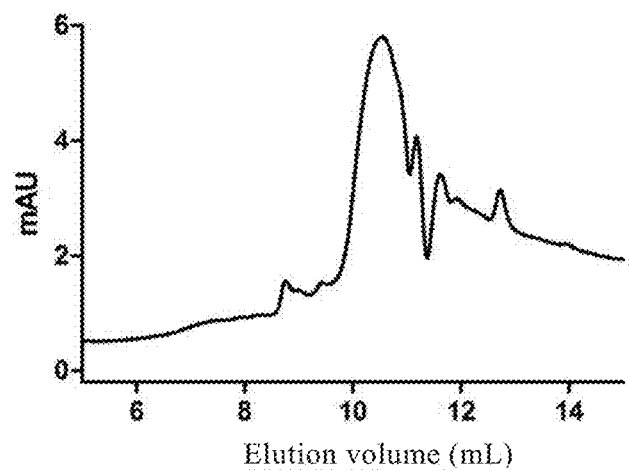
Figure 18B:
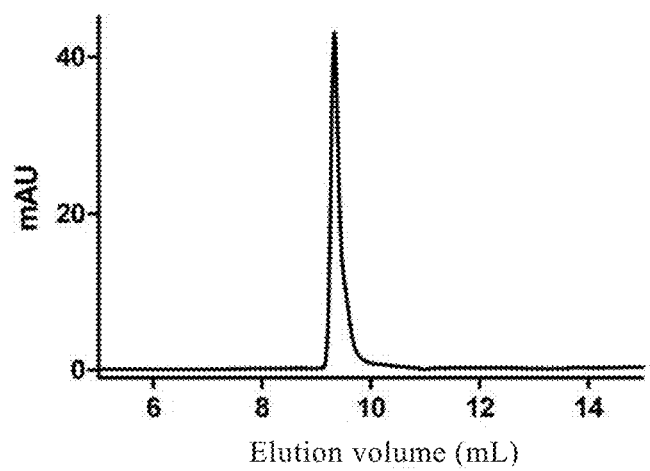

FIGS. 18a and 18b respectively show SEC profile of purified proteins LC13-WT and LC13-sTv.

Figure 19:
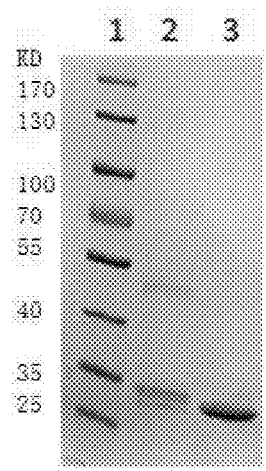

FIG. 19 shows the SDS-PAGE result of purified protein JM22-WT and JM22-sTv. Lane 1: molecular weight markers, Lane 2: JM22-WT, Lane 3: JM22-sTv.

Figure 20A:
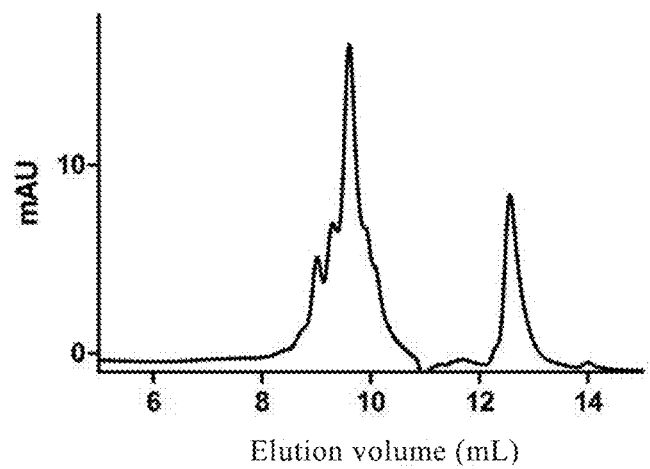
Figure 20B:
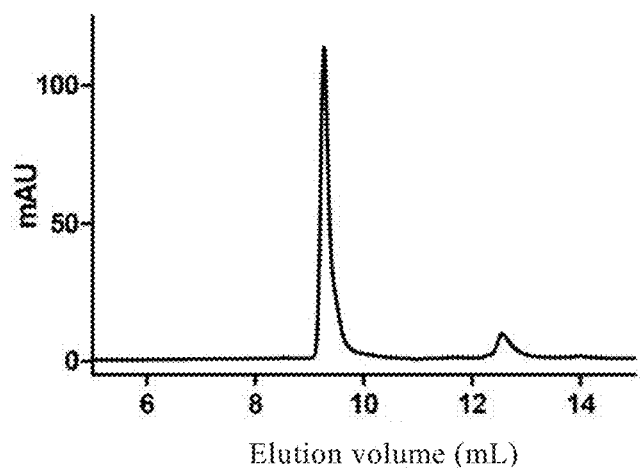

FIGS. 20a and 20b respectively show SEC profile of purified protein JM22-WT and JM22-sTv.

Figure 21:
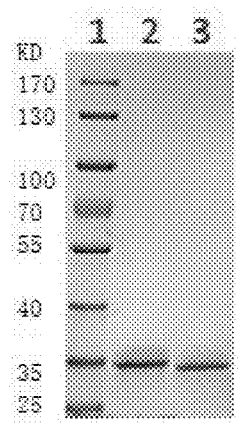

FIG. 21 shows the SDS-PAGE result of purified protein 1 G4-WT and 1 G4-sTv. Lane 1: molecular weight markers, Lane 2: 1G4-WT, Lane 3: 1G4-sTv.

Figure 22A:
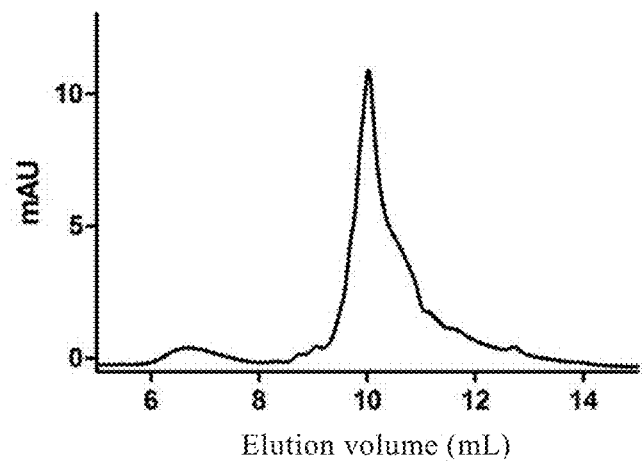
Figure 22B:
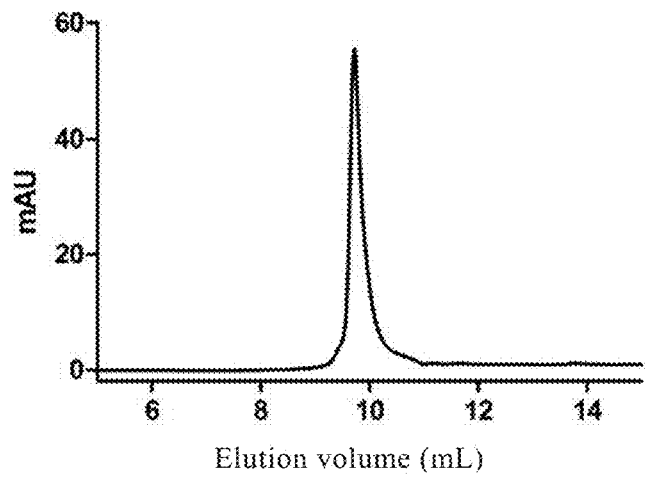

FIGS. 22a and 22b respectively show SEC profile of purified protein 1G4-WT and 1 G4-sTv.

Figures 23, 24:
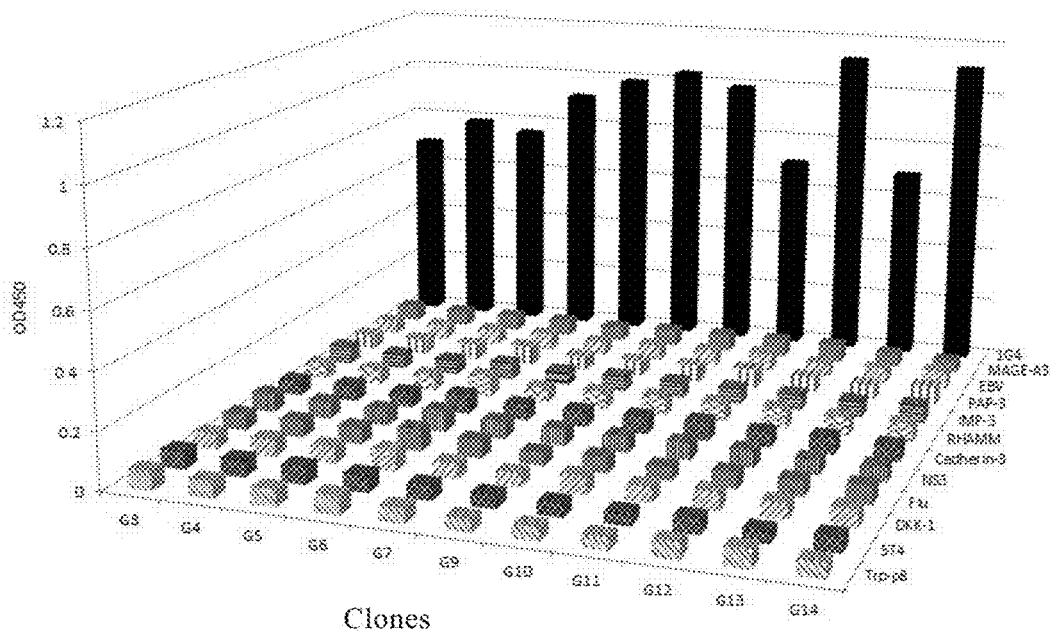

FIG. 23 shows amino acid sequence of 1G4-sTv (SEQ ID NO: 42).

FIG. 24 shows OD values of 1G4-sTv mutant strain against different antigens.

FIG. 25 shows amino acid sequence of α chain variable domain of 1G4-sTv mutant strains screened out and having high stability (SEQ ID NOs: 75-85).

FIG. 26 shows amino acid sequence of β chain variable domain of 1 G4-sTv mutant strains screened out and having high stability (SEQ ID NOs: 86-96).

FIG. 27 shows DSC graph of 1G4-sTv mutant strains with high stability.

FIG. 28 shows DSC graph of 1G4-WT.

FIGS. 29a and 29b respectively show amino acid sequences of α chain variable domain (SEQ ID NO: 97) and β chain variable domain (SEQ ID NO: 98) of G15 having high stability.

Figure 30:
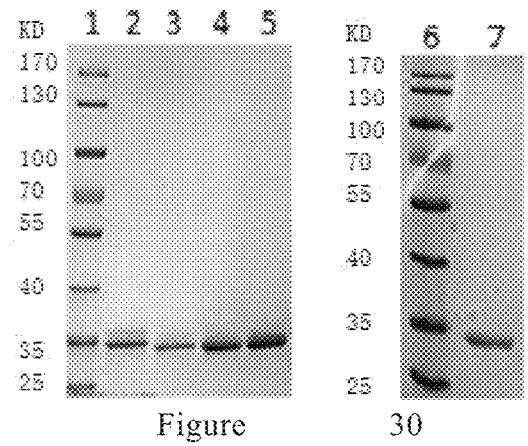

FIG. 30 shows the SDS-PAGE result of purified protein 1G4-WT, 1G4-sTv, G13, G15, G9. Lane 1: molecular weight markers, Lane 2: 1G4-WT, Lane 3: 1G4-sTv, Lane 4: G13, Lane 5: G15, Lane 6: molecular weight markers, Lane 7: G9.

Figure 31A:
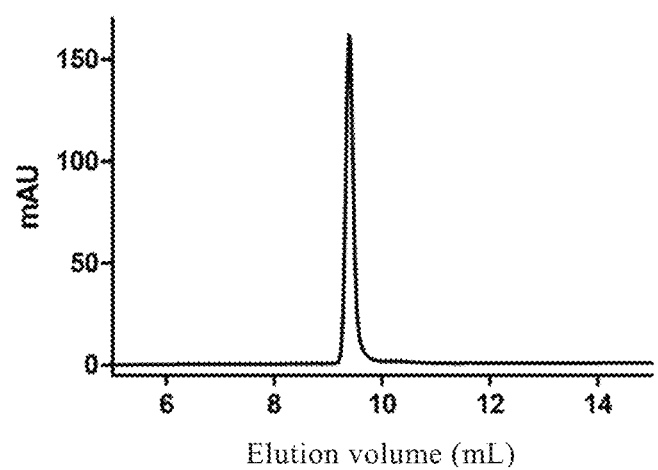
Figure 31B:
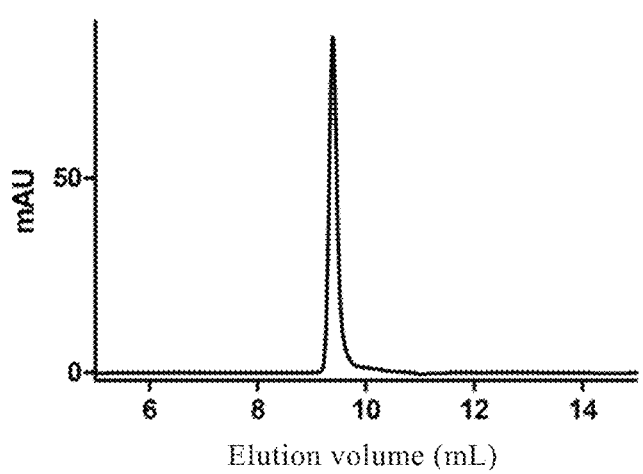

FIGS. 31a, 31b and 31c respectively show SEC profile of purified proteins G9, G13 and G15.

FIGS. 32a and 32b respectively show amino acid sequences of the α chain variable domain (SEQ ID NO: 99) and β chain variable domain (SEQ ID NO: 100) of LC13-G9.

FIGS. 33a and 33b respectively show amino acid sequences of the α chain variable domain (SEQ ID NO: 101) and β chain variable domain (SEQ ID NO: 102) of LC13-G15.

FIGS. 34a and 34b respectively show amino acid sequences of the α chain variable domain (SEQ ID NO: 103) and β chain variable domain (SEQ ID NO: 104) of JM22-G9.

FIGS. 35a and 35b respectively show amino acid sequences of the α chain variable domain (SEQ ID NO: 105) and β chain variable domain (SEQ ID NO: 106) of JM22-G15.

FIG. 36 shows the SDS-PAGE result of purified proteins LC13-WT, LC13-sTv, LC13-G15, and LC13-G9. Lane 1: molecular weight markers, Lane 2: LC13-WT, Lane 3: LC13-sTv, Lane 4: LC13-sTv, Lane 5: molecular weight markers, Lane 6: LC13-G9.

FIG. 37 shows SEC profile of purified protein LC13-G9.

FIG. 38 shows SEC profile of purified protein LC13-G15.

Figure 39:
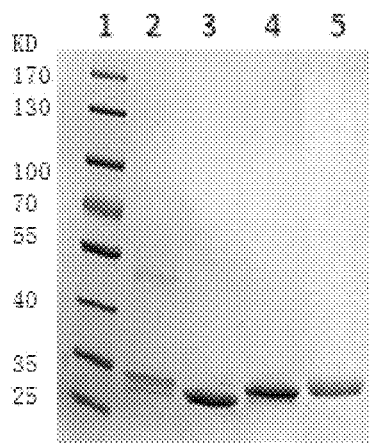

FIG. 39 shows the SDS-PAGE result of purified proteins JM22-WT, JM22-sTv, JM22-G15, and JM22-G9. Lane 1: molecular weight markers, Lane 2: JM22-WT, Lane 3: JM22-sTv, Lane 4: JM22-G15, Lane 5: JM22-G9.

Figure 40:
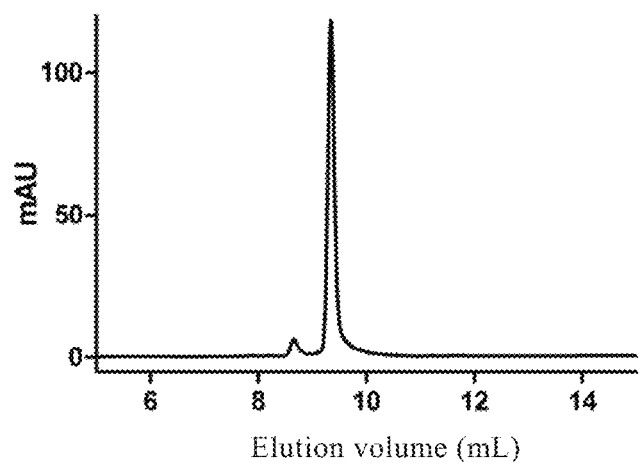

FIG. 40 shows SEC profile of purified protein JM22-G9.

Figure 41:
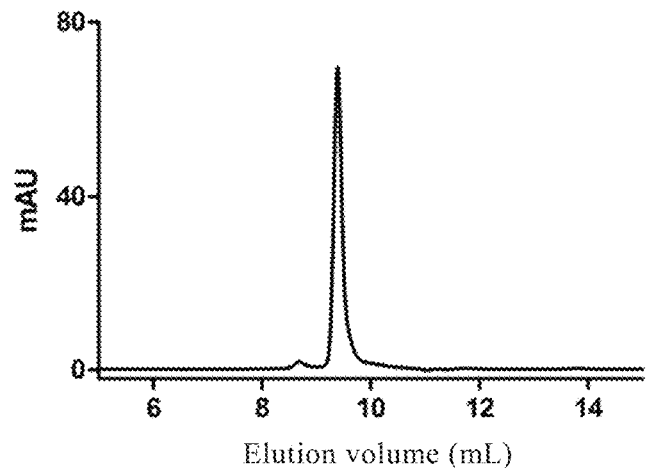

FIG. 41 shows SEC profile of purified protein JM22-G15.

FIGS. 42a and 42b respectively show amino acid sequences of α chain variable domain (SEQ ID NO: 107) and β chain variable domain (SEQ ID NO: 108) of MAGE-G15.

FIG. 43 shows the SDS-PAGE result of purified protein MAGE-G15. Lane 1: molecular weight markers, Lane 2: MAGE-G15.

FIG. 44 shows SEC profile of purified protein MAGE-G15.

Figure 45:
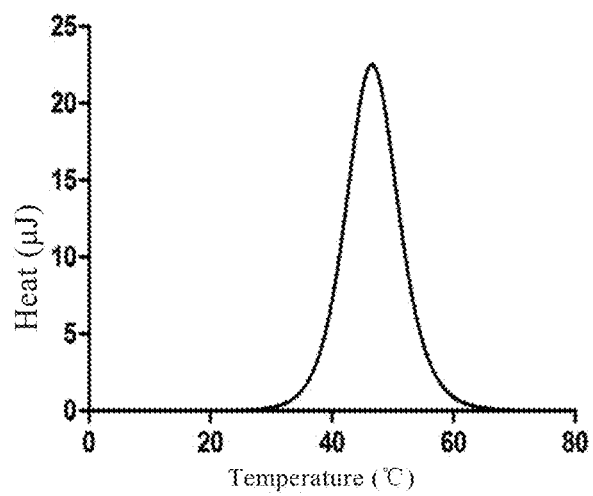

FIG. 45 shows DSC graph of purified protein MAGE-G15.

Figure 46:
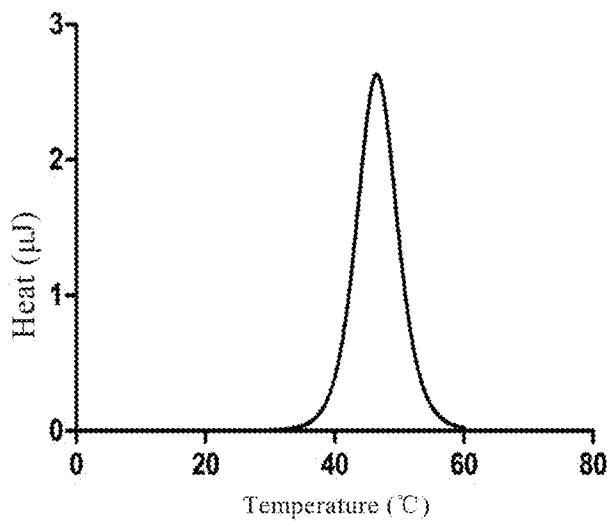

FIG. 46 shows DSC graph of purified protein G15.

Figure 47:
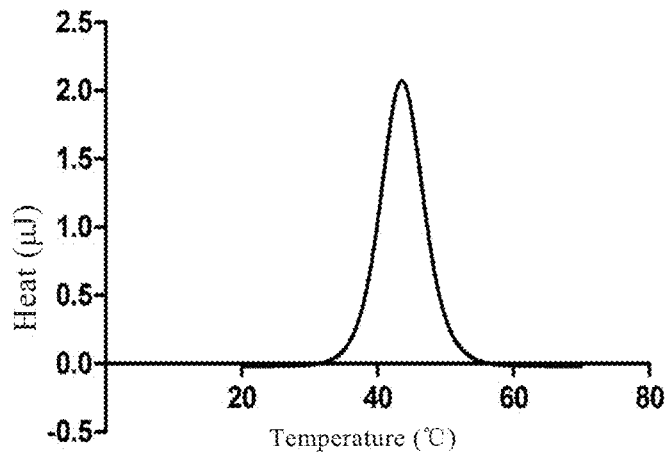

FIG. 47 shows DSC graph of purified protein LC13-sTv.

Figure 48A:
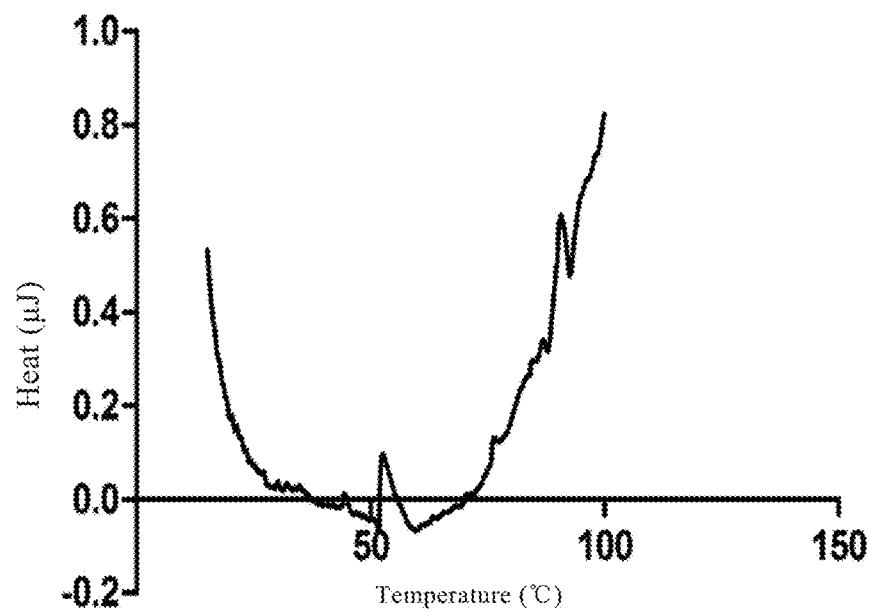
Figure 48B:
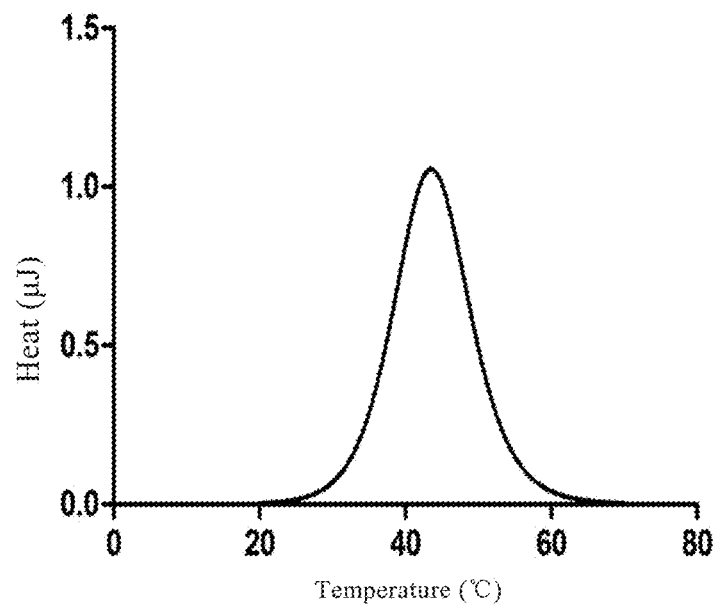

FIGS. 48a and 48b respectively show DSC graphs of purified proteins JM22-WT and JM22-sTv.

Figure 49A:
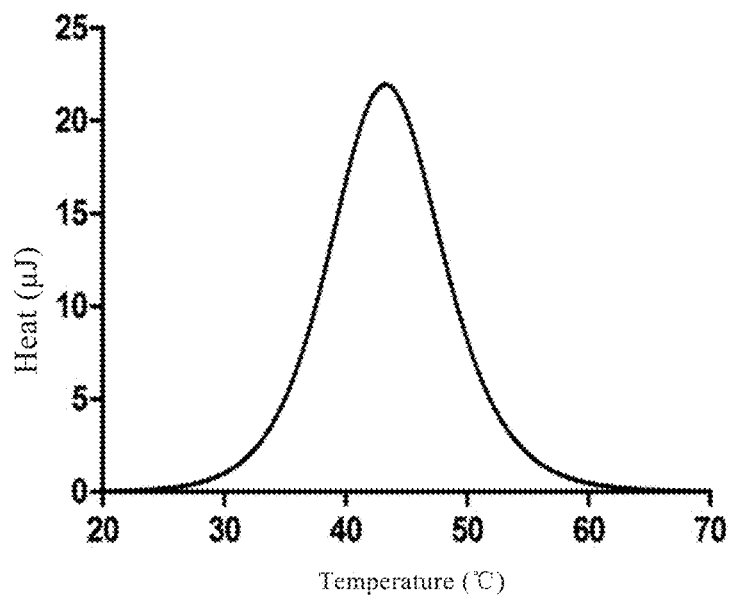
Figure 49B:
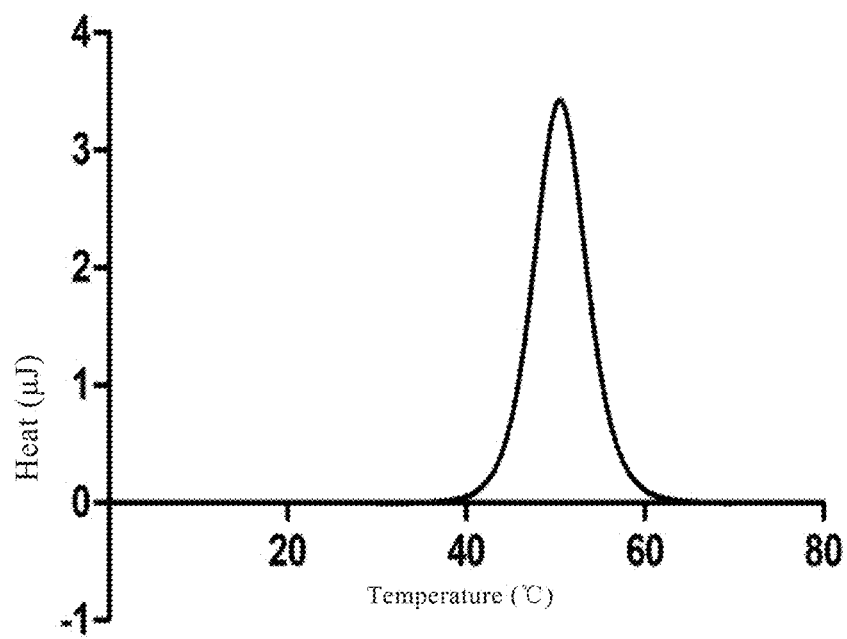

FIGS. 49a and 49b respectively show DSC graphs of purified proteins LC13-G9 and LC13-G15.

DETAILED DESCRIPTION OF INVENTION

Through extensive and intensive researches, the inventors have unexpectedly and firstly discovered that a mutant TCR having high stability and especially having solubility can be obtained after hydrophobic core domain of the TCR is targetedly mutated. Based on this discovery, the inventors have completed the present invention.

The present inventors have used an optimized TCR protein structure to construct a TCR molecule with high stability by changing TCR hydrophobic core. In the present invention, a new type of single-chain TCR variable domain is constructed by directed molecular evolution method, and the best hydrophobic core is isolated. For a TCR fragment having such a novel hydrophobic core, hydrophobic residues exposed on surface of TCR variable domain can be substituted by hydrophilic or polar residues for further improvement.

Definition

TCR

Native α-β heterodimeric TCRs have an α chain and a β chain. Broadly, each chain comprises variable, joining and constant regions, and the beta chain also usually contains a short diversity region between the variable and joining regions, but this diversity region is often considered as part of the joining region. Three CDRs (Complementary Determining Regions) of each variable region are embedded in a framework of the variable region and the hydrophobic core is also located in the framework of the variable region. There are several types of α chain variable regions (Vα) and several types of β chain variable regions (Vβ). In international immunogenetics database (IMGT), the Vα types and Vβ types are referred to nomenclature separately by a unique TRAV number and a TRBV number. TRAJ and TRBJ refer to the joining regions of the TCR. As used in the present invention, α chain J gene refers to TRAJ and β chain J gene refers to TRBJ. The α and β chains of a TCR are generally regarded as each having two "domains", namely variable and constant domains. The variable domain consists of a concatenation of variable region and joining region. Therefore, in the present specification and claims, the term "TCR α variable domain" refers to the concatenation of TRAV and TRAJ and the term "TCR β variable domain" refers to the concatenation of TRBV and TRBJ.

The amino acid sequences of TCR and the variable domain framework thereof including the specific location number of hydrophobic core position in IMGT defined by the IMGT are widely known and accessible to those working in the TCR field. For example, they can be found in the IMGT public database. In present invention, the amino acid position numbering is the numbering shown in IMGT, unless otherwise indicated. If the position numbering listed in IMGT is changed, the amino acid position numbering of TCR shown in IMGT of Jan. 1, 2013 version shall prevail.

As used herein, the term "hydrophobic core" (also called "hydrophobic center") refers to the core area mostly consisting of hydrophobic amino acids which generally exist in the inner of molecular structure of protein domains when any protein being dissolved in water. In TCR, hydrophobic core of TCR α variable domain is amino acid positions 11, 13, 19, 21, 53, 76, 89, 91, 94 of variable domain, and amino acid positions of the 3rd, 5th or 7th from the last of a chain J gene (TRAJ) short peptide; hydrophobic core of TCR β variable domain is amino acid positions 11, 13, 19, 21, 53, 76, 89, 91, 94 of variable domain, and amino acid position of the 2nd, 4th or 6th from the last of β chain J gene (TRBJ) short peptide. The numbering of amino acid position above is the numbering shown in IMGT.

Figure 1:
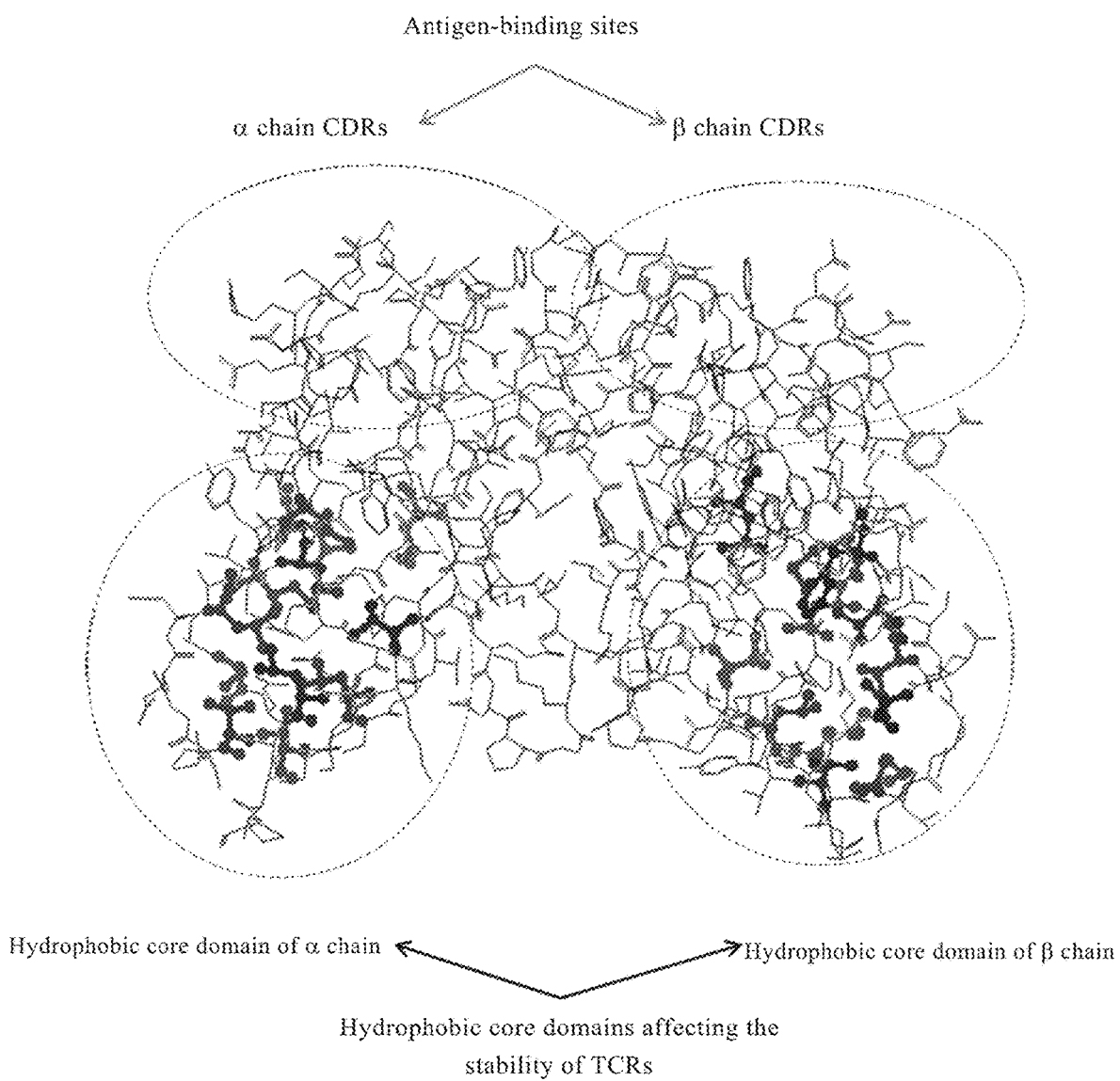
FIG. 1 shows a structure diagram of a typical TCR variable domain. Such TCR is a wild-type TCR specific to tumor antigen MAGE A3 HLA A1.

FIG. 1 shows the variable domain structure diagram of wild-type TCR specific to cancer antigen MAGE A3 HLA A1 and the bold amino acid residues shown in two ellipses of bottom left and bottom right are the hydrophobic core located in α and β chain variable domain framework, respectively. Antigen-binding sites of TCR are in the CDRs regions, and CDRs regions determine the binding affinity between TCR and corresponding antigen thereof. As shown in the figure, the hydrophobic core is not in the CDRs regions and mutations of hydrophobic core would not affect the binding affinity between TCR and its corresponding antigen. However, mutations of hydrophobic core affect the stability of TCR according to the study of the inventors.

It should be understood that the structure diagram of the TCR is used only for explaining the present invention but not to limit the scope of the present invention in any way.

The term "sTv" refers to a single chain TCR with a functional domain consisting of TCR α and β chain variable domains linked by a flexible peptide linker. The flexible peptide chain may be any peptide chain suitable for linking TCR α and β variable domains and the amount of amino acid residues in the flexible peptide chain can be, but not limited to, 1-50.

The term "stability" refers to any aspect of protein stability. Compared with the original wild-type protein, the high-stability protein screened out has one or more of the following characteristics: more resistant to unfolding, more resistant to inappropriate or undesirable folding, stronger renaturability, stronger expression ability, higher protein renaturation yield, increased thermal stability, and increased stability under a variety of environments (e.g., PH value, salt concentration, in presence of detergents or denaturing agents).

Phage Display System and Screening TCR with High Stability

When a phage display system is used to isolate a receptor, the final receptor is screened out based on two important properties. The first is the binding strength or affinity to its ligand, and the second is the display-density on the surface of a phage. The first property is a basis for protein affinity evolution, which guides all methodology development for generation of high affinity receptors. A simple description may be given as follows: when a receptor displaying library is applied to a ligand, the receptors with higher binding strength will bind to the ligand for a faster speed and/or a longer retention time and resistant to more stringent washing processes, so such receptors with their encoding genes will be captured and then amplified in subsequence processes. On the other hand, when the affinity of receptor-ligand interaction has not been altered or changed a little or even lower, affinity plays no role for the selection and display-density should govern the evolution results. This means that when more correct folded receptor molecules are displayed on a single phage particle or more phage particle displaying one or more such receptors, the receptor and encoding gene have more opportunities to bind ligand, and under specified washing conditions, such receptor shall be retained more and thereby be captured and amplified in subsequent selections. Based on the second property, more stable protein can be isolated by using phage display or other directed molecular display technologies. The inventors have designed directed evolution libraries of the TCR protein hydrophobic core for isolating more stable proteins or TCRs. It has been confirmed that such hydrophobic cores have no effects on binding strength of a TCR to its ligand pMHC or pHLA, as TCR binds pMHC through its CDRs.

In present invention, phage display technology is used to isolate more stable protein constructs. In one preferred embodiment, a TCR extracellular domain with specificity for cancer antigen pMHC of MAGE A3 HLA A1 was used for testing the hypothesis. The extracellular domain is synthesized according to a sequence in patent reference. When it is expressed on surface of filamentous phages, the TCR binding to pMHC can be detected by ELISA and the interaction strength can be determined. However, when using published methods such as mutating hydrophobic residues in the variable domains and exposed on surface into hydrophilic or polar residues, the single-chain TCR form (sTv) consisting of a and chain variable domains of TCR displayed by phages cannot show any binding function as detected in ELISA. However, when a library containing restricted random mutation of hydrophobic core of variable domain in a single chain TCR (sTv) was cloned into phage display vector and, after several rounds of screening, some clones with high stability were unexpectedly obtained. Then binding with corresponding pMHC were detected with ELISA.

Active Polypeptides

In the present invention, the terms "the polypeptide(s) of the present invention", "TCR(s) of the present invention", "T cell receptor(s) of the present invention" are interchangeably used and all refer to a T cell receptor (TCR) having mutations in its hydrophobic core region and having a stability significantly higher than that of a corresponding TCR with wild-type hydrophobic core.

In addition, the polypeptide of the present invention may further comprise other mutations outside of the hydrophobic core region, especially mutations that can increase affinity and mutations of amino acid residues exposed on surface in TCR variable domain.

These additional variations outside of hydrophobic core region include, but are not limited to, deletions, insertions and/or substitutions of 1-6 (typically 1-5, preferably 1-3, more preferably 1-2, and most preferably 1) amino acids, and addition of one or more (typically less than 5, preferably less than 3, and more preferably less than 2) amino acids at C-terminus and/or N-terminus. For example, a protein's functions are usually unchanged when an amino residue is substituted by a similar or analogous one in the art. Further, the addition of one or several amino acids at C-terminus and/or N-terminus generally will not change the structure and function of protein. Furthermore, the terms also include the polypeptide of the present invention in monomer and polymer form.

It should be understood, amino acid names used herein are internationally accepted single alphabetical identity and its corresponding abbreviations of amino acid name with three English letter. They are Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), and Val (V). In this application, the expression for amino acid substitution such as L19V means at position 19 according to positions numbering in IMGT, L (leucine) is replaced by V (valine). Meaning of other expression written in same way for amino acid substitution may refer to this example.

The present invention further includes the active fragments, derivatives and analogs of the polypeptide of the present invention. As used herein, the terms "fragments", "derivatives" and "analogs" refer to the polypeptides that can bind with a ligand molecule. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of TCR of the present invention with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6His. According to the subject application, these fragments, derivatives and analogs are within the scope commonly known by the skilled person.

A class of preferred active derivatives is the polypeptides formed by replacing at most 5, preferably at most 3, more preferably at most 2, and most preferably 1 amino acid of the amino acid sequence of the polypeptide of the present invention with the amino acid having similar or analogous property. These conservative variant polypeptides are preferably formed by carrying out the amino acid replacement according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |

TABLE A-continued

| Initial residue | Representative substitution | Preferred substitution |
|---|---|---|
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides the analogues of TCR of the present invention. These analogues differ from TCR of the present invention in amino acid sequence or modifications that do not affect the sequence, or by both. Also included are analogues which include residues other than those naturally occurring L-amino acids (e.g., D-amino acids) or non-naturally occurring or synthetic amino acids (e.g., beta- or gamma-amino acids). It is understood that the polypeptides of the present invention are not limited to the representative polypeptides listed hereinabove.

Modifications (which do not normally alter the primary sequence) include in vivo or in vitro chemical derivation of polypeptides, e.g., acetylation, or carboxylation. Glycosylation is also included in modification, e.g., the polypeptides produced by glycosylation modification during its synthesis and processing or in the further processing steps. These modifications can be achieved by exposing the polypeptide to enzymes for glycosylation (e.g., mammalian glycosylating or deglycosylating enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties.

The polypeptides of the present invention can be used in a form of pharmaceutically or physiologically acceptable salt derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Other salts include salts formed with alkali metals or alkaline earth metals (such as sodium, potassium, calcium or magnesium), and esters, carbamate or other conventional "prodrug" forms.

Polypeptides of the present invention can be provided in form of multivalent complexes. Multivalent TCR complex of the present invention comprises two, three, four or more TCR molecules linked with another molecule.

Encoding Sequence

The present invention further relates to polynucleotides encoding the TCR of the present invention.

The polynucleotides of the present invention can be in a form of DNA or RNA. DNA may be the coding strand or non-coding strand. For example, the coding sequence encoding the mature polypeptide can be identical to the coding sequence indicated in SEQ ID NO: 10, or can be a degenerate variant thereof. As used herein, "degenerate variant" refers to a nucleic acid sequence which encodes the protein having the amino acid sequence of SEQ ID NO:9, but is different from the corresponding coding sequence in SEQ ID NO: 10.

The full-length nucleotide sequence of the present invention, or a fragment thereof can usually be obtained by but not limited to the PCR amplification, recombination or synthetic methods. At present, the DNA sequences encoding polypeptides of the present invention (or fragments thereof, or derivatives thereof) can be obtained completely by chemical synthesis. Then the DNA sequences can be introduced into various existing DNA molecules (for example vectors) and cells known in the art.

The present invention also includes a vector containing the polynucleotide of the present invention, and a host cell engineered by the vector or the coding sequence of the present invention.

Moreover, the present invention further comprises polyclonal antibodies or monoclonal antibodies specific to TCR polypeptide of the present invention, especially the monoclonal antibodies.

Preparation Method

One method for generating TCRs of the present invention is to screen the high-stability TCRs from the diverse library of phage particles displaying such TCRs.

Mutations may be carried out using any appropriate methods including, but not limited to, those based on polymerase chain reaction (PCR), restriction enzyme based cloning, or ligation independent cloning (LIC) procedures. These methods are detailed in many of the standard molecular biology texts. For further details regarding polymerase chain reaction (PCR) mutagenesis and restriction enzyme based cloning, see Sambrook & Russell, (2001) Molecular Cloning—A laboratory Manual ($3^{rd}$ Ed) CSHL press. More information on the procedure of LIC can be found in Rashtchian, (1995) *Curr Opin Biotechnol* 6 (1): 30-6.

The polypeptide of the present invention can be a recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

With the conventional recombinant DNA technique, the polynucleotide of the present invention can be used to express or produce recombinant polypeptides of the present invention. Generally, the method comprises the following steps:

(1) Transforming or transfecting a suitable host cell with a polynucleotide or variant thereof encoding TCR polypeptide of the present invention or a recombinant expression vector containing said polynucleotide;

(2) Culturing the host cell in a suitable culture medium;

(3) Isolating and purifying the TCR polypeptide of the present invention from the culture medium or cell.

The recombinant polypeptide may be expressed in cells or on the cell membrane, or secreted out of the cell. If desired, the physical, chemical and other properties can be utilized in various isolation methods to isolate and purify the recombinant protein. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combination thereof.

Pharmaceutical Composition and Methods of Administration

The TCRs of the present invention and T cells transfected with TCRs of the present invention may be provided in a pharmaceutical composition together with a pharmaceutically acceptable carrier. The TCRs, multivalent TCR complexes and cells of the present invention will usually be supplied as part of sterile pharmaceutical composition which will normally include a pharmaceutically acceptable carrier. The pharmaceutical composition can be in any appropriate forms (depending upon the desired method of administering to a patient). It can be provided in unit dosage form, will generally be provided in a sealed container, and can be provided as part of a kit. The kit (although not necessarily) normally includes instructions for use. It may include a plurality of said unit dosage forms.

In addition, the polypeptides of the present invention may be used alone, or associating or coupling with other therapeutic agents (e.g., those formulated in the same pharmaceutical composition).

Therapeutic agents that can be associated with or coupled with the TCRs of the present invention include, but are not limited to: 1. Radioactive nuclide (Koppe, et al, 2005, *Cancer metastasis reviews* 24, 539); 2. Biological toxin (Chaudhary et al, 1989, Nature, 339, 394; Epel et al, 2002, *Cancer immunology and immunotherapy* 51,565); 3. Cytokine (Gillies, et al, 1992, PNAS, 89,1428; Card, et al, 2004, *Cancer immunology and immunotherapy* 53, 345; Halin, et al, 2003, *Cancer research* 63, 3202); 4. Antibody Fc fragment (Mosquera et al, 2005, *The journal of immunology* 174, 4381); 5. Antibody scFv (Zhu, et al, 1995, *International journal of cancer* 62, 319); 6. Gold nanoparticle/nano-rod (Lapotko, et al, 2005, *Cancer letters* 239, 36; Huang, et al, 2006, *Journal of the American chemical society* 128, 2115); 7. Virus particles (Peng, et al, 2004, *Gene therapy*, 11, 1234); 8. Liposome (Mamot, et al, 2005, *Cancer research* 65,11631); 9. Magnetic nano-particles; 10. Prodrug activating enzymes (such as DT-diaphorase (DTD) or Biphenyl hydrolase-like protein (BPHL)); 11. Chemotherapeutic agent (e.g., cisplatin), and the like.

The pharmaceutical composition can further comprise a pharmaceutically acceptable carrier. The term "pharmaceutically acceptable carrier" refers to the carrier for using in administering the therapeutic agents. The term refers to such medical carriers that they themselves do not induce antibody deleterious to the subject having been administered the composition, and they do not have excessive toxicity after administration. These carriers are well known by the skilled person in the art. The detailed discussion about the pharmaceutically acceptable excipient can be found in Remington's Pharmaceutical Sciences (Mack Pub. Co., N.J., 1991). Such carriers include, but are not limited to, saline, buffer solution, glucose, water, glycerin, ethanol, adjuvant or the combination thereof.

The pharmaceutically acceptable carrier in the therapeutic composition can comprise liquid, such as water, saline, glycerin, and ethanol. Further, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulated, the composition of the present invention can be administered via conventional routes which include, but are not limited to, administering intra-ocularly, intramuscularly, intravenously, subcutaneously, intracutaneously or topically. The subject to be prevented or treated may be an animal, especially a human.

When the pharmaceutical composition of the present invention is used in the actual treatment, the dosage form of the pharmaceutical composition can be varied according to the uses. Preferably, as an example, the dosage form may include injection, oral formulation, etc.

The pharmaceutical composition can be formulated by mixing, diluting or dissolving according to the conventional methods. And, occasionally, suitable medical additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulation can be carried out in a conventional manner according to the dosage form.

The pharmaceutical composition of the present invention can further be administered in a form of sustained release formulation. For example, the peptide of the present invention can be incorporated into the pill or microcapsule in which a sustained release polymer is used as carrier, and then the pill or microcapsule is implanted into the tissue to be treated by operation. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc. Preferable examples include the biodegradable polymers, such as polymer of lactic acid, and lactic acid-glycolic acid copolymer.

When the pharmaceutical composition of the present invention is used in the actual treatment, the dose of the peptide the present invention or a pharmaceutically acceptable salt thereof, as an active ingredient, can be suitably determined according to the body weight, age, sex, symptom of each patient.

Use of TCR of Invention

The TCR of the present invention can be used as a drug or a diagnostic agent. The features which are suitable for use as a drug or a diagnostic agent can be obtained by modifications or other improvements. Such drugs or diagnostic agents may be used for treatment or diagnosis of various diseases, including but not limited to cancer (such as renal cancer, ovarian cancer, head and neck cancer, testicular cancer, lung cancer, gastric cancer, cervical cancer, bladder cancer, prostatic carcinomas or melanomas), autoimmune disease, viral infection disease, graft rejection and graft-versus-host disease.

Drug localization or targeted drug delivery can be realized based on specificity of the TCR of invention, thereby enhancing therapeutic or diagnostic effects of various diseases.

For cancer, the localization in the vicinity of tumors or metastasis can enhance the effect of toxins or immunostimulants. In autoimmune diseases, immunoreaction to normal cells or tissues can be inhibited specifically, or immunosuppressive drugs can be released slowly to get more local effect over a longer time-span while minimally affecting the overall immuno-capacity of the subject. In the prevention of transplant rejection, the effect of immunosuppression can be optimized in the same way. For viral diseases for which medicines exist, for example HIV, SIV, EBV, CMV, HCV, HBV, it is beneficial that the medicine is released or plays activation function in vicinity of infected cells.

TCRs of the invention can be used to modulate T cell activation by binding to specific pMHC and thereby inhibiting T cell activation. This approach may apply to autoimmune diseases involving T cell-mediated inflammation and/or tissue damage, for example type I diabetes.

TCRs of the invention can also be used for delivering cytotoxic agents to tumor cells, or can be transformed into T cells, thus rendering them a capability of damaging tumor cells presenting HLA complexes so that they can be administrated to a patient in a treatment process termed adoptive immunotherapy.

TCRs of invention can also be used as a therapeutic agent. TCRs of invention can be labeled with a detectable label, for example a label which is suitable for diagnostic purpose, for detecting binding of a MHC-peptide to a TCR of the invention which is specific for the MHC-peptide. A fluorescently-labeled multimeric TCR is suitable for use in FACS analysis to detect antigen presenting cells carrying a peptide to which the TCR is specific.

The TCR of the present invention bound to a conjugate (the conjugate including but not limited to an anti-CD3 antibody) can re-direct T cells so that T cells are targeted to cells presenting specific antigen, such as cancer cells.

Industrial Applicability

The high-stability TCR of the present invention is useful not only in the study of the interaction between TCR and pMHC (peptide-major histocompatibility complex) but also in diagnosis and treatment of diseases.

The main advantages of the present invention comprise:

(a) The TCR polypeptides of the present invention have high stability.

(b) The high-stability TCR polypeptides can be screened out efficiently and conveniently.

(c) The high-stability and high-affinity TCR polypeptides can be further screened out.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook and Russell et al., Molecular Cloning—A Laboratory Manual (3$^{rd}$ Ed) CSHL Press), or according to the manufacture's instructions. Unless indicated otherwise, parts and percentage are calculated by weight.

EXAMPLE 1

Construction and Sequence Optimization of Initial Single-chain TCR Variable Domain (sTv)

For site-directed mutation of synthetic TCR α and β chain variable domain amino acid sequence (see WO2012/013913), the primers showed in Table 1 were designed. Due to these mutations, the hydrophobic residues located on surface of TCR α and β chain variable domain framework were mutated into hydrophilic or polar residues in order to prepare templates for hydrophobic core mutation libraries. The mutation of a surface hydrophobic residue V at position 20 of α chain into a hydrophilic residue S was completed by directed mutagenesis during the construction of hydrophobic core mutant library.

TABLE 1

Primers and linkers used for the site-directed mutation of amino acid sequence

| Primer Name | Primer Sequence (from 5' to 3') | SEQ ID NO: |
|---|---|---|
| YW800 | aacaggagtgacgcagtctccttcatctgtgagtg | 1 |
| YW801 | ttagcgccatggcccaaaaacaggaggtgacgcagtc | 2 |
| YW802 | gaatcttctcagcccggggac | 3 |
| YW803 | cgggctgagaagattcaatg | 4 |
| YW804 | gccaccgccagatccaccgggccctggagtgaccgag | 5 |
| YW805 | gtggatctggcggtggcggtgaaggcggtggtggaag cggcggcggaggcgaaggaggctccggag | 6 |
| YW806 | gcgaaggaggctccggaggcaaggctggagtcactcaaac | 7 |
| YW807 | ctagatgcggccgcctctgtgaccgtgagcctg | 8 |

YW800, YW801, YW802, YW803 and YW804 were primers designed for site-directed mutation of α chain variable domain; YW806 and YW807 were primers designed for site-directed mutation of β chain variable domain; and YW805 was a linker used for introducing a flexible peptide fragment. sTv was constructed by PCR carried out according to the primer ligation manner as shown in FIG. 4, and this sTv was named as MAGE-sTv-WT.

Specific PCR mutagenesis steps were as follows:

The first step of PCR. PCR was implemented by using a synthetic α or β strand as template respectively and the following primer pairs: YW801/YW803 (α chain), YW802/YW804 (α chain), YW806/YW807 (β chain). The reaction procedure was: 98☐ denaturation for 30 seconds, once; and 94☐ for 5 seconds, 55☐ for 10 seconds, and 72 ☐ for 20 seconds, totally 25 cycles.

The second step of PCR. The overlap PCR method was implemented in the second step of PCR by using the purified product of the first step PCR and chemical synthetic single-stranded DNA encoding the flexible peptide fragment as templates and YW800/YW807 as primers. The reaction procedure was: 98☐ denaturation for 30 seconds, once; 94☐ for 5 seconds, 55☐ for 10 seconds, 72 ☐ for 30 seconds, totally 30 cycles; and 72 ☐ for 5 minutes, once. The product of the second step of PCR was purified, digested and ligated into a phage display vector.

EXAMPLE 2

Cloning of MAGE-sTv-WT Sequence into pET-28a-based Expression Plasmid

The MAGE-sTv-WT was cloned into a pET-28a-based expression plasmid by standard methods described in *Molecular Cloning: a Laboratory Manual* (Third edition by Sambrook and Russell). Plasmid was sequenced using an 3730 DNA Analyzer from ABI.

The DNA sequence encoding the MAGE-sTv-WT digested with Nco☐ and Nco☐ was ligated into a pET-28a vector (Novagen).

The ligated plasmid was transformed into competent *Escherichia coli* strain BL21(DE3) cells (Purchased from Merck) and plated out on LB/agar plates containing 50 μg/mL kanamycin. After incubation overnight at 37☐, single colony was picked and grown in 5 ml LB containing 50 μg/mL kanamycin overnight at 37☐ with shaking. Cloned plasmid was purified using a Zyppy Plasmid Midiprep Kit from Zymo (Zyppy Plasmid Midiprep Kit, Zymo) and the insert was sequenced using an 3730 DNA sequencer from ABI.

FIGS. 2a and 3a respectively show amino acid sequence of α and β chain variable domains of MAGE-sTv-WT (SEQ ID NOs: 9 and 11), and the optimized amino acid residues are shown in bold and underlined. FIGS. 2b and 3b respectively show nucleotide sequence of α and β chain variable domains of MAGE-sTv-WT (SEQ ID NOs: 10 and 12).

EXAMPLE 3

Expression, Renaturation and Purification of MAGE-sTv-WT

The expression plasmid containing MAGE-sTv-WT was transformed into E. coli strain Rosetta (DE3) (Merck) on a plate of culture medium. After cultured at 37☐ overnight, single colony was picked up and cultured at 37☐ in medium containing kanamycin until $OD_{600}$ was 0.6-0.8. Then protein expression was induced with 0.5 mM IPTG for 4 h. Cells were harvested by centrifugation at 5000 rpm for 15 minutes using a FisherThermo Sovall R6+ centrifuge. Cell sediment was lysed with Bugbuster MasterMix (Merck). Inclusion body sediment was recovered after centrifugation at 6,000 g for 15 minutes using a FisherThermo Sovall X1R centrifuge. Inclusion body was washed 3 times with Bugbuster solution (10-fold dilution) to remove cell debris and membrane components. Then the inclusion body was dissolved in the following buffer: 20 mM Tris, pH 9.0, 8M urea. It was divided into 10 mg aliquots per tube after quantitation using BCA method and frozen at −80☐.

10 mg of solubilized MAGE-sTv-WT inclusion body protein was thawed, added into 200 ml of a renaturation buffer containing 100 mM Tris, pH9.0, 400 mM L-Arginine, and 2 mM EDTA. The oxidized and reduced glutathione redox couple were added into solution to final concentrations of 1 mM and 10 mM, respectively. The solution was stirred for 10 minutes at 10☐, and shaking for 1-2 days at 100 rpm. The renatured MAGE-sTv-WT was dialyzed using a cellulose membrane dialysis bag with a molecular weight cut-off of 4 kD and 5 L 20 mM Tris (pH 9.0) at 4-8☐ for 8 hours. The dialysis buffer was replaced with fresh buffer twice.

After centrifugation, the dialyzed and renatured MAGE-sTv-WT was loaded onto a Q HP anion exchange column (GE, 5 ml) and the bound proteins were eluted with a linear gradient of 0-1M NaCl prepared with 20 mM Tris pH 9.0 for 10 column volumes using an AKTA purifier (GE). The eluted peak (at a relative molecular weight of approximately 28 kD) was collected and then analyzed by SDS-PAGE (Bio-Rad). The component comprising MAGE-sTv-WT was concentrated and further purified by gel filtration column (Superdex 75 10/300, GE Healthcare). If the target component was obtained after purification, the target component was analyzed by SDS-PAGE and then stored at 4☐. The target peak components were pooled and concentrated, and then exchanged into a HEPES buffer (10 mM, pH 7.4).

The eluted fractions were further tested for purity by gel filtration method. Conditions: Columns Agilent Bio SEC-3 (300 A, φ7.8×300 mm), a mobile phase of 150 mM phosphate buffer, a flow rate of 0.5 mL/min, column temperature of 25☐, and UV detection wavelength at 214 nm.

EXAMPLE 4

Generation of High-stability Variants of MAGE-sTv-WT

Phage display was used to form a library of MAGE-sTv-WT hydrophobic core variants, which was used for screening and identifying high-stability mutants. Hydrophobic core sites of MAGE-sTv-WT were mutated to construct the hydrophobic core mutant library, and the library was panned and screened. The hydrophobic core library construction and screening method were referred to Li et al ((2005) Nature Biotech 23 (3): 349-354) which described phage display and high affinity TCR phage library construction and screening method. The difference was that when a hydrophobic core mutant library was constructed, primers should be designed according to hydrophobic core site of template strand, while when a high affinity TCR library was constructed, primers was designed based on the CDR regions of template strand. When constructing the hydrophobic core mutation library, the designed primers are shown in Table 2 below.

TABLE 2

Primers designed for constructing MAGE-sTv-WT hydrophobic core mutation library

| Primer Name | Primer Sequence (from 5' to 3') | SEQ ID NO: |
|---|---|---|
| YW817 | gttttctccttctgggacac | 19 |
| YW818 | GtcccagaaggagaaaacNTKtctNTKaactgca gtttcactg | 20 |
| YW819 | gtataaagtactacgtcctgatg | 21 |
| YW820 | CaggacgtagtacttatacNTKgaatctt ctcagc | 22 |
| YW821 | ttgctgtcctctcgttttggac | 23 |
| YW822 | CaaaacgagaggacagcaaNTKacaNTKagctgct cccctatc | 24 |
| YW823 | attcatctcagagcgagag | 25 |
| YW824 | CtcgctctgagatgaatNTKagcaccttggagctg | 26 |
| YW825 | gccgcctctgtgaccgtmancctmrkgcccggccc gaagtac | 27 |
| YW826 | acggtcacagaggcggccgcatctagaattc | 28 |

The degenerate bases used in the present invention, as well-known to those skilled in the art, can represent base types as follows: B=C or G or T; D=A or G or T; H=A or C or T; K=G or T; M=A or C; N=A or C or G or T; R=A or G; S=C or G; V=A or C or G; W=A or T; Y=C or T.

For eliminating poor-stability mutant strains and screening out more stable mutant strains in the process of phage display, the following three treatment methods were adopted: 1. displaying sTv at 37 ☐; 2. adding inducer (e.g., IPTG) to induce sTv displayed on surface of phage; 3. incubating phage displaying sTv at 55☐ for 60 minutes before screening.

After identification by sequencing, all of the hydrophobic core of high-stability sTv mutant strains screened out by the above method had mutations. The screened high-stability mutant strains were named as MG29, P8F1 and P8F2. According to the numbering of amino acid position in IMGT, the α chain variable domain had one or more amino acid mutations in hydrophobic core: position 19, position 21, position 91; and/or the β chain variable domain had one or more amino acid mutation in hydrophobic core: position 91, position of 4th from the last of β chain J gene short peptide. More specifically, according to the numbering of amino acid position in IMGT, they had one or more following amino acid residues in α chain variable domain: 19V, 21I, 91L; and/or they had one or more following amino acid residues in β chain variable domain: 91F or 91I, the position of 4th from the last of β chain J gene was M. Specifically, α chain variable domain amino acid sequence was SEQ ID NOs:15 or 17; and β chain variable domain amino acid sequence was SEQ ID NOs:16 or 18. The amino acid sequences of α and β chain variable domain forming mutant stain MG29 were SEQ ID NOs: 15 and 16 respectively, as shown in FIGS. 6a and 6b; the amino acid sequences of α and β chain variable domain forming mutant stain P8F1 were SEQ ID NOs: 17 and 18 respectively, as shown in FIGS. 7a and 7b; and the amino acid sequences of α and β chain variable domain forming mutant stain P8F2 were SEQ ID NOs: 15 and 18 respectively, as shown in FIGS. 8a and 8b.

The above screened-out high-stability mutant stains MG29, P8F1, P8F2 with high OD values and the MAGE-sTv-WT with a non-mutated hydrophobic core were subjected to ELISA experiment to compare OD values, and specificity of mutant strains was verified.

The steps of ELISA experiments:

1. The strains MAGE-sTv-WT, MG 29, P8F1, and P8F2 in glycerol were respectively inoculated into 5 mL 2×TY (100 µg/mL ampicillin, 2% glucose), 250 rpm/min, 37□ overnight.

2. After cultured overnight, 50 µL of broth was respectively inoculated into 5 mL fresh 2×TY (100 µm/mL ampicillin, 2% glucose), 250 rpm/min, and cultured at 37□ until OD600 was 0.4. After infection with 5 µL (6.5×10¹⁰) KM13 helper phage (Source BioScience) and standing at 37□ for 30 min, it was shaken at 200 rpm/min at 37□ for 30 min, and centrifuged. Sediment was re-suspended in 30 mL 2×TY (100 µg/mL ampicillin, 50 µg/mL kanamycin, 0.1% glucose), and cultured at 30□ overnight at 250 rpm/min.

3. Immunosorbent plate (NUNC) was coated with 10 µg/mL streptavidin (PBS, pH=7.4), 100 µL per well, and placed at 4□ overnight.

4. Supernatant of overnight culture broth was collected after centrifugation. Phage in supernatant was precipitated with PEG/NaCl having a volume ratio of 1/4, placed on ice for 1 h, and centrifuged to collect precipitates. The precipitates were re-suspended in 3 mL PBS.

5. The plate was washed with 0.1% TBST for three times, and 400 µL 3% Marvel-PBS (Cadbury Schweppes) was added into each well, and plate was blocked at 37□ for 2 h. The plate was washed with PBST for three times, and 100 µL pMHC of 10 ug/mL was added into each well and the plate was placed at room temperature for 1 h. After washing the plate for three times, 100 µL phage samples (10 µL PEG precipitated sample with 3% Marvel-PBS incubated at room temperature for 1 h) was added into each well, and plate was placed at room temperature for 1 h; after washing the plate for three times, 100 uL anti-M13-HRP conjugate (GE Healthcare) (1:5000 dilution in 3% Marvel-PBS) was added into each well, and the plate was placed at the room temperature for 1 h. The plate was washed for six times and each well was added 100 µL, TMD and placed for 5 min. 100 µL of 1M sulfuric acid was added into each well for termination.

6. Absorbance at 450 nm and 650 nm was read.

OD values of mutant strains in ELISA experiment were shown in FIG. 9 and the result showed that the specificity of sTv having an optimized hydrophobic core optimized is maintained and is the same as that of MAGE-sTv-WT having a wild-type hydrophobic core. In this experiment, the OD value of MAGE-sTv-WT was very low due to poor display, indicating that even if the hydrophobic residues exposed on surface of α chain and β chain variable domain were changed into hydrophilic or polar residues, the protein stability was still relatively poor, and therefore the hydrophobic core was still needed to be optimized. Clones with optimized hydrophobic core could display sTv to different extend and bind specifically to the original ligand MAGE A3 pHLA-A1 antigen, but could not bind to other irrelevant antigens, such as EBV, influenza and NY-ESO-1 antigens. Binding of sTv molecules having a mutated hydrophobic core (MG29, P8F1, P8F2 and the others detected by phage display) to specific antigens was not because they had an affinity stronger than that of wild-type TCR, as proved in Example 15.

EXAMPLE 5

Construction of High-stability sTv Molecules with Hydrophobic Core Mutation

A part of hydrophobic core of high-stability mutant screened out in Example 4 was introduced into several other TCR molecules to build high-stability sTv molecules using the well-known method of directed mutagenesis in the art.

Several above molecules in single-chain form were constructed according to α and β chains variable domains of wild-type TCRs respectively against the antigen short peptides of HLA-B8/FLRGRAYGL (derived from EB virus antigen of EBNA3A), HLA-A2/GILGFVFTL (derived from influenza virus matrix protein) and HLA-A2/SLLMWITQC (NY-ESO-1 tumor specific antigen), and were respectively named as LC13-WT, JM22-WT and 1G4-WT. The amino acid sequences of α chain and β chain variable domain of LC13-WT were SEQ ID NO: 29 and SEQ ID NO: 30 respectively, as shown in FIGS. 10a and 10b; the amino acid sequences of α chain and β chain variable domain of JM22-WT were SEQ ID NO:31 and SEQ ID NO: 32 respectively, as shown in FIGS. 11a and 11b; and the amino acid sequences of a chain and β chain variable domain of 1G4-WT were SEQ ID NO:33 and SEQ ID NO: 34 respectively, as shown in FIGS. 12a and 12b.

A part of hydrophobic core of high-stability variant screened out in Example 4 was respectively introduced to LC13-WT, JM22-WT and 1G4-WT according to the well-known method of directed mutagenesis in the art. Molecules obtained after introduction of mutation were respectively named as LC13-sTv, JM22-sTv and 1G4-sTv and the hydrophobic core introduced were shown in bold and underlined. The amino acid sequences of α chain and β chain variable domain of LC13-sTv were SEQ ID NO: 35 and SEQ ID NO: 36 respectively, as shown in FIGS. 13a and 13b and the hydrophobic core introduced in α chain comprised 11L, 13V, 21I and 91I and the hydrophobic core introduced in β chain comprised 94L. The amino acid sequences of α chain and β chain variable domain of JM22-sTv were SEQ ID NO:37 and SEQ ID NO: 38 respectively, as shown in FIGS. 14a and 14b and the hydrophobic core introduced in α chain comprised 19V and 21I and the hydrophobic core introduced in β chain comprised 91I and 94L. The amino acid sequences of α chain and β chain variable domain of 1G4-sTv were SEQ ID NO:39 and SEQ ID NO: 40 respectively, as shown in FIGS. 15a and 15b and the hydrophobic core introduced in α chain comprised 19V and 21I and the hydrophobic core introduced in β chain comprised 19V, 91I, and 94L and the position of 6th from the last of J gene was T. The above numbering of amino acid position was the numbering shown in IMGT. A short peptide for linkage (linker) useful in construction of above single-chain molecules could be any suitable sequence and the preferred amino acid sequence in the present invention was SEQ ID NO: 41, as shown in FIG. 16.

EXAMPLE 6

Stability Test of Protein LC13-WT and LC13-sTv

Using the method described in Example 3, proteins of LC13-WT and LC13-sTv were expressed, refolded, and purified. After gel filtration column purification, a SDS-PAGE gel was run and SEC profiles of two proteins were made using gel filtration. The expression quantity, purified protein quantity and protein refolding yield were calculated at the same time. Among them, the expression quantity was the yield of the purified inclusion body inductively expressed in 1L *E. coli.* broth. The purified protein quantity was the quantity of protein obtained after purification of refolded inclusion body which was purified from the inclusion body inductively expressed by 1L *E. coli.* broth. Calculation formula of protein refolding yield was: protein refolding yield (%)=100*purified protein quantity (mg)/ inclusion body quantity used in refolding (mg). In the present invention, the expression quantity and the protein refolding yield were calculated according to the above calculation method unless indicated otherwise.

The Tm value of purified proteins of LC13-WT and LC13-sTv were measured with differential scanning calorimeter (Nano DSC) of US TA company (Waters). Scanning range was 10-90□, heating rate was 1□/min, and the sample volume was 900pL. The Tm value was obtained by using the fitting model of TwostateScaled in software Nanoanalyze.

Table 3 showed the data of the expression quantity, purified protein quantity and protein refolding yield of LC13-WT and LC13-sTv.

TABLE 3

| Protein name | Expression quantity(mg/L) | Purified protein quantity(mg/L) | Yield(%) |
| --- | --- | --- | --- |
| LC13-WT | 231 | 1.3 | 0.56% |
| LC13-sTv | 330 | 66.6 | 20.2% |

The data of above table showed that, after purification, the protein refolding yield of LC13-sTv having introduced in hydrophobic core was increased by 35 folds compared with that of LC13-WT protein having no mutation in hydrophobic core.

FIG. 17 shows the SDS-PAGE gel results of proteins of LC13-WT and LC13-sTv purified by a gel filtration column (Superdex 75 10/300, GE Healthcare) according to Example 3. The gel photo showed that the band formed by purified LC13-WT protein was heterogeneous, and LC13-sTv formed a single band and had a high purity. It suggested that the refolding of LC13-sTv was much better than that of LC13-WT.

FIGS. 18a and 18b respectively show SEC profiles of purified proteins LC13-WT and LC13-sTv. As shown, the purified protein LC13-WT showed no peak, while LC13-sTv formed a single and symmetrical elution peak. It suggested that the refolding of LC13-sTv was significantly better than that of LC13-WT.

The protein with correct conformation obtained from LC13-WT refolding was very little and there was no apparent endothermic peak of protein unfolding. The Tm value of LC13-WT could not be detected by using analyzing software Nanoanalyze. While the Tm value of LC13-sTv with hydrophobic core mutations was 43.6□ and its DSC graph was shown in FIG. 47. It suggested that compared with LC13-WT, LC13-sTv had a stronger renaturability, was more resistant to unfolding, was more resistant to inappropriate or undesired folding, and had a significantly improved thermal stability.

After comparative analysis of the expression quantity, the purified protein quantity, the protein refolding yield, SDS-PAGE gel maps, SEC profiles and Tm values of the proteins of LC13-WT and LC13-sTv, it could be seen that compared to LC13-WT having a non-modified hydrophobic core, LC13-sTv having a modified hydrophobic core had a stronger renaturability, was more resistant to unfolding, was more resistant to inappropriate or undesired folding, had a higher protein refolding yield and had a significantly improved thermal stability. Thus, compared to LC13-WT, LC13-sTv had a significantly improved stability. In the present invention, the stability of LC13-sTv was increased by 35 folds relative to the stability of LC13-WT calculated based on data of protein refolding yield.

EXAMPLE 7

Stability Test of Protein JM22-WT and JM22-sTv

Using the method described in Example 3, proteins of JM22-WT and JM22-sTv were expressed, refolded, and purified. After gel filtration column purification, a SDS-PAGE gel was run and SEC profiles of two proteins were made using gel filtration. The expression quantity, purified protein quantity and protein refolding yield were calculated at the same time. The Tm values were determined using the method in Example 6.

Table 4 showed the data of the expression quantity, purified protein quantity and protein refolding yield of JM22-WT and JM22-sTv.

TABLE 4

| Protein name | Expression quantity(mg/L) | Purified protein quantity(mg/L) | Yield(%) |
| --- | --- | --- | --- |
| JM22-WT | 152 | 0.67 | 0.4% |
| JM22-sTv | 350 | 60.04 | 17.2% |

The data of above table showed that, after purification, the protein refolding yield of JM22-sTv having mutations introduced in hydrophobic core was increased by 42 folds compared with that of JM22-WT protein having no mutation in hydrophobic core.

FIG. 19 shows the SDS-PAGE gel results of proteins of JM22-WT and JM22-sTv purified by a gel filtration column (Superdex 75 10/300, GE Healthcare) according to Example 3. The gel photo showed that the monomer bands formed by refolded JM22-WT protein was heterogeneous and there were three bands, and JM22-sTv formed a single band of monomer with a high purity. It suggested that the refolding of JM22-sTv was much better than that of JM22-WT.

FIGS. 20a and 20b respectively show SEC profiles of purified proteins JM22-WT and JM22-sTv. As shown, the elution peak formed by purified protein JM22-WT was not unitary and the signal was very low, while purified LC13-sTv formed a unitary and symmetrical elution peak. It suggested that the refolding of JM22-sTv was significantly better than that of JM22-WT.

FIGS. 48a and 48b respectively show DSC graphs of purified protein JM22-WT and JM22-sTv. The protein with correct conformation obtained from JM22-WT refolding was very little and there was no apparent endothermic peak of protein unfolding. The Tm value of JM22-WT could not be detected by using analyzing software Nanoanalyze. While the Tm value of JM22-sTv with hydrophobic core mutations was 43.7☐. The above DSC graph showed that compared with JM22-WT, JM22-sTv had a stronger renaturability, was more resistant to unfolding, was more resistant to inappropriate or undesired folding, and had a significantly improved thermal stability.

After comparative analysis of the expression quantity, the purified protein quantity, the protein refolding yield, SDS-PAGE gel maps, DSC graphs, and SEC profiles of the proteins of JM22-WT and JM22-sTv, it could be seen that compared to JM22-WT having a non-modified hydrophobic core, JM22-sTv having a modified hydrophobic core had a stronger renaturability, was more resistant to unfolding, was more resistant to inappropriate or undesired folding, had a higher protein refolding yield and had a significantly improved thermal stability. Thus, compared to JM22-WT, JM22-sTv had a significantly improved stability. In the present invention, the stability of JM22-sTv was increased by 4200% relative to the stability of JM22-WT calculated based on data of protein refolding yield.

EXAMPLE 8

Stability Test of Protein 1G4-WT and 1G4-sTv

Using the method described in Example 3, proteins of 1 G4-WT and 1 G4-sTv were expressed, refolded, and purified. After gel filtration column purification, a SDS-PAGE gel was run and SEC profiles of two proteins were made using method of gel filtration. The expression quantity, purified protein quantity and protein refolding yield were calculated at the same time.

Table 5 showed the data of the expression quantity, purified protein quantity and protein refolding yield of 1G4-WT and 1G4-sTv.

TABLE 5

| Protein name | Expression quantity(mg/L) | Purified protein quantity(mg/L) | Yield(%) |
| --- | --- | --- | --- |
| 1G4-WT | 290 | 8.08 | 2.8% |
| 1G4-sTv | 388 | 38.8 | 10% |

The data of above table showed that, after purification, the protein refolding yield of 1G4-sTv having mutations introduced in hydrophobic core was increased by 2.6 folds compared with that of 1 G4-WT protein having no mutation in hydrophobic core.

FIG. 21 shows the SDS-PAGE gel results of proteins of 1G4-WT and 1G4-sTv purified by a gel filtration column (Superdex 75 10/300, GE Healthcare) according to Example 3. The gel photo showed that the bands formed by purified 1G4-WT protein was heterogeneous and there were two bands, and 1 G4-sTv formed a single band of monomer with a high purity. It suggested that the refolding of 1 G4-sTv was much better than that of 1 G4-WT.

FIGS. 22a and 22b respectively show SEC profiles of purified proteins 1G4-WT and 1G4-sTv. As shown, the elution peak formed by purified protein 1G4-WT was not unitary and the signal was very low, while purified 1 G4-sTv formed a unitary and symmetrical elution peak. It suggested that the refolding of 1 G4-sTv was significantly better than that of 1 G4-WT.

After comparative analysis of the expression quantity, the purified protein quantity, the protein refolding yield, SDS-PAGE gel maps, and SEC profiles of the proteins of 1G4-WT and 1 G4-sTv, it could be seen that compared to 1 G4-WT having a non-modified hydrophobic core, 1 G4-sTv having a modified hydrophobic core had a stronger renaturability, a higher expression quantity, and a higher protein refolding yield. Thus, compared to 1G4-WT, 1G4-sTv had a significantly improved stability. In the present invention, the stability of 1G4-sTv was increased by 260% relative to the stability of 1G4-WT calculated based on data of protein refolding yield.

EXAMPLE 9

Further Optimization of Stability of Molecules Using 1G4-sTv as a Template

Using 1G4-sTv as a template, its hydrophobic core and surface amino acid residues in variable domain were mutated to construct a library for screening high stability molecules. Hydrophobic core sites to be mutated were shown in sequence of SEQ ID NO: 42 which were in bold and underlined. The surface amino acid residues to be mutated were marked in bold as shown in FIG. 23.

The basic method used for library construction was already described in Example 4. In this example, three libraries were constructed for sites to be mutated. All of the hydrophobic core sites to be mutated were in Library 1. Library 2 and library 3 were constructed for surface amino acid residues. More particularly, an overlap PCR was implemented using 1G4-sTv plasmid as a template and mutation primers designed so as to obtain mutant DNA fragments. The mutant DNA fragments were digested by NcoI/NotI and fragments were cloned into a phage plasmid vector pLitmus28 (NEB) based on pUC19 backbone. After electrotransfecting DNA into TG1 competent cells (Lucigen), a total of three phage plasmid vector libraries were obtained whose capacity were $1 \times 10^9$-$3 \times 10^9$ based on number of colonies. The lawn grown in these three libraries was scraped, added into glycerol with a final concentration of 20% and stored at −80☐. The following Tables 8, 9 and 10 respectively showed primers designed for Library 1, Library 2 and Library 3.

TABLE 6

| Primers designed for constructing Library 1 | | |
| --- | --- | --- |
| Primer Name | Primer Sequence from 5' to 3' | SEQ ID NO: |
| L1-01 | CCGGCCATGGCCAAGCAGGAANTKACGCAATCCCC GTCGTC | 43 |
| L1-02 | AATCCCCGTCGTCAVDGTCTVDGCCGGAAGGCGAA AATGTC | 44 |

TABLE 6-continued

Primers designed for constructing Library 1

| Primer Name | Primer Sequence from 5' to 3' | SEQ ID NO: |
|---|---|---|
| L1-03 | TCGCGGAGTCACCCGGCTGMANTGATTCAATATACAGG | 45 |
| L1-04 | CAGCCGGGTGACTCCGCGACGTACTTTTGTG | 46 |
| L1-05 | TTCGGCGTTTGGGTMANACCCGCATTAC | 47 |
| L1-06 | ACCCAAACGCCGAAATACVDGAGCVDGAAGACGGGTCAGTC | 48 |
| L1-07 | GCGGAGTCACTCGGGGTMANTGATTCAATGC | 49 |
| L1-08 | ACCCCGAGTGACTCCGCADBGTATCTGTGTGCTTCG | 50 |
| L1-09 | TCGAGTGCGGCCGCCGTCACCGTCA | 51 |

TABLE 7

Primers designed for constructing Library 2

| Primer Name | Primer Sequence from 5' to 3' | SEQ ID NO: |
|---|---|---|
| L2-01 | AGCCGGCCATGGCCAAGCAGGAAGTCAC | 52 |
| L2-02 | GATTGAGACATTTTCMYYTTCCGGGACAG | 53 |
| L2-03 | GTCACTGTCTGTCCCGGAARRKGAAAATGTCTCAATC | 54 |
| L2-04 | CACAAAAGTACGTCGCMYYGTCMYYCGGCTGCGATGAT | 55 |
| L2-05 | CGACGTACTTTTGTGCGGTTCGTCC | 56 |
| L2-06 | CAGCTTCGTACCCTTGCCGAAGGTC | 57 |
| L2-07 | TTCGGCAAGGGTACGAAGCTGRRKGTCACGCC | 58 |
| L2-08 | CATTGCAGGGTCACMYYCTGMYYCGTMYYCAGGCTCTGGT | 59 |
| L2-09 | GTGACCCTGCAATGCGCCCAGGATATG | 60 |
| L2-10 | CACAGATAAACTGCGGAGTCMYYCGGGGTCAG | 61 |
| L2-11 | GACTCCGCAGTTTATCTGTGTGCTTCGTCC | 62 |
| L2-12 | GAGTGCGGCCGCCGTCACMYYCAGGCGCGTG | 63 |

TABLE 8

Primers designed for constructing Library 3

| Primer Name | Primer Sequence from 5' to 3' | SEQ ID NO: |
|---|---|---|
| L3-01 | CCGGCCATGGCCAAGCAGGAAGTCACGCAATCCCCGTCGTC | 64 |
| L3-02 | ACGCAATCCCCGTCGTCACTGRRKGTCCCGGAAGG | 65 |
| L3-03 | GGAGTCACCCGGCTGMANMYYTTCAATATACAGGGTAC | 66 |
| L3-04 | CAGCCGGGTGACTCCRRKACGTACTTTTGTGCG | 67 |
| L3-05 | TTCGCTGCCGCCCCCMYYCGTGACGCTCAGCTT | 68 |
| L3-06 | AAGCTGAGCGTCACGRRKGGGGCGGCAGC | 69 |
| L3-07 | GCATTGCAGGGTCACAGACTGACCMYYCTTCAGGCTC | 70 |
| L3-08 | GTCAGTCTGTGACCCTGCAATGCGCCCAGGATATG | 71 |

TABLE 8-continued

Primers designed for constructing Library 3

| Primer Name | Primer Sequence from 5' to 3' | SEQ ID NO: |
|---|---|---|
| L3-09 | CTGCGGAGTCACTCGGMYYCAGMYYTTCAATGCG | 72 |
| L3-10 | CCGAGTGACTCCGCAGTTTATCTGTGTGCTTCGTCC | 73 |
| L3-11 | AGTGCGGCCGCMYYCACCGTCAG | 74 |

In order to obtain high-stability sTv clones, phages grown in libraries were subjected to 65□ heat shock treatment after precipitation and concentration, and co-incubated with 0.02% SDS added for further increasing strength of screening. Then, the treated phage was subjected to follow-up screening. Clones with higher OD value and screened out from three libraries were combined and 11 clones were finally obtained.

EXAMPLE 10

Stability Verification of Clones Screened in Example 9

The OD values of 11 clones screened out in Example 9 were detected by ELISA whose experimental procedure was described in Example 4 and the antigenic specificity thereof was verified. The results were shown in FIG. 24. This results showed that the OD values of 11 clones were high and they could specifically bind to their original ligand antigen of HLA-A2/SLLMWITQC (NY-ESO-1 tumor-specific antigen), and substantially not bind to other irrelevant antigens. Binding of sTv molecules detected by phage display to antigen HLA-A2/LLMWITQC was not because they had an affinity stronger than that of wild-type TCR, as proved in Example 11.

According to the numbering of amino acid position in IMGT, the above 11 clones had one or more mutations in hydrophobic core positions selected from the group consisting of: position 11, position 13, or position 94 of α chain variable domain; and/or position 11, position 13, or position 94 of β chain variable domain. Specifically, they had one or more following hydrophobic core amino acid residues in α chain variable domain: 11M, 11E, 13R, 13K, 94V or 94I; and/or hydrophobic core amino acid residues in β chain variable domain: 11L, 11V, 13V or 94V. In addition to the hydrophobic core, the clones that we screened our further comprised one or more following amino acid residues in α chain variable domain: 4L, 12N, 16S, 93N, 93R, 97N, 100G, 105S or the last position of α chain J gene being D and/or comprised one or more following amino acid residues in β chain variable domain: 4I, 101L, or the last position of β chain J gene being D or the position of 3rd from the last of β chain J gene being E.

Amino acid sequences of α chain variable domain (SEQ ID NOs: 75-85) and amino acid sequence of β chain variable domain (SEQ ID NOs: 86-96) of the above high-stability clones screened out were respectively shown in FIG. 25 and FIG. 26.

Using the methods described in Example 2 and Example 3, each of 11 clones screened was linked, expressed, refolded, and purified. The Tm values of above 11 clones were measured using differential scanning calorimeter (Nano DSC) of US TA company (Waters). Scanning range was 10-90□, heating rate was 1□/min, and the sample volume was 900 μL. The Tm value was obtained by using the fitting model of TwostateScaled of analyzing software Nanoanalyze. The results were shown in FIG. 27 and Table 9, which showed that their Tm values were all not less than 37.9□, and they had apparent endothermic peak of protein unfolding. The DSC results of 1G4-WT were shown in FIG. 28, wherein the expression, refolding, purification processes and DSC experimental conditions were same as those for above clones. It could be seen from the figure that no apparent endothermic peak was showed, indicating that the protein with correct conformation was very little. Compared the DSC graphs of the above 11 clones with the DSC graph of 1G4-WT, it showed that the screened clones were more resistant to unfolding, were more resistant to inappropriate or undesired folding, had a stronger renaturability, and had a significantly improved thermal stability compared with 1G4-WT. Therefore, the stability of screened clones was much higher than that of 1G4-WT without hydrophobic core mutations.

The Tm value could not be obtained by software since the above 1 G4-WT with correct conformation after refolding and purification was very little and had no apparent protein unfolding endothermic peak. While above TCR with mutated hydrophobic core had Tm values of about 38□ or higher, suggesting that stability of 11 mutated TCRs of the above G3-G7 and G9-G14 in the present invention had a very significant increase (at least 1-fold of increase).

TABLE 9

| Clone Name | Amino acid sequences of α and β chain variable domain | | Tm(□) |
|---|---|---|---|
| | α | β | |
| G3 | 75 | 86 | 37.90 |
| G4 | 76 | 87 | 48.22 |
| G5 | 77 | 88 | 41.89 |
| G6 | 78 | 89 | 48.30 |
| G7 | 79 | 90 | 43.33 |
| G9 | 80 | 91 | 49.55 |
| G10 | 81 | 92 | 40.01 |
| G11 | 82 | 93 | 46.57 |
| G12 | 83 | 94 | 44.32 |
| G13 | 84 | 95 | 49.63 |
| G14 | 85 | 96 | 47.70 |

The skilled in the art could reassemble the above screened high-stability mutations to build new stable mutants. We reassembled the above mutation sites to build a new α chain variable domain (SEQ ID NO: 97) and β chain variable domain (SEQ ID NO: 98), whose amino acid sequences were shown in FIGS. 29a and 29b, respectively. The sTv molecules constructed with said a chain variable domain and β chain variable domain was named G15.

EXAMPLE 11

Further Test of Stability of 1G4-WT Mutants

Using the method described in Example 3, mutants of G9, G13 and G15 of example 10 were expressed, refolded, and purified. After gel filtration column purification, a SDS-PAGE gel was run and SEC profiles of three proteins were made using method of gel filtration. The expression quantity, purified protein quantity and protein refolding yield were calculated at the same time and were compared with 1 G4-WT.

Table 10 showed data of the expression quantity, purified protein quantity and protein refolding yield of 1G4-WT, G9, G13 and G15.

TABLE 10

| Protein name | Expression quantity(mg/L) | Purified protein quantity(mg/L) | Yield(%) |
|---|---|---|---|
| 1G4-WT | 290 | 8.08 | 2.8% |
| G9 | 356 | 55.18 | 15.5% |
| G13 | 223 | 101.15 | 45.4% |
| G15 | 279 | 129.7 | 46.5% |

The data of above table showed that, after purification, the protein refolding yield of mutants G9, G13 and G15 had a very significant increase compared with that of 1G4-WT and was respectively increased by 4.5 folds, 15.2 folds, and 15.6 folds.

FIG. 30 shows the SDS-PAGE gel results of proteins 1G4-WT, G9, G13 and G15 purified by a gel filtration column (Superdex 75 10/300, GE Healthcare) as described in Example 3. The gel photo showed that the band formed by refolded 1G4-WT protein was heterogeneous, and G9, G13 and G15 formed a single band of monomer with high purity. It suggested that the refolding of G9, G13 and G15 was better than that of 1 G4-WT.

FIGS. 31a, 31b and 31c show respectively SEC profiles of proteins G9, G13 and G15. As shown in FIG. 22a of SEC profile of 1G4-WT, the elution peak formed by purified protein 1G4-WT was not unitary and the signal was very low, while purified G9, G13 and G15 formed a unitary and symmetrical elution peak. It suggested that the refolding of G9, G13 and G15 were significantly better than that of 1G4-WT.

The Tm value of G15 measured using the method in Example 10 was 46.6□, and its DSC curve was shown in FIG. 46. According to the results measured as in Example 10, the Tm values of mutant strains G9 and G13 were relatively high and were 49.55□ and 49.63□, respectively.

Binding of proteins G9, G13 and G15 to ligands thereof was detected with BIAcore T200 real-time analysis system. The result showed that affinity of three sTv proteins to antigen HLA-A2/SLLMWITQC was not better than the binding of wild-type 1 G4 TCR to the antigen. The dissociation equilibrium constant of wild-type 1G4 TCR binding with antigen HLA-A2/SLLMWITQC was 32 μM (referring to Li et al ((2005) Nature Biotech 23 (3): 349-354)).

After comparative analysis of the expression quantity, the purified protein quantity, the protein refolding yield, SDS-PAGE gel maps, and SEC profiles of the proteins of 1G4-WT and G9, G13 and G15, it could be seen that the renaturability, thermal stability, and protein refolding yield of mutants having modified hydrophobic core were much higher than those of 1G4-WT having non-modified hydrophobic core. Thus, compared to 1G4-WT, mutants having modified hydrophobic core had a significantly improved stability. In the present invention, the stability of G9, G13 and G15 respectively was increased by 450%, 1520%, and 1560% relative to the stability of 1G4-WT calculated based data of protein refolding yield.

EXAMPLE 12

Construction of High-stability sTv Molecules with Hydrophobic Core Mutation

High stability sTv molecules were constructed according to hydrophobic core and amino acid residues on surface of the skeleton of variable domains of high-stability mutant screened out in example 9.

A part of hydrophobic core and amino acid residues on surface of the skeleton of variable domains of high-stability mutant screened out in example 9 were introduced into LC13-WT, JM22-WT and MAGE-sTv-WT molecules according to the well-known method of directed mutagenesis in the art. The molecules having introduced mutations were respectively named as LC13-G9, LC13-G15, JM22-G9, JM22-G15 and MAGE-G15 and the hydrophobic core introduced was shown in bold and underlined.

The amino acid sequences of α chain and β chain variable domain of LC13-G9 were SEQ ID NO: 99 and SEQ ID NO: 100 respectively, as shown in FIGS. 32a and 32b and the hydrophobic core introduced in α chain comprised 13V, 21I, 91I and 94I and the hydrophobic core introduced in β chain comprised 11V, 13V and 94V. The amino acid sequences of α chain and β chain variable domain of LC13-G15 were SEQ ID NO:101 and SEQ ID NO: 102 respectively, as shown in FIGS. 33a and 33b and the hydrophobic core introduced in α chain comprised 11L, 13V, 21I, 91I and 94I and the hydrophobic core introduced in β chain comprised 11L, 13V and 94V. The amino acid sequences of α chain and β chain variable domain of JM22-G9 were SEQ ID NO:103 and SEQ ID NO: 104 respectively, as shown in FIGS. 34a and 34b and the hydrophobic core introduced in α chain comprised 11M, 13V, 19V, 21I and 94I and the hydrophobic core introduced in β chain comprised 11V, 13V, 91I and 94V. The amino acid sequences of α chain and β chain variable domain of JM22-G15 were SEQ ID NO:105 and SEQ ID NO: 106 respectively, as shown in FIGS. 35a and 35b and the hydrophobic core introduced in α chain comprised 13V, 19V, 21I and 94I and the hydrophobic core introduced in β chain comprised 13V, 91I and 94V. The amino acid sequences of α chain and β chain variable domain of MAGE-G15 were SEQ ID NO:107 and SEQ ID NO: 108 respectively, as shown in FIGS. 42a and 42b and the hydrophobic core introduced in α chain comprised 19V, 21I and 94I and the hydrophobic core introduced in β chain comprised 13V, 89L, 91I and 94V.

The above numbering of amino acid position was the numbering shown in IMGT. Short peptide for linkage (linker) used for construction of above single-chain molecules could be any suitable sequence and the preferred amino acid sequence in the present invention was SEQ ID NO: 41, as shown in FIG. 16.

EXAMPLE 13

Stability Test of Proteins LC13-G9 and LC13-G15

Using the method described in Example 3, proteins of LC13-G9 and LC13-G15 were expressed, refolded, and purified. After gel filtration column purification, a SDS-PAGE gel was run and SEC profiles of two proteins were made using method of gel filtration. The expression quantity, purified protein quantity and protein refolding yield were calculated at the same time.

Table 11 showed data of the expression quantity, purified protein quantity and protein refolding yield of LC13-G9 and LC13-G15. The relevant data of LC13-WT were also listed for analysis.

TABLE 11

| Protein name | Expression quantity(mg/L) | Purified protein quantity(mg/L) | Yield(%) |
| --- | --- | --- | --- |
| LC13-WT | 231 | 1.3 | 0.56% |
| LC13-G9 | 233 | 1.37 | 0.59% |
| LC13-G15 | 185 | 61.05 | 33% |

The data of above table showed that, after purification, the protein refolding yield of proteins LC13-G9 and LC13-G15 having mutations introduced in hydrophobic core was respectively increased by 5.4% and 57.9 folds compared with that of 1G4-WT protein having no mutation in hydrophobic core.

FIG. 36 shows the SDS-PAGE gel results of proteins of LCI3-G9 and LCI3-G15 purified by a gel filtration column (Superdex 75 10/300, GE Healthcare) as described in Example 3. The gel photo showed that the band formed by purified LCI3-WT protein was heterogeneous, and both modified LC13-G9 and LC13-G15 formed a single band of monomer with a high purity. It suggested that the refolding of LC13-G9 and LC13-G15 was much better than that of LC13-WT.

FIGS. 37 and 38 show SEC profiles of proteins LC13-G9 and LC13-G15, respectively. The SEC profile of LC13-WT did not show a peak, while proteins LC13-G9 and LC13-G15 formed unitary and symmetrical elution peaks. It suggested that the refolding of LC13-G9 and LC13-G15 was significantly better than that of LC13-WT.

The Tm values of LC13-G9 and LC13-G15 measured using the method of example 10 were 43□ and 50.5□, respectively, and their DSC curves were shown in FIGS. 49a and 49b. The protein with correct conformation obtained from LC13-WT refolding was very little and had no apparent endothermic peak of protein unfolding. The Tm value of LC13-WT could not be detected. It suggested that the thermal stability of LC13-G9 and LC13-G15 of the present invention was increased by at least 1 fold relative to that of LC13-WT. In the meantime, it indicated that, compared with LC13-WT, LC13-G9 and LC13-G15 were more resistant to unfolding, were more resistant to inappropriate or undesired folding, and had a stronger renaturability.

After comparative analysis of the expression quantity, the purified protein quantity, the protein refolding yield, SDS-PAGE gel maps, DSC graphs, and SEC profiles of the proteins of LC13-G9 and LC13-G15 and relevant data of LC13-WT, it could be seen that, compared with LC13-WT having a non-modified hydrophobic core, LC13-G9 and LC13-G15 having modified hydrophobic core had a stronger renaturability, were more resistant to unfolding, were more resistant to inappropriate or undesired folding, had a stronger renaturability, had a improved thermal stability and had a higher protein refolding yield. Thus, compared to LC13-WT, LC13-G9 and LC13-G15 of the present invention had a significantly improved stability. In the present invention, the stability of LC13-G9 and LC13-G15 was increased by 5.4% and 57.9 folds relative to the stability of LC13-WT calculated based on data of protein refolding yield.

EXAMPLE 14

Stability Test of Proteins JM22-G9 and JM22-G15

Using the method described in Example 3, proteins of JM22-G9 and JM22-G15 were expressed, refolded, and purified. After gel filtration column purification, a SDS-PAGE gel was run and SEC profiles of two proteins were made using method of gel filtration. The expression quantity, purified protein quantity and protein refolding yield were calculated at the same time.

Table 12 showed data of the expression quantity, purified protein quantity and protein refolding yield of JM22-G9 and JM22-G15. The relevant data of JM22-WT were also listed for analysis.

TABLE 12

| Protein name | Expression quantity(mg/L) | Purified protein quantity(mg/L) | Yield(%) |
|---|---|---|---|
| JM22-WT | 152 | 0.67 | 0.4% |
| JM22-G9 | 358 | 42.2 | 11.8% |
| JM22-G15 | 240 | 123.18 | 51.3% |

The data of above table showed that, after purification, the protein refolding yield of proteins JM22-G9 and JM22-G15 was increased by 28.5 folds and 127.25 folds respectively compared with that of JM22-WT protein having no hydrophobic core mutation.

FIG. 39 shows the SDS-PAGE gel results of proteins of JM22-G9 and JM22-G15 purified by a gel filtration column (Superdex 75 10/300, GE Healthcare) as described in Example 3. The gel photo showed that the monomer bands formed by refolded JM22-WT protein were heterogeneous and there were three bands, and the modified JM22-G9 and JM22-G15 all formed a single band of monomer with a high purity. It suggested that the refolding of JM22-G9 and JM22-G15 was much better than that of JM22-WT.

FIGS. 40 and 41 show SEC profiles of purified proteins JM22-G9 and JM22-G15 respectively. As shown, the elution peak formed by purified protein JM22-WT was not unitary and the signal was very low, while purified JM22-G9 and JM22-G15 formed a unitary and symmetrical elution peak. It further indicated that the refolding of JM22-G9 and JM22-G15 was significantly better than that of JM22-WT.

After comparative analysis of the expression quantity, the purified protein quantity, the protein refolding yield, SDS-PAGE gel maps, DSC graphs, and SEC profiles of the proteins of JM22-G9 and JM22-G15, it could be seen that, compared to JM22-WT having a non-modified hydrophobic core, JM22-G9 and JM22-G15 having modified hydrophobic core had a stronger renaturability, had a higher expression quantity and a higher protein refolding yield. Thus, compared to JM22-WT, JM22-G9 and JM22-G15 had a significantly improved stability. In the present invention, the stability of JM22-G9 and JM22-G15 was increased by 28.5 folds and 127.25 folds respectively relative to the stability of JM22-WT calculated based on data of protein refolding yield.

EXAMPLE 15

Stability Test of Proteins MAGE-sTv-WT and MAGE-G15

Using the method described in Example 3, protein MAGE-G15 was expressed, refolded, and purified. After gel filtration column purification, a SDS-PAGE gel was run and SEC profile was made using method of gel filtration. The expression quantity, purified protein quantity and protein refolding yield were calculated at the same time.

Table 13 showed data of the expression quantity, purified protein quantity and protein refolding yield of MAGE-sTv-WT and MAGE-G15.

TABLE 13

| Protein name | Expression quantity(mg/L) | Purified protein quantity(mg/L) | Yield(%) |
|---|---|---|---|
| MAGE-sTv-WT | 270 | 0 | 0 |
| MAGE-G15 | 220 | 19.8 | 9% |

The target component from protein MG-sTv-WT could not be obtained using gel filtration column as described in Example 3. Thus, SDS-PAGE gel map, SEC profile and DSC graph (Tm value) could not be obtained.

FIG. 43 shows the SDS-PAGE result of protein MAGE-G15 having modified hydrophobic core and purified by a gel filtration column (Superdex 75 10/300, GE Healthcare). The gel photo showed that MAGE-G15 formed a single band with high purity. It indicated that the refolding of MAGE-G15 was much better than that of MG-sTv-WT.

FIG. 45 shows DSC graph of MAGE-G15. Its Tm value obtained by using fitting model of TwostateScaled of analyzing software Nanoanalyze was 46.7□.

Binding of MAGE-G15 to its ligand was detected with BIAcore T200 real-time analysis system. The result showed that affinity of MAGE-G15 protein to its ligand was not better than that of its corresponding wild-type TCR, whose $K_D$ value was 30.4 μM.

The amount of increased stability was calculated based on data of protein refolding yield. It could be seen from Table 13 that compared to MAGE-sTv-WT the stability of MAGE-G15 of the present invention was improved by infinite folds (at least 10,000 folds).

The above data showed that, compared to MAGE-sTv-WT, the renaturability, the protein refolding yield, and the thermal stability of MAGE-G15 of the present invention had a very significant improvement. Therefore, the stability of MAGE-G15 of the present invention had a significant increase compared to MAGE-sTv-WT.

EXAMPLE 16

Mass Spectrometry Analysis

The constructed proteins were purified by gel filtration column (Superdex 75 10/300, GE Healthcare). Molecular weight of whole protein was determined by a mass spectrometry and analyzed whether it was consistent with the theoretical molecular weight so as to examine whether the sequence of purified protein was identical with the sequence of original design.

Molecular weight of whole protein was determined by a mass spectrometry (Eksigent nano LC (nanoflex)—Triple TOF 5600 LC-MS system) of AB SCIEX company of America. The sample was diluted with 10% acetonitrile (Fisher A955-4), 1% formic acid (Fisher A11750) and water (Sigma39253-1L-R) before mass spectrometry analysis. Analysis conditions of the system were as follows:

LC portion

Eksigent nano LC (nanoflex) of AB SCIEX

Guard column: C4-3 μm 300 Å 200 μm×0.5 mm; Lot 804-00019

Analysis Column: C4; 3 μm, 300 Å; 75 μm*15 cm, Lot 804-00018

Mobile phase A: 2% acetonitrile, 0.1% formic acid

Mobile phase B: 98% acetonitrile, 0.1% formic acid

Flow rate: 300 nl/min

Gradient: ratio of B liquid was raised from 5% to 90% in 10 minutes and the total run time was 30 minutes.

Mass portion

Eluent of the column was analyzed with Triple TOF 5600 with Nanospray source

Data collection methods: positive ion MS

Data acquisition range: 400-200 m/z.

Molecular weight of whole protein of sample was obtained from collected MS data after deconvolution process using Bioanalyst software.

After analysis, molecular weight of whole protein (molecules constructed in the present invention after expression, refolding and purification) determined by a MS was consistent with the theoretical molecular weight, indicating that the sequence of protein obtained after purification was identical with the sequence of protein of original design.

The hydrophobic core screened out in the present invention could significantly improve stability of TCR molecules. Meanwhile, the above examples demonstrated that introducing the hydrophobic core screened out in the present invention to the other TCR molecules could also play a role for enhancing stability.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A mutated T cell receptor (TCR) that is a single-chain TCR, comprising a mutated TCR α chain variable domain, a mutated TCR β chain variable domain, and a flexible peptide linker linking the variable domains,
   wherein the mutated α chain variable domain amino acid sequence is selected from the group consisting of SEQ ID NOs: 35, 99, and 101;
   wherein the mutated β chain variable domain amino acid sequence is selected from the group consisting of SEQ ID NOs: 36, 100, and 102;
   wherein the mutated TCR has a stability at least 80% higher than that of the corresponding wild-type TCR with wild-type hydrophobic core, wherein the term "stability" refers to protein stability, and wherein compared with the original wild-type TCR, the mutated TCR has one or more characteristics selected from the group consisting of higher resistance to unfolding, higher resistance to inappropriate or undesirable folding, stronger renaturability, stronger expression ability, higher protein renaturation yield, and increased thermal stability.

2. The mutated TCR of claim 1, wherein CDR regions of the mutated TCR are same as the CDR regions of the corresponding wild-type TCR.

3. The mutated TCR of claim 1, wherein the mutated TCR is water-soluble.

4. The mutated TCR of claim 1, wherein a conjugate is bound to the C-terminal or N-terminal of the α chain and/or β chain of the mutated TCR.

5. The mutated TCR of claim 4, wherein the conjugate bound to the mutated TCR is a detectable marker, a therapeutic agent, or a combination thereof.

6. The mutated TCR of claim 5, wherein the therapeutic agent bound to the mutated TCR is an anti-CD3 antibody linked to the C- or N terminal of the α chain or β chain of the mutated TCR.

7. The mutated TCR of claim 1, wherein the mutation is screened out by phage display technology.

8. A TCR complex comprising one or more mutated TCR molecules of claim 1.

9. A pharmaceutical composition comprising a pharmaceutically acceptable carrier and a safe and effective dosage of the mutated TCR of claim 1.

10. An isolated cell presenting the mutated TCR of claim 1.

11. The mutated TCR of claim 1, wherein the mutated α chain variable domain and the mutated β chain variable domain are selected from the group consisting of:
 (a) α chain variable domain having amino acid sequence of SEQ ID NO:35 and β chain variable domain having amino acid sequence of SEQ ID NO:36;
 (b) α chain variable domain having amino acid sequence of SEQ ID NO:99 and β chain variable domain having amino acid sequence of SEQ ID NO:100; and
 (c) α chain variable domain having amino acid sequence of SEQ ID NO:101 and β chain variable domain having amino acid sequence of SEQ ID NO:102.

* * * * *

SEQUENCE LISTING

```
<160> NUMBER OF SEQ ID NOS: 108

<210> SEQ ID NO 1
<211> LENGTH: 35
<212> TYPE: DNA
<213> ORGANISM: Artificial sequence
<220> FEATURE:
<223> OTHER INFORMATION: Primer

<400> SEQUENCE: 1
aacaggagtg acgcagtctc cttcatctgt gagtg                              35

<210> SEQ ID NO 2
<211> LENGTH: 37
<212> TYPE: DNA
<213> ORGANISM: Artificial sequence
<220> FEATURE:
<223> OTHER INFORMATION: Primer

<400> SEQUENCE: 2
ttagcgccat ggcccaaaaa caggaggtga cgcagtc                            37

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
gaatcttctc agcccgggga c                                             21

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
cgggctgaga agattcaatg                                               20

<210> SEQ ID NO 5
<211> LENGTH: 37
<212> TYPE: DNA
<213> ORGANISM: Artificial sequence
<220> FEATURE:
<223> OTHER INFORMATION: Primer

<400> SEQUENCE: 5
gccaccgcca gatccaccgg gccctggagt gaccgag                            37
```

<210> SEQ ID NO 6
<211> LENGTH: 66
<212> TYPE: DNA
<213> ORGANISM: Artificial sequence
<220> FEATURE:
<223> OTHER INFORMATION: Primer

<400> SEQUENCE: 6
gtggatctgg cggtggcggt gaaggcggtg gtggaagcgg cggcggaggc gaaggaggct    60
ccggag                                                               66

<210> SEQ ID NO 7
<211> LENGTH: 40
<212> TYPE: DNA
<213> ORGANISM: Artificial sequence
<220> FEATURE:
<223> OTHER INFORMATION: Primer

<400> SEQUENCE: 7
gcgaaggagg ctccggaggc aaggctggag tcactcaaac                          40

<210> SEQ ID NO 8
<211> LENGTH: 33
<212> TYPE: DNA
<213> ORGANISM: Artificial sequence
<220> FEATURE:
<223> OTHER INFORMATION: Primer

<400> SEQUENCE: 8
ctagatgcgg ccgcctctgt gaccgtgagc ctg                                 33

<210> SEQ ID NO 9
<211> LENGTH: 114
<212> TYPE: PRT
<213> ORGANISM: Artificial sequence
<220> FEATURE:
<223> OTHER INFORMATION: Polypeptide

<400> SEQUENCE: 9

Lys Gln Glu Val Thr Gln Ser Pro Ser Ser Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Val Arg Pro Tyr Gln Arg Glu Gln Thr Ser Gly Arg Leu Asn Ala
    50                  55                  60

Ser Leu Asp Lys Ser Ser Gly Arg Ser Thr Leu Tyr Ile Glu Ser Ser
65                  70                  75                  80

Gln Pro Gly Asp Ser Ala Thr Tyr Leu Cys Ala Val Arg Pro Gly Gly
                85                  90                  95

Ala Gly Ser Tyr Gln Leu Thr Phe Gly Lys Gly Thr Lys Leu Ser Val
            100                 105                 110

Thr Pro

<210> SEQ ID NO 10
<211> LENGTH: 342
<212> TYPE: DNA
<213> ORGANISM: Artificial sequence
<220> FEATURE:
<223> OTHER INFORMATION: Polyribonucleotide

<400> SEQUENCE: 10

```
aaacaggagg tgacgcagtc tccttcatct ctgagtgtcc cagaaggaga aaacttgtct    60
ctcaactgca gtttcactga tagcgctatt tacaacctcc agtggtttag gcaggaccct   120
gggaaaggtc tcacatctct gttgttagtg cgtccgtatc agagagagca aacaagtgga   180
agacttaatg cctcgctgga taaatcatca ggacgtagta cttatacat tgaatcttct    240
cagcccgggg actcagccac ctacctctgt gctgtgaggc cggagggggc tgggagttac   300
caactcactt cgggaaggg gaccaaactc tcggtcactc ca                       342
```

<210> SEQ ID NO 11
<211> LENGTH: 112
<212> TYPE: PRT
<213> ORGANISM: artificial sequence
<220> FEATURE:
<223> OTHER INFORMATION: Polypeptide

<400> SEQUENCE: 11

```
Lys Ala Gly Val Thr Gln Thr Pro Arg Tyr Leu Ser Lys Thr Arg Gly
1               5                   10                  15
Gln Gln Val Thr Leu Ser Cys Ser Pro Ile Ser Gly His Arg Ser Val
            20                  25                  30
Ser Trp Tyr Gln Gln Thr Pro Gly Gln Gly Leu Gln Phe Leu Phe Glu
        35                  40                  45
Tyr Phe Ser Glu Thr Gln Arg Asn Lys Gly Asn Phe Pro Gly Arg Phe
    50                  55                  60
Ser Gly Arg Gln Phe Ser Asn Ser Arg Ser Glu Met Asn Val Ser Thr
65                  70                  75                  80
Leu Glu Leu Gly Asp Ser Ala Leu Tyr Leu Cys Ala Ser Ser Pro Asn
                85                  90                  95
Met Ala Asp Glu Gln Tyr Phe Gly Pro Gly Thr Arg Leu Thr Val Thr
            100                 105                 110
```

<210> SEQ ID NO 12
<211> LENGTH: 336
<212> TYPE: DNA
<213> ORGANISM: artificial sequence
<220> FEATURE:
<223> OTHER INFORMATION: Polyribonucleotide

<400> SEQUENCE: 12

```
aaggctggag tcactcaaac tccaagatat ctgtccaaaa cgagaggaca gcaagtgaca    60
ctgagctgct cccctatctc tgggcatagg agtgtatcct ggtaccaaca gaccccagga   120
cagggccttc agttcctctt tgaatacttc agtgagacac agagaaacaa aggaaacttc   180
cctggtcgat tctcagggcg ccagttctct aactctcgct ctgagatgaa tgtgagcacc   240
ttggagctgg gggactcggc cctttatctt tgcgccagca gcccgaacat ggccgacgag   300
cagtacttcg ggccgggcac caggctcacg gtcaca                             336
```

<210> SEQ ID NO 13
<211> LENGTH: 25
<212> TYPE: PRT
<213> ORGANISM: Artificial sequence
<220> FEATURE:
<223> OTHER INFORMATION: Polypeptide

<400> SEQUENCE: 13

Gly Pro Gly Gly Ser Gly Gly Gly Gly Glu Gly Gly Gly Gly Ser Gly

```
                1               5                  10                 15
Gly Gly Gly Glu Gly Gly Ser Gly Gly
                20                  25

<210> SEQ ID NO 14
<211> LENGTH: 75
<212> TYPE: DNA
<213> ORGANISM: Artificial sequence
<220> FEATURE:
<223> OTHER INFORMATION: Polyribonucleotide

<400> SEQUENCE: 14
gggcccggtg gatctggcgg tggcggtgaa ggcggtggtg aagcggcgg cggaggcgaa    60 ggaggctccg gaggc                                                    75

<210> SEQ ID NO 15
<211> LENGTH: 114
<212> TYPE: PRT
<213> ORGANISM: Artificial sequence
<220> FEATURE:
<223> OTHER INFORMATION: Polypeptide

<400> SEQUENCE: 15

Lys Gln Glu Val Thr Gln Ser Pro Ser Ser Leu Ser Val Pro Glu Gly
1               5                   10                  15

Glu Asn Val Ser Ile Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Val Arg Pro Tyr Gln Arg Glu Gln Thr Ser Gly Arg Leu Asn Ala
        50                  55                  60

Ser Leu Asp Lys Ser Ser Gly Arg Ser Thr Leu Tyr Leu Glu Ser Ser
65                  70                  75                  80

Gln Pro Gly Asp Ser Ala Thr Tyr Leu Cys Ala Val Arg Pro Gly Gly
                85                  90                  95

Ala Gly Ser Tyr Gln Leu Thr Phe Gly Lys Gly Thr Lys Leu Ser Val
                100                 105                 110

Thr Pro

<210> SEQ ID NO 16
<211> LENGTH: 112
<212> TYPE: PRT
<213> ORGANISM: Artificial sequence
<220> FEATURE:
<223> OTHER INFORMATION: Polypeptide

<400> SEQUENCE: 16

Lys Ala Gly Val Thr Gln Thr Pro Arg Tyr Leu Ser Lys Thr Arg Gly
1               5                   10                  15

Gln Gln Val Thr Leu Ser Cys Ser Pro Ile Ser Gly His Arg Ser Val
                20                  25                  30

Ser Trp Tyr Gln Gln Thr Pro Gly Gln Gly Leu Gln Phe Leu Phe Glu
            35                  40                  45

Tyr Phe Ser Glu Thr Gln Arg Asn Lys Gly Asn Phe Pro Gly Arg Phe
        50                  55                  60

Ser Gly Arg Gln Phe Ser Asn Ser Arg Ser Glu Met Asn Phe Ser Thr
65                  70                  75                  80

Leu Glu Leu Gly Asp Ser Ala Leu Tyr Leu Cys Ala Ser Ser Pro Asn
                85                  90                  95
```

```
Met Ala Asp Glu Gln Tyr Phe Gly Pro Gly Thr Arg Met Thr Val Thr
            100                 105                 110
```

<210> SEQ ID NO 17
<211> LENGTH: 114
<212> TYPE: PRT
<213> ORGANISM: Artificial sequence
<220> FEATURE:
<223> OTHER INFORMATION: Polypeptide

<400> SEQUENCE: 17

```
Lys Gln Glu Val Thr Gln Ser Pro Ser Leu Ser Val Pro Glu Gly
1               5                   10                  15

Glu Asn Val Ser Ile Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Val Arg Pro Tyr Gln Arg Glu Gln Thr Ser Gly Arg Leu Asn Ala
    50                  55                  60

Ser Leu Asp Lys Ser Ser Gly Arg Ser Thr Leu Tyr Ile Glu Ser Ser
65                  70                  75                  80

Gln Pro Gly Asp Ser Ala Thr Tyr Leu Cys Ala Val Arg Pro Gly Gly
                85                  90                  95

Ala Gly Ser Tyr Gln Leu Thr Phe Gly Lys Gly Thr Lys Leu Ser Val
            100                 105                 110

Thr Pro
```

<210> SEQ ID NO 18
<211> LENGTH: 112
<212> TYPE: PRT
<213> ORGANISM: Artificial sequence
<220> FEATURE:
<223> OTHER INFORMATION: Polypeptide

<400> SEQUENCE: 18

```
Lys Ala Gly Val Thr Gln Thr Pro Arg Tyr Leu Ser Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Ile Ser Thr
65                  70                  75                  80

Leu Glu Leu Gly Asp Ser Ala Leu Tyr Leu Cys Ala Ser Ser Pro Asn
                85                  90                  95

Met Ala Asp Glu Gln Tyr Phe Gly Pro Gly Thr Arg Leu Thr Val Thr
            100                 105                 110
```

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19

```
gttttctcct tctgggacac                                          20
```

<210> SEQ ID NO 20
<211> LENGTH: 43
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 20
gtcccagaag gagaaaacnt ktctntkaac tgcagtttca ctg            43

<210> SEQ ID NO 21
<211> LENGTH: 23
<212> TYPE: DNA
<213> ORGANISM: Artificial sequence
<220> FEATURE:
<223> OTHER INFORMATION: Primer

<400> SEQUENCE: 21
gtataaagta ctacgtcctg atg            23

<210> SEQ ID NO 22
<211> LENGTH: 36
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (21)..(21)
<223> OTHER INFORMATION: n is a, c, g, or t

<400> SEQUENCE: 22
caggacgtag tactttatac ntkgaatctt ctcagc            36

<210> SEQ ID NO 23
<211> LENGTH: 22
<212> TYPE: DNA
<213> ORGANISM: Artificial sequence
<220> FEATURE:
<223> OTHER INFORMATION: Primer

<400> SEQUENCE: 23
ttgctgtcct ctcgttttgg ac            22

<210> SEQ ID NO 24
<211> LENGTH: 43
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 24
caaaacgaga ggacagcaan tkacantkag ctgctcccct atc                43

<210> SEQ ID NO 25
<211> LENGTH: 19
<212> TYPE: DNA
<213> ORGANISM: Artificial sequence
<220> FEATURE:
<223> OTHER INFORMATION: Primer

<400> SEQUENCE: 25
attcatctca gagcgagag                                           19

<210> SEQ ID NO 26
<211> LENGTH: 35
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: n is a, c, g, or t

<400> SEQUENCE: 26
ctcgctctga gatgaatntk agcaccttgg agctg                         35

<210> SEQ ID NO 27
<211> LENGTH: 42
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t

<400> SEQUENCE: 27
gccgcctctg tgaccgtman cctmrkgccc ggcccgaagt ac                 42

<210> SEQ ID NO 28
<211> LENGTH: 31
<212> TYPE: DNA
<213> ORGANISM: Artificial sequence
<220> FEATURE:
<223> OTHER INFORMATION: Primer

<400> SEQUENCE: 28
acggtcacag aggcggccgc atctagaatt c                             31

<210> SEQ ID NO 29
<211> LENGTH: 113
<212> TYPE: PRT
<213> ORGANISM: Artificial sequence
<220> FEATURE:
<223> OTHER INFORMATION: Polypeptide

<400> SEQUENCE: 29

Asp Ala Lys Thr Thr Gln Pro Asn Ser Met Glu Ser Asn Glu Glu
1               5                   10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
            35                  40                  45

His Gly Leu Thr Ser Asn Val Asn Asn Arg Met Ala Ser Leu Ala Ile
        50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Arg Asp Ala Gly Gly Thr
                85                  90                  95

Ser Tyr Gly Lys Leu Thr Phe Gly Gln Gly Thr Ile Leu Thr Val His
            100                 105                 110

Pro

<210> SEQ ID NO 30
<211> LENGTH: 113
<212> TYPE: PRT
<213> ORGANISM: Artificial sequence
<220> FEATURE:
<223> OTHER INFORMATION: Polypeptide

<400> SEQUENCE: 30

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
                20                  25                  30

Phe Trp Tyr Gln Gln Ala Leu Gly Gln Gly Pro Glu Phe Leu Thr Tyr
            35                  40                  45

Phe Gln Asn Glu Ala Gln Leu Asp Lys Ser Gly Leu Pro Ser Asp Arg
50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Leu
                85                  90                  95

Gly Gln Ser Tyr Glu Gly Tyr Phe Gly Pro Gly Thr Arg Leu Thr Val
            100                 105                 110

Thr

<210> SEQ ID NO 31
<211> LENGTH: 110
<212> TYPE: PRT
<213> ORGANISM: Artificial sequence
<220> FEATURE:
<223> OTHER INFORMATION: Polypeptide

<400> SEQUENCE: 31

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
                20                  25                  30

Gln Trp Tyr Arg Gln Glu Pro Gly Glu Gly Pro Val Leu Leu Val Thr
            35                  40                  45

Val Val Thr Gly Gly Glu Val Lys Lys Leu Lys Arg Leu Thr Phe Gln
50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Gly Ser Gln Gly
                85                  90                  95

Asn Leu Ile Phe Gly Lys Gly Thr Lys Leu Ser Val Lys Pro
            100                 105                 110

<210> SEQ ID NO 32
<211> LENGTH: 112

<212> TYPE: PRT
<213> ORGANISM: Artificial sequence
<220> FEATURE:
<223> OTHER INFORMATION: Polypeptide

<400> SEQUENCE: 32

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Ile Arg
                85                  90                  95

Ser Ser Tyr Glu Gln Tyr Phe Gly Pro Gly Thr Arg Leu Thr Val Thr
            100                 105                 110

<210> SEQ ID NO 33
<211> LENGTH: 114
<212> TYPE: PRT
<213> ORGANISM: Artificial sequence
<220> FEATURE:
<223> OTHER INFORMATION: Polypeptide

<400> SEQUENCE: 33

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Ser
                85                  90                  95

Gly Gly Ser Tyr Ile Pro Thr Phe Gly Arg Gly Thr Ser Leu Ile Val
            100                 105                 110

His Pro

<210> SEQ ID NO 34
<211> LENGTH: 113
<212> TYPE: PRT
<213> ORGANISM: Artificial sequence
<220> FEATURE:
<223> OTHER INFORMATION: Polypeptide

<400> SEQUENCE: 34

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

```
Ser Val Gly Ala Gly Ile Thr Asp Gln Gly Glu Val Pro Asn Gly Tyr
        50                  55                  60

Asn Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Ser Tyr Val
                 85                  90                  95

Gly Asn Thr Gly Glu Leu Phe Phe Gly Glu Gly Ser Arg Leu Thr Val
                100                 105                 110

Leu
```

<210> SEQ ID NO 35
<211> LENGTH: 113
<212> TYPE: PRT
<213> ORGANISM: Artificial sequence
<220> FEATURE:
<223> OTHER INFORMATION: Polypeptide

<400> SEQUENCE: 35

```
Asp Ala Lys Thr Thr Gln Pro Asn Ser Leu Glu Val Asn Glu Glu Glu
 1               5                  10                  15

Pro Val His Ile Pro Cys Asn His Ser Thr Ile Ser Gly Thr Asp Tyr
                 20                  25                  30

Ile His Trp Tyr Arg Gln Leu Pro Ser Gln Gly Pro Glu Tyr Val Ile
             35                  40                  45

His Gly Leu Thr Ser Asn Val Asn Asn Arg Met Ala Ser Leu Ala Ile
         50                  55                  60

Ala Glu Asp Arg Lys Ser Ser Thr Leu Tyr Ile His Arg Ala Thr Pro
 65                  70                  75                  80

Arg Asp Ser Ala Thr Tyr Phe Cys Ala Val Pro Leu Ala Gly Gly Thr
                 85                  90                  95

Ser Tyr Gly Lys Leu Thr Phe Gly Lys Gly Thr Lys Leu Ser Val Thr
                100                 105                 110

Pro
```

<210> SEQ ID NO 36
<211> LENGTH: 113
<212> TYPE: PRT
<213> ORGANISM: Artificial sequence
<220> FEATURE:
<223> OTHER INFORMATION: Polypeptide

<400> SEQUENCE: 36

```
Gly Ala Gly Val Ser Gln Ser Pro Arg Tyr Lys Ser Ala Lys Arg Gly
 1               5                  10                  15

Gln Asp Val Thr Leu Arg Cys Asp Pro Ile Ser Gly His Val Ser Leu
                 20                  25                  30

Phe Trp Tyr Gln Gln Ala Pro Gly Gln Gly Pro Glu Phe Leu Thr Tyr
             35                  40                  45

Phe Gln Asn Glu Ala Gln Leu Asp Lys Ser Gly Leu Pro Ser Asp Arg
         50                  55                  60

Phe Ser Ala Glu Arg Pro Glu Gly Ser Val Ser Thr Leu Lys Ile Gln
 65                  70                  75                  80

Arg Leu Gln Pro Glu Asp Ser Ala Val Tyr Leu Cys Ala Ser Ser Leu
                 85                  90                  95

Gly Gln Ala Tyr Glu Gln Tyr Phe Gly Pro Gly Thr Arg Leu Thr Val
                100                 105                 110
```

Thr

<210> SEQ ID NO 37
<211> LENGTH: 110
<212> TYPE: PRT
<213> ORGANISM: Artificial sequence
<220> FEATURE:
<223> OTHER INFORMATION: Polypeptide

<400> SEQUENCE: 37

```
Thr Gln Leu Leu Glu Gln Ser Pro Gln Ser Leu Ser Ile Gln Glu Gly
1               5                   10                  15

Glu Asn Val Thr Ile Tyr Cys Asn Ser Ser Val Phe Ser Ser Leu
            20                  25                  30

Gln Trp Tyr Arg Gln Glu Pro Gly Glu Gly Pro Thr Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ser Ala Gln
65                  70                  75                  80

Pro Gly Asp Ser Gly Thr Tyr Phe Cys Ala Val Ala Gly Ser Gln Gly
                85                  90                  95

Asn Leu Ile Phe Gly Lys Gly Thr Lys Leu Ser Val Thr Pro
            100                 105                 110
```

<210> SEQ ID NO 38
<211> LENGTH: 112
<212> TYPE: PRT
<213> ORGANISM: Artificial sequence
<220> FEATURE:
<223> OTHER INFORMATION: Polypeptide

<400> SEQUENCE: 38

```
Asp Gly Gly Ile Thr Gln Ser Pro Lys Tyr Leu Ser Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Ile Thr Ser
65                  70                  75                  80

Leu Gln Lys Asn Asp Ser Ala Val Tyr Leu Cys Ala Ser Ser Ser Arg
                85                  90                  95

Ser Ser Tyr Glu Gln Tyr Phe Gly Pro Gly Thr Arg Leu Thr Val Thr
            100                 105                 110
```

<210> SEQ ID NO 39
<211> LENGTH: 114
<212> TYPE: PRT
<213> ORGANISM: Artificial sequence
<220> FEATURE:
<223> OTHER INFORMATION: Polypeptide

<400> SEQUENCE: 39

```
Lys Gln Glu Val Thr Gln Ser Pro Ser Ser Leu Ser Val Pro Glu Gly
1               5                   10                  15

Glu Asn Val Ser Ile Asn Cys Ser Phe Thr Asp Ser Ala Ile Tyr Asn
            20                  25                  30
```

Leu Gln Trp Phe Arg Gln Asp Pro Gly Lys Gly Leu Thr Ser Leu Leu
             35                  40                  45

Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Glu Ser Ser
 65                  70                  75                  80

Gln Pro Gly Asp Ser Ala Thr Tyr Phe Cys Ala Val Arg Pro Thr Ser
                 85                  90                  95

Gly Gly Ser Tyr Ile Pro Thr Phe Gly Lys Gly Thr Lys Leu Ser Val
                100                 105                 110

Thr Pro

<210> SEQ ID NO 40
<211> LENGTH: 113
<212> TYPE: PRT
<213> ORGANISM: Artificial sequence
<220> FEATURE:
<223> OTHER INFORMATION: Polypeptide

<400> SEQUENCE: 40

Asn Ala Gly Val Thr Gln Thr Pro Lys Tyr Gln Ser Leu Lys Thr Gly
 1               5                  10                  15

Gln Ser Val Thr Leu Gln Cys Ala Gln Asp Met Asn His Glu Tyr Met
                 20                  25                  30

Ser Trp Tyr Arg Gln Asp Pro Gly Gln Gly Leu Arg Leu Ile His Tyr
             35                  40                  45

Ser Val Gly Ala Gly Ile Thr Asp Gln Gly Glu Val Pro Asn Gly Tyr
 50                  55                  60

Asn Val Ser Arg Ser Thr Thr Glu Asp Phe Pro Leu Arg Ile Glu Ser
 65                  70                  75                  80

Leu Thr Pro Ser Asp Ser Ala Val Tyr Leu Cys Ala Ser Ser Tyr Val
                 85                  90                  95

Gly Asn Thr Gly Glu Leu Phe Phe Gly Pro Gly Thr Arg Leu Thr Val
                100                 105                 110

Thr

<210> SEQ ID NO 41
<211> LENGTH: 24
<212> TYPE: PRT
<213> ORGANISM: Artificial sequence
<220> FEATURE:
<223> OTHER INFORMATION: Polypeptide

<400> SEQUENCE: 41

Gly Gly Gly Ser Glu Gly Gly Ser Glu Gly Gly Ser Glu Gly Gly Gly
 1               5                  10                  15

Gly Gly Ser Glu Gly Gly Thr Gly
                 20

<210> SEQ ID NO 42
<211> LENGTH: 251
<212> TYPE: PRT
<213> ORGANISM: Artificial sequence
<220> FEATURE:
<223> OTHER INFORMATION: Polypeptide

<400> SEQUENCE: 42

Lys Gln Glu Val Thr Gln Ser Pro Ser Ser Leu Ser Val Pro Glu Gly
 1               5                  10                  15

Glu Asn Val Ser Ile Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
50                  55                  60

Ser Leu Asp Lys Ser Ser Gly Arg Ser Thr Leu Tyr Ile Glu Ser Ser
65                  70                  75                  80

Gln Pro Gly Asp Ser Ala Thr Tyr Phe Cys Ala Val Arg Pro Thr Ser
                85                  90                  95

Gly Gly Ser Tyr Ile Pro Thr Phe Gly Lys Gly Thr Lys Leu Ser Val
            100                 105                 110

Thr Pro Gly Gly Gly Ser Glu Gly Gly Ser Glu Gly Gly Gly Ser
            115                 120                 125

Glu Gly Gly Gly Ser Glu Gly Gly Thr Gly Asn Ala Gly Val Thr Gln
130                 135                 140

Thr Pro Lys Tyr Gln Ser Leu Lys Thr Gly Gln Ser Val Thr Leu Gln
145                 150                 155                 160

Cys Ala Gln Asp Met Asn His Glu Tyr Met Ser Trp Tyr Arg Gln Asp
            165                 170                 175

Pro Gly Gln Gly Leu Arg Leu Ile His Tyr Ser Val Gly Ala Gly Ile
            180                 185                 190

Thr Asp Gln Gly Glu Val Pro Asn Gly Tyr Asn Val Ser Arg Ser Thr
            195                 200                 205

Thr Glu Asp Phe Pro Leu Arg Ile Glu Ser Leu Thr Pro Ser Asp Ser
210                 215                 220

Ala Val Tyr Leu Cys Ala Ser Ser Tyr Val Gly Asn Thr Gly Glu Leu
225                 230                 235                 240

Phe Phe Gly Pro Gly Thr Arg Leu Thr Val Thr
            245                 250

<210> SEQ ID NO 43
<211> LENGTH: 41
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: n is a, c, g, or t

<400> SEQUENCE: 43
ccggccatgg ccaagcagga antkacgcaa tccccgtcgt c         41

<210> SEQ ID NO 44
<211> LENGTH: 41
<212> TYPE: DNA
<213> ORGANISM: Artificial sequence
<220> FEATURE:
<223> OTHER INFORMATION: Primer

<400> SEQUENCE: 44
aatccccgtc gtcavdgtct vdgccggaag gcgaaaatgt c         41

<210> SEQ ID NO 45
<211> LENGTH: 38
<212> TYPE: DNA
<213> ORGANISM: Artificial sequence

```
<220> FEATURE:
<223> OTHER INFORMATION: Primer
<220> FEATURE:
<221> NAME/KEY: misc_feature
<222> LOCATION: (22)..(22)
<223> OTHER INFORMATION: n is a, c, g, or t

<400> SEQUENCE: 45
tcgcggagtc acccggctgm antgattcaa tatacagg                              38

<210> SEQ ID NO 46
<211> LENGTH: 31
<212> TYPE: DNA
<213> ORGANISM: Artificial sequence
<220> FEATURE:
<223> OTHER INFORMATION: Primer

<400> SEQUENCE: 46
cagccgggtg actccgcgac gtactttgt g                                      31

<210> SEQ ID NO 47
<211> LENGTH: 28
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (17)..(17)
<223> OTHER INFORMATION: n is a, c, g, or t

<400> SEQUENCE: 47
ttcggcgttt gggtmanacc cgcattac                                         28

<210> SEQ ID NO 48
<211> LENGTH: 41
<212> TYPE: DNA
<213> ORGANISM: Artificial sequence
<220> FEATURE:
<223> OTHER INFORMATION: Primer

<400> SEQUENCE: 48
acccaaacgc cgaaatacvd gagcvdgaag acgggtcagt c                          41

<210> SEQ ID NO 49
<211> LENGTH: 31
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t

<400> SEQUENCE: 49
gcggagtcac tcggggtman tgattcaatg c                                     31

<210> SEQ ID NO 50
<211> LENGTH: 36
<212> TYPE: DNA
<213> ORGANISM: Artificial sequence
<220> FEATURE:
<223> OTHER INFORMATION: Primer

<400> SEQUENCE: 50
accccgagtg actccgcadb gtatctgtgt gcttcg                                36
```

<210> SEQ ID NO 51
<211> LENGTH: 25
<212> TYPE: DNA
<213> ORGANISM: Artificial sequence
<220> FEATURE:
<223> OTHER INFORMATION: Primer

<400> SEQUENCE: 51
tcgagtgcgg ccgccgtcac cgtca                                  25

<210> SEQ ID NO 52
<211> LENGTH: 28
<212> TYPE: DNA
<213> ORGANISM: Artificial sequence
<220> FEATURE:
<223> OTHER INFORMATION: Primer

<400> SEQUENCE: 52
agccggccat ggccaagcag gaagtcac                               28

<210> SEQ ID NO 53
<211> LENGTH: 29
<212> TYPE: DNA
<213> ORGANISM: Artificial sequence
<220> FEATURE:
<223> OTHER INFORMATION: Primer

<400> SEQUENCE: 53
gattgagaca ttttcmyytt ccgggacag                              29

<210> SEQ ID NO 54
<211> LENGTH: 37
<212> TYPE: DNA
<213> ORGANISM: Artificial sequence
<220> FEATURE:
<223> OTHER INFORMATION: Primer

<400> SEQUENCE: 54
gtcactgtct gtcccggaar rkgaaaatgt ctcaatc                     37

<210> SEQ ID NO 55
<211> LENGTH: 38
<212> TYPE: DNA
<213> ORGANISM: Artificial sequence
<220> FEATURE:
<223> OTHER INFORMATION: Primer

<400> SEQUENCE: 55
cacaaaagta cgtcgcmyyg tcmyycggct gcgatgat                    38

<210> SEQ ID NO 56
<211> LENGTH: 25
<212> TYPE: DNA
<213> ORGANISM: Artificial sequence
<220> FEATURE:
<223> OTHER INFORMATION: Primer

<400> SEQUENCE: 56
cgacgtactt ttgtgcggtt cgtcc                                  25

<210> SEQ ID NO 57
<211> LENGTH: 25
<212> TYPE: DNA
<213> ORGANISM: Artificial sequence
<220> FEATURE:
<223> OTHER INFORMATION: Primer

```
<400> SEQUENCE: 57
cagcttcgta cccttgccga aggtc                                       25

<210> SEQ ID NO 58
<211> LENGTH: 32
<212> TYPE: DNA
<213> ORGANISM: Artificial sequence
<220> FEATURE:
<223> OTHER INFORMATION: Primer

<400> SEQUENCE: 58
ttcggcaagg gtacgaagct grrkgtcacg cc                               32

<210> SEQ ID NO 59
<211> LENGTH: 40
<212> TYPE: DNA
<213> ORGANISM: Artificial sequence
<220> FEATURE:
<223> OTHER INFORMATION: Primer

<400> SEQUENCE: 59
cattgcaggg tcacmyyctg myycgtmyyc aggctctggt                       40

<210> SEQ ID NO 60
<211> LENGTH: 27
<212> TYPE: DNA
<213> ORGANISM: Artificial sequence
<220> FEATURE:
<223> OTHER INFORMATION: Primer

<400> SEQUENCE: 60
gtgaccctgc aatgcgccca ggatatg                                     27

<210> SEQ ID NO 61
<211> LENGTH: 32
<212> TYPE: DNA
<213> ORGANISM: Artificial sequence
<220> FEATURE:
<223> OTHER INFORMATION: Primer

<400> SEQUENCE: 61
cacagataaa ctgcggagtc myycggggtc ag                               32

<210> SEQ ID NO 62
<211> LENGTH: 30
<212> TYPE: DNA
<213> ORGANISM: Artificial sequence
<220> FEATURE:
<223> OTHER INFORMATION: Primer

<400> SEQUENCE: 62
gactccgcag tttatctgtg tgcttcgtcc                                  30

<210> SEQ ID NO 63
<211> LENGTH: 31
<212> TYPE: DNA
<213> ORGANISM: Artificial sequence
<220> FEATURE:
<223> OTHER INFORMATION: Primer

<400> SEQUENCE: 63
gagtgcggcc gccgtcacmy ycaggcgcgt g                                31

<210> SEQ ID NO 64
```

```
<211> LENGTH: 41
<212> TYPE: DNA
<213> ORGANISM: Artificial sequence
<220> FEATURE:
<223> OTHER INFORMATION: Primer

<400> SEQUENCE: 64
ccggccatgg ccaagcagga agtcacgcaa tccccgtcgt c                    41

<210> SEQ ID NO 65
<211> LENGTH: 35
<212> TYPE: DNA
<213> ORGANISM: Artificial sequence
<220> FEATURE:
<223> OTHER INFORMATION: Primer

<400> SEQUENCE: 65
acgcaatccc cgtcgtcact grrkgtcccg gaagg                           35

<210> SEQ ID NO 66
<211> LENGTH: 38
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: n is a, c, g, or t

<400> SEQUENCE: 66
ggagtcaccc ggctgmanmy yttcaatata cagggtac                        38

<210> SEQ ID NO 67
<211> LENGTH: 33
<212> TYPE: DNA
<213> ORGANISM: Artificial sequence
<220> FEATURE:
<223> OTHER INFORMATION: Primer

<400> SEQUENCE: 67
cagccgggtg actccrrkac gtactttgt gcg                              33

<210> SEQ ID NO 68
<211> LENGTH: 33
<212> TYPE: DNA
<213> ORGANISM: Artificial sequence
<220> FEATURE:
<223> OTHER INFORMATION: Primer

<400> SEQUENCE: 68
ttcgctgccg cccccmyycg tgacgctcag ctt                             33

<210> SEQ ID NO 69
<211> LENGTH: 30
<212> TYPE: DNA
<213> ORGANISM: Artificial sequence
<220> FEATURE:
<223> OTHER INFORMATION: Primer

<400> SEQUENCE: 69
aagctgagcg tcacgrrkgg gggcggcagc                                 30

<210> SEQ ID NO 70
<211> LENGTH: 37
<212> TYPE: DNA
<213> ORGANISM: Artificial sequence
```

```
<220> FEATURE:
<223> OTHER INFORMATION: Primer

<400> SEQUENCE: 70
gcattgcagg gtcacagact gaccmyyctt caggctc                               37

<210> SEQ ID NO 71
<211> LENGTH: 35
<212> TYPE: DNA
<213> ORGANISM: Artificial sequence
<220> FEATURE:
<223> OTHER INFORMATION: Primer

<400> SEQUENCE: 71
gtcagtctgt gaccctgcaa tgcgcccagg atatg                                 35

<210> SEQ ID NO 72
<211> LENGTH: 34
<212> TYPE: DNA
<213> ORGANISM: Artificial sequence
<220> FEATURE:
<223> OTHER INFORMATION: Primer

<400> SEQUENCE: 72
ctgcggagtc actcggmyyc agmyyttcaa tgcg                                  34

<210> SEQ ID NO 73
<211> LENGTH: 36
<212> TYPE: DNA
<213> ORGANISM: Artificial sequence
<220> FEATURE:
<223> OTHER INFORMATION: Primer

<400> SEQUENCE: 73
ccgagtgact ccgcagttta tctgtgtgct tcgtcc                                36

<210> SEQ ID NO 74
<211> LENGTH: 23
<212> TYPE: DNA
<213> ORGANISM: Artificial sequence
<220> FEATURE:
<223> OTHER INFORMATION: Primer

<400> SEQUENCE: 74
agtgcggccg cmyycaccgt cag                                              23

<210> SEQ ID NO 75
<211> LENGTH: 114
<212> TYPE: PRT
<213> ORGANISM: Artificial sequence
<220> FEATURE:
<223> OTHER INFORMATION: Polypeptide

<400> SEQUENCE: 75

Lys Gln Glu Leu Thr Gln Ser Pro Ser Ser Leu Asn Arg Pro Glu Ser
 1               5                  10                  15

Glu Asn Val Ser Ile Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Glu Asn Val
65                  70                  75                  80
```

Gln Pro Asn Asp Ser Gly Thr Tyr Phe Cys Ser Val Arg Pro Thr Ser
                85                  90                  95

Gly Gly Ser Tyr Ile Pro Thr Phe Gly Lys Gly Thr Lys Leu Ser Val
                100                 105                 110

Thr Asn

<210> SEQ ID NO 76
<211> LENGTH: 114
<212> TYPE: PRT
<213> ORGANISM: Artificial sequence
<220> FEATURE:
<223> OTHER INFORMATION: Polypeptide

<400> SEQUENCE: 76

Lys Gln Glu Val Thr Gln Ser Pro Ser Ser Met Asn Val Pro Glu Ser
1               5                   10                  15

Glu Asn Val Ser Ile Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Glu Asn Val
65                  70                  75                  80

Gln Pro Asn Asp Ser Gly Thr Tyr Phe Cys Ala Val Arg Pro Thr Ser
                85                  90                  95

Gly Gly Ser Tyr Ile Pro Thr Phe Gly Lys Gly Thr Lys Leu Ser Val
                100                 105                 110

Thr Asn

<210> SEQ ID NO 77
<211> LENGTH: 114
<212> TYPE: PRT
<213> ORGANISM: Artificial sequence
<220> FEATURE:
<223> OTHER INFORMATION: Polypeptide

<400> SEQUENCE: 77

Lys Gln Glu Leu Thr Gln Ser Pro Ser Ser Glu Asn Val Pro Glu Ser
1               5                   10                  15

Glu Asn Val Ser Ile Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Glu Asn Val
65                  70                  75                  80

Gln Pro Asn Asp Ser Gly Thr Tyr Phe Cys Ser Val Arg Pro Thr Ser
                85                  90                  95

Gly Gly Ser Tyr Ile Pro Thr Phe Gly Lys Gly Thr Lys Leu Ser Val
                100                 105                 110

Thr Asn

<210> SEQ ID NO 78
<211> LENGTH: 114
<212> TYPE: PRT

<213> ORGANISM: Artificial sequence
<220> FEATURE:
<223> OTHER INFORMATION: Polypeptide

<400> SEQUENCE: 78

```
Lys Gln Glu Leu Thr Gln Ser Pro Ser Ser Leu Asn Val Pro Glu Ser
1               5                   10                  15

Glu Asn Val Ser Ile Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Glu Asn Val
65                  70                  75                  80

Gln Pro Asn Asp Ser Gly Thr Tyr Phe Cys Ser Val Arg Pro Thr Ser
                85                  90                  95

Gly Gly Ser Tyr Ile Pro Thr Phe Gly Lys Gly Thr Lys Leu Ser Val
            100                 105                 110

Thr Asn
```

<210> SEQ ID NO 79
<211> LENGTH: 114
<212> TYPE: PRT
<213> ORGANISM: Artificial sequence
<220> FEATURE:
<223> OTHER INFORMATION: Polypeptide

<400> SEQUENCE: 79

```
Lys Gln Glu Val Thr Gln Ser Pro Ser Ser Leu Asn Lys Pro Glu Ser
1               5                   10                  15

Glu Asn Val Ser Ile Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Glu Asn Val
65                  70                  75                  80

Gln Pro Asn Asp Ser Gly Thr Tyr Phe Cys Ser Val Arg Pro Thr Ser
                85                  90                  95

Gly Gly Ser Tyr Ile Pro Thr Phe Gly Lys Gly Thr Lys Leu Ser Val
            100                 105                 110

Thr Asn
```

<210> SEQ ID NO 80
<211> LENGTH: 114
<212> TYPE: PRT
<213> ORGANISM: Artificial sequence
<220> FEATURE:
<223> OTHER INFORMATION: Polypeptide

<400> SEQUENCE: 80

```
Lys Gln Glu Val Thr Gln Ser Pro Ser Ser Met Ser Val Pro Glu Ser
1               5                   10                  15

Glu Asn Val Ser Ile Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
```

```
                35                  40                  45
Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Glu Arg Ile
 65                  70                  75                  80

Gln Pro Asn Asp Ser Gly Thr Tyr Phe Cys Ala Val Arg Pro Thr Ser
                 85                  90                  95

Gly Gly Ser Tyr Ile Pro Thr Phe Gly Lys Gly Thr Lys Leu Ser Val
                100                 105                 110

Thr Asn

<210> SEQ ID NO 81
<211> LENGTH: 114
<212> TYPE: PRT
<213> ORGANISM: Artificial sequence
<220> FEATURE:
<223> OTHER INFORMATION: Polypeptide

<400> SEQUENCE: 81

Lys Gln Glu Val Thr Gln Ser Pro Ser Ser Glu Ser Val Pro Glu Ser
 1                   5                  10                  15

Glu Asn Val Ser Ile Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
             35                  40                  45

Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Glu Arg Ile
 65                  70                  75                  80

Gln Pro Asn Asp Ser Gly Thr Tyr Phe Cys Ala Val Arg Pro Thr Ser
                 85                  90                  95

Gly Gly Ser Tyr Ile Pro Thr Phe Gly Lys Gly Thr Lys Leu Ser Val
                100                 105                 110

Thr Asn

<210> SEQ ID NO 82
<211> LENGTH: 114
<212> TYPE: PRT
<213> ORGANISM: Artificial sequence
<220> FEATURE:
<223> OTHER INFORMATION: Polypeptide

<400> SEQUENCE: 82

Lys Gln Glu Val Thr Gln Ser Pro Ser Ser Leu Ser Val Pro Glu Ser
 1                   5                  10                  15

Glu Asn Val Ser Ile Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
             35                  40                  45

Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Glu Arg Ile
 65                  70                  75                  80

Gln Pro Asn Asp Ser Gly Thr Tyr Phe Cys Ala Val Arg Pro Thr Ser
                 85                  90                  95

Gly Gly Ser Tyr Ile Pro Thr Phe Gly Lys Gly Thr Lys Leu Ser Val
                100                 105                 110
```

Thr Asn

<210> SEQ ID NO 83
<211> LENGTH: 114
<212> TYPE: PRT
<213> ORGANISM: Artificial sequence
<220> FEATURE:
<223> OTHER INFORMATION: Polypeptide

<400> SEQUENCE: 83

Lys Gln Glu Val Thr Gln Ser Pro Ser Ser Leu Ser Lys Pro Glu Ser
1               5                   10                  15

Glu Asn Val Ser Ile Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Glu Arg Ile
65                  70                  75                  80

Gln Pro Asn Asp Ser Gly Thr Tyr Phe Cys Ala Val Arg Pro Thr Ser
                85                  90                  95

Gly Gly Ser Tyr Ile Pro Thr Phe Gly Lys Gly Thr Lys Leu Ser Val
            100                 105                 110

Thr Asn

<210> SEQ ID NO 84
<211> LENGTH: 114
<212> TYPE: PRT
<213> ORGANISM: Artificial sequence
<220> FEATURE:
<223> OTHER INFORMATION: Polypeptide

<400> SEQUENCE: 84

Lys Gln Glu Val Thr Gln Ser Pro Ser Ser Leu Asn Val Pro Glu Ser
1               5                   10                  15

Glu Asn Val Ser Ile Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Glu Asn Val
65                  70                  75                  80

Gln Pro Asn Asp Ser Gly Thr Tyr Phe Cys Ser Val Arg Pro Thr Ser
                85                  90                  95

Gly Gly Ser Tyr Ile Pro Thr Phe Gly Lys Gly Thr Lys Leu Ser Val
            100                 105                 110

Thr Asn

<210> SEQ ID NO 85
<211> LENGTH: 114
<212> TYPE: PRT
<213> ORGANISM: Artificial sequence
<220> FEATURE:
<223> OTHER INFORMATION: Polypeptide

<400> SEQUENCE: 85

```
Lys Gln Glu Val Thr Gln Ser Pro Ser Ser Leu Ser Val Pro Glu Ser
1               5                   10                  15

Glu Asn Val Ser Ile Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Glu Arg Ile
65                  70                  75                  80

Gln Pro Asn Asp Ser Gly Thr Tyr Phe Cys Ala Val Arg Pro Thr Ser
                85                  90                  95

Gly Gly Ser Tyr Ile Pro Thr Phe Gly Lys Gly Thr Lys Leu Ser Val
                100                 105                 110

Thr Asn
```

<210> SEQ ID NO 86
<211> LENGTH: 113
<212> TYPE: PRT
<213> ORGANISM: Artificial sequence
<220> FEATURE:
<223> OTHER INFORMATION: Polypeptide

<400> SEQUENCE: 86

```
Asn Ala Gly Ile Thr Gln Thr Pro Lys Tyr Leu Ser Val Lys Thr Gly
1               5                   10                  15

Gln Ser Val Thr Leu Gln Cys Ala Gln Asp Met Asn His Glu Tyr Met
            20                  25                  30

Ser Trp Tyr Arg Gln Asp Pro Gly Gln Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Ile Glu Ser
65                  70                  75                  80

Val Thr Pro Ser Asp Ser Ala Leu Tyr Leu Cys Ala Ser Ser Tyr Val
                85                  90                  95

Gly Asn Thr Gly Glu Leu Phe Phe Gly Pro Gly Thr Arg Leu Glu Val
                100                 105                 110

Asp
```

<210> SEQ ID NO 87
<211> LENGTH: 113
<212> TYPE: PRT
<213> ORGANISM: Artificial sequence
<220> FEATURE:
<223> OTHER INFORMATION: Polypeptide

<400> SEQUENCE: 87

```
Asn Ala Gly Ile Thr Gln Thr Pro Lys Tyr Leu Ser Val Lys Thr Gly
1               5                   10                  15

Gln Ser Val Thr Leu Gln Cys Ala Gln Asp Met Asn His Glu Tyr Met
            20                  25                  30

Ser Trp Tyr Arg Gln Asp Pro Gly Gln Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Ile Glu Ser
```

```
                65                  70                  75                  80

Val Thr Pro Ser Asp Ser Ala Leu Tyr Leu Cys Ala Ser Ser Tyr Val
                    85                  90                  95

Gly Asn Thr Gly Glu Leu Phe Phe Gly Pro Gly Thr Arg Leu Glu Val
                    100                 105                 110

Asp

<210> SEQ ID NO 88
<211> LENGTH: 113
<212> TYPE: PRT
<213> ORGANISM: Artificial sequence
<220> FEATURE:
<223> OTHER INFORMATION: Polypeptide

<400> SEQUENCE: 88

Asn Ala Gly Val Thr Gln Thr Pro Lys Tyr Leu Ser Val Lys Thr Gly
1               5                   10                  15

Gln Ser Val Thr Leu Gln Cys Ala Gln Asp Met Asn His Glu Tyr Met
                    20                  25                  30

Ser Trp Tyr Arg Gln Asp Pro Gly Gln Gly Leu Arg Leu Ile His Tyr
                35                  40                  45

Ser Val Gly Ala Gly Ile Thr Asp Gln Gly Glu Val Pro Asn Gly Tyr
            50                  55                  60

Asn Val Ser Arg Ser Thr Thr Glu Asp Phe Pro Leu Arg Ile Glu Ser
65                  70                  75                  80

Val Thr Pro Ser Asp Ser Ala Leu Tyr Leu Cys Ala Ser Ser Tyr Val
                    85                  90                  95

Gly Asn Thr Gly Glu Leu Phe Phe Gly Pro Gly Thr Arg Leu Glu Val
                    100                 105                 110

Asp

<210> SEQ ID NO 89
<211> LENGTH: 113
<212> TYPE: PRT
<213> ORGANISM: Artificial sequence
<220> FEATURE:
<223> OTHER INFORMATION: Polypeptide

<400> SEQUENCE: 89

Asn Ala Gly Val Thr Gln Thr Pro Lys Tyr Leu Ser Val Lys Thr Gly
1               5                   10                  15

Gln Ser Val Thr Leu Gln Cys Ala Gln Asp Met Asn His Glu Tyr Met
                    20                  25                  30

Ser Trp Tyr Arg Gln Asp Pro Gly Gln Gly Leu Arg Leu Ile His Tyr
                35                  40                  45

Ser Val Gly Ala Gly Ile Thr Asp Gln Gly Glu Val Pro Asn Gly Tyr
            50                  55                  60

Asn Val Ser Arg Ser Thr Thr Glu Asp Phe Pro Leu Arg Ile Glu Ser
65                  70                  75                  80

Val Thr Pro Ser Asp Ser Ala Leu Tyr Leu Cys Ala Ser Ser Tyr Val
                    85                  90                  95

Gly Asn Thr Gly Glu Leu Phe Phe Gly Pro Gly Thr Arg Leu Glu Val
                    100                 105                 110

Asp

<210> SEQ ID NO 90
<211> LENGTH: 113
```

<212> TYPE: PRT
<213> ORGANISM: Artificial sequence
<220> FEATURE:
<223> OTHER INFORMATION: Polypeptide

<400> SEQUENCE: 90

Asn Ala Gly Ile Thr Gln Thr Pro Lys Tyr Leu Ser Val Lys Thr Gly
1               5                   10                  15
Gln Ser Val Thr Leu Gln Cys Ala Gln Asp Met Asn His Glu Tyr Met
            20                  25                  30
Ser Trp Tyr Arg Gln Asp Pro Gly Gln Gly Leu Arg Leu Ile His Tyr
        35                  40                  45
Ser Val Gly Ala Gly Ile Thr Asp Gln Gly Glu Val Pro Asn Gly Tyr
    50                  55                  60
Asn Val Ser Arg Ser Thr Thr Glu Asp Phe Pro Leu Arg Ile Glu Ser
65                  70                  75                  80
Val Thr Pro Ser Asp Ser Ala Leu Tyr Leu Cys Ala Ser Ser Tyr Val
                85                  90                  95
Gly Asn Thr Gly Glu Leu Phe Phe Gly Pro Gly Thr Arg Leu Glu Val
            100                 105                 110
Asp

<210> SEQ ID NO 91
<211> LENGTH: 113
<212> TYPE: PRT
<213> ORGANISM: Artificial sequence
<220> FEATURE:
<223> OTHER INFORMATION: Polypeptide

<400> SEQUENCE: 91

Asn Ala Gly Ile Thr Gln Thr Pro Lys Tyr Val Ser Val Lys Thr Gly
1               5                   10                  15
Gln Ser Val Thr Leu Gln Cys Ala Gln Asp Met Asn His Glu Tyr Met
            20                  25                  30
Ser Trp Tyr Arg Gln Asp Pro Gly Gln Gly Leu Arg Leu Ile His Tyr
        35                  40                  45
Ser Val Gly Ala Gly Ile Thr Asp Gln Gly Glu Val Pro Asn Gly Tyr
    50                  55                  60
Asn Val Ser Arg Ser Thr Thr Glu Asp Phe Pro Leu Arg Ile Glu Ser
65                  70                  75                  80
Val Thr Pro Ser Asp Ser Ala Leu Tyr Leu Cys Ala Ser Ser Tyr Val
                85                  90                  95
Gly Asn Thr Gly Glu Leu Phe Phe Gly Pro Gly Thr Arg Leu Glu Val
            100                 105                 110
Asp

<210> SEQ ID NO 92
<211> LENGTH: 113
<212> TYPE: PRT
<213> ORGANISM: Artificial sequence
<220> FEATURE:
<223> OTHER INFORMATION: Polypeptide

<400> SEQUENCE: 92

Asn Ala Gly Val Thr Gln Thr Pro Lys Tyr Val Ser Val Lys Thr Gly
1               5                   10                  15
Gln Ser Val Thr Leu Gln Cys Ala Gln Asp Met Asn His Glu Tyr Met
            20                  25                  30

Ser Trp Tyr Arg Gln Asp Pro Gly Gln Gly Leu Arg Leu Ile His Tyr
            35                  40                  45

Ser Val Gly Ala Gly Ile Thr Asp Gln Gly Glu Val Pro Asn Gly Tyr
 50                      55                  60

Asn Val Ser Arg Ser Thr Thr Glu Asp Phe Pro Leu Arg Ile Glu Ser
 65                  70                  75                  80

Val Thr Pro Ser Asp Ser Ala Leu Tyr Leu Cys Ala Ser Ser Tyr Val
                85                  90                  95

Gly Asn Thr Gly Glu Leu Phe Phe Gly Pro Gly Thr Arg Leu Glu Val
            100                 105                 110

Asp

<210> SEQ ID NO 93
<211> LENGTH: 113
<212> TYPE: PRT
<213> ORGANISM: Artificial sequence
<220> FEATURE:
<223> OTHER INFORMATION: Polypeptide

<400> SEQUENCE: 93

Asn Ala Gly Val Thr Gln Thr Pro Lys Tyr Val Ser Val Lys Thr Gly
 1               5                  10                  15

Gln Ser Val Thr Leu Gln Cys Ala Gln Asp Met Asn His Glu Tyr Met
            20                  25                  30

Ser Trp Tyr Arg Gln Asp Pro Gly Gln Gly Leu Arg Leu Ile His Tyr
            35                  40                  45

Ser Val Gly Ala Gly Ile Thr Asp Gln Gly Glu Val Pro Asn Gly Tyr
 50                      55                  60

Asn Val Ser Arg Ser Thr Thr Glu Asp Phe Pro Leu Arg Ile Glu Ser
 65                  70                  75                  80

Val Thr Pro Ser Asp Ser Ala Leu Tyr Leu Cys Ala Ser Ser Tyr Val
                85                  90                  95

Gly Asn Thr Gly Glu Leu Phe Phe Gly Pro Gly Thr Arg Leu Glu Val
            100                 105                 110

Asp

<210> SEQ ID NO 94
<211> LENGTH: 113
<212> TYPE: PRT
<213> ORGANISM: Artificial sequence
<220> FEATURE:
<223> OTHER INFORMATION: Polypeptide

<400> SEQUENCE: 94

Asn Ala Gly Ile Thr Gln Thr Pro Lys Tyr Val Ser Val Lys Thr Gly
 1               5                  10                  15

Gln Ser Val Thr Leu Gln Cys Ala Gln Asp Met Asn His Glu Tyr Met
            20                  25                  30

Ser Trp Tyr Arg Gln Asp Pro Gly Gln Gly Leu Arg Leu Ile His Tyr
            35                  40                  45

Ser Val Gly Ala Gly Ile Thr Asp Gln Gly Glu Val Pro Asn Gly Tyr
 50                      55                  60

Asn Val Ser Arg Ser Thr Thr Glu Asp Phe Pro Leu Arg Ile Glu Ser
 65                  70                  75                  80

Val Thr Pro Ser Asp Ser Ala Leu Tyr Leu Cys Ala Ser Ser Tyr Val
                85                  90                  95

Gly Asn Thr Gly Glu Leu Phe Phe Gly Pro Gly Thr Arg Leu Glu Val

Asp

<210> SEQ ID NO 95
<211> LENGTH: 113
<212> TYPE: PRT
<213> ORGANISM: Artificial sequence
<220> FEATURE:
<223> OTHER INFORMATION: Polypeptide

<400> SEQUENCE: 95

Asn Ala Gly Ile Thr Gln Thr Pro Lys Tyr Leu Ser Val Lys Thr Gly
1               5                   10                  15
Gln Ser Val Thr Leu Gln Cys Ala Gln Asp Met Asn His Glu Tyr Met
                20                  25                  30
Ser Trp Tyr Arg Gln Asp Pro Gly Gln Gly Leu Arg Leu Ile His Tyr
            35                  40                  45
Ser Val Gly Ala Gly Ile Thr Asp Gln Gly Glu Val Pro Asn Gly Tyr
        50                  55                  60
Asn Val Ser Arg Ser Thr Thr Glu Asp Phe Pro Leu Arg Ile Glu Ser
65                  70                  75                  80
Val Thr Pro Ser Asp Ser Ala Leu Tyr Leu Cys Ala Ser Ser Tyr Val
                85                  90                  95
Gly Asn Thr Gly Glu Leu Phe Phe Gly Pro Gly Thr Arg Leu Glu Val
            100                 105                 110
Asp

<210> SEQ ID NO 96
<211> LENGTH: 113
<212> TYPE: PRT
<213> ORGANISM: Artificial sequence
<220> FEATURE:
<223> OTHER INFORMATION: Polypeptide

<400> SEQUENCE: 96

Asn Ala Gly Ile Thr Gln Thr Pro Lys Tyr Val Ser Val Lys Thr Gly
1               5                   10                  15
Gln Ser Val Thr Leu Gln Cys Ala Gln Asp Met Asn His Glu Tyr Met
                20                  25                  30
Ser Trp Tyr Arg Gln Asp Pro Gly Gln Gly Leu Arg Leu Ile His Tyr
            35                  40                  45
Ser Val Gly Ala Gly Ile Thr Asp Gln Gly Glu Val Pro Asn Gly Tyr
        50                  55                  60
Asn Val Ser Arg Ser Thr Thr Glu Asp Phe Pro Leu Arg Ile Glu Ser
65                  70                  75                  80
Val Thr Pro Ser Asp Ser Ala Leu Tyr Leu Cys Ala Ser Ser Tyr Val
                85                  90                  95
Gly Asn Thr Gly Glu Leu Phe Phe Gly Pro Gly Thr Arg Leu Glu Val
            100                 105                 110
Asp

<210> SEQ ID NO 97
<211> LENGTH: 114
<212> TYPE: PRT
<213> ORGANISM: Artificial sequence
<220> FEATURE:
<223> OTHER INFORMATION: Polypeptide

<400> SEQUENCE: 97

```
Lys Gln Glu Val Thr Gln Ser Pro Ser Ser Leu Asn Val Pro Glu Ser
1               5                   10                  15

Glu Asn Val Ser Ile Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Glu Arg Ile
65                  70                  75                  80

Gln Pro Asn Asp Ser Gly Thr Tyr Phe Cys Ala Val Arg Pro Thr Ser
                85                  90                  95

Gly Gly Ser Tyr Ile Pro Thr Phe Gly Lys Gly Thr Lys Leu Ser Val
                100                 105                 110

Thr Asn
```

<210> SEQ ID NO 98
<211> LENGTH: 113
<212> TYPE: PRT
<213> ORGANISM: Artificial sequence
<220> FEATURE:
<223> OTHER INFORMATION: Polypeptide

<400> SEQUENCE: 98

```
Asn Ala Gly Ile Thr Gln Thr Pro Lys Tyr Leu Ser Val Lys Thr Gly
1               5                   10                  15

Gln Ser Val Thr Leu Gln Cys Ala Gln Asp Met Asn His Glu Tyr Met
                20                  25                  30

Ser Trp Tyr Arg Gln Asp Pro Gly Gln Gly Leu Arg Leu Ile His Tyr
            35                  40                  45

Ser Val Gly Ala Gly Ile Thr Asp Gln Gly Glu Val Pro Asn Arg Tyr
    50                  55                  60

Asn Val Ser Arg Ser Thr Thr Glu Asp Phe Pro Leu Arg Ile Glu Ser
65                  70                  75                  80

Val Thr Pro Ser Asp Ser Ala Val Tyr Leu Cys Ala Ser Ser Tyr Val
                85                  90                  95

Gly Asn Thr Gly Glu Leu Phe Phe Gly Pro Gly Thr Arg Leu Glu Val
                100                 105                 110

Asp
```

<210> SEQ ID NO 99
<211> LENGTH: 113
<212> TYPE: PRT
<213> ORGANISM: Artificial sequence
<220> FEATURE:
<223> OTHER INFORMATION: Polypeptide

<400> SEQUENCE: 99

```
Asp Ala Lys Thr Thr Gln Pro Asn Ser Met Ser Val Asn Glu Glu Glu
1               5                   10                  15

Pro Val Ser Ile Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
            35                  40                  45

His Gly Leu Thr Ser Asn Val Asn Asn Arg Arg Ala Ser Leu Ala Ile
    50                  55                  60
```

```
Ala Glu Asp Arg Lys Ser Ser Thr Leu Tyr Ile His Arg Ile Thr Pro
 65                  70                  75                  80

Asn Asp Ser Gly Thr Tyr Phe Cys Ala Val Pro Leu Ala Gly Gly Thr
                 85                  90                  95

Ser Tyr Gly Lys Leu Thr Phe Gly Lys Gly Thr Lys Leu Ser Val Thr
                100                 105                 110

Asn

<210> SEQ ID NO 100
<211> LENGTH: 113
<212> TYPE: PRT
<213> ORGANISM: Artificial sequence
<220> FEATURE:
<223> OTHER INFORMATION: Polypeptide

<400> SEQUENCE: 100

Gly Ala Gly Ile Ser Gln Ser Pro Arg Tyr Val Ser Val Lys Arg Gly
 1               5                  10                  15

Gln Asp Val Thr Leu Arg Cys Asp Pro Ile Ser Gly His Val Ser Leu
                20                  25                  30

Phe Trp Tyr Gln Gln Ala Pro Gly Gln Gly Pro Glu Phe Leu Thr Tyr
             35                  40                  45

Phe Gln Asn Glu Ala Gln Leu Asp Lys Ser Gly Leu Pro Ser Asp Arg
 50                  55                  60

Phe Ser Ala Glu Arg Pro Glu Gly Ser Val Ser Thr Leu Lys Ile Gln
 65                  70                  75                  80

Ser Val Thr Pro Ser Asp Ser Ala Leu Tyr Leu Cys Ala Ser Ser Leu
                 85                  90                  95

Gly Gln Ala Tyr Glu Gln Tyr Phe Gly Pro Gly Thr Arg Leu Glu Val
                100                 105                 110

Asp

<210> SEQ ID NO 101
<211> LENGTH: 113
<212> TYPE: PRT
<213> ORGANISM: Artificial sequence
<220> FEATURE:
<223> OTHER INFORMATION: Polypeptide

<400> SEQUENCE: 101

Asp Ala Lys Val Thr Gln Pro Asn Ser Leu Asn Val Asn Glu Glu Glu
 1               5                  10                  15

Pro Val Ser Ile Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
             35                  40                  45

His Gly Leu Thr Ser Asn Val Asn Asn Gly Arg Leu Ser Leu Ala Ile
 50                  55                  60

Ala Glu Asp Arg Lys Ser Ser Thr Leu Tyr Ile Glu Arg Ile Thr Pro
 65                  70                  75                  80

Asn Asp Ser Gly Thr Tyr Phe Cys Ala Val Pro Leu Ala Gly Gly Thr
                 85                  90                  95

Ser Tyr Gly Lys Leu Thr Phe Gly Lys Gly Thr Lys Leu Ser Val Thr
                100                 105                 110

Asn

<210> SEQ ID NO 102
```

<211> LENGTH: 113
<212> TYPE: PRT
<213> ORGANISM: Artificial sequence
<220> FEATURE:
<223> OTHER INFORMATION: Polypeptide

<400> SEQUENCE: 102

Gly Ala Gly Ile Ser Gln Ser Pro Arg Tyr Leu Ser Val Lys Thr Gly
1               5                   10                  15

Gln Asp Val Thr Leu Arg Cys Asp Pro Ile Ser Gly His Val Ser Leu
            20                  25                  30

Phe Trp Tyr Gln Gln Ala Pro Gly Gln Gly Pro Glu Phe Leu Thr Tyr
        35                  40                  45

Phe Gln Asn Glu Ala Gln Leu Asp Lys Ser Gly Leu Pro Ser Asp Arg
    50                  55                  60

Phe Ser Ala Glu Arg Pro Glu Gly Ser Val Ser Thr Leu Lys Ile Gln
65                  70                  75                  80

Ser Val Thr Pro Ser Asp Ser Ala Val Tyr Leu Cys Ala Ser Ser Leu
                85                  90                  95

Gly Gln Ala Tyr Glu Gln Tyr Phe Gly Pro Gly Thr Arg Leu Glu Val
            100                 105                 110

Asp

<210> SEQ ID NO 103
<211> LENGTH: 110
<212> TYPE: PRT
<213> ORGANISM: Artificial sequence
<220> FEATURE:
<223> OTHER INFORMATION: Polypeptide

<400> SEQUENCE: 103

Thr Gln Leu Leu Glu Gln Ser Pro Gln Ser Met Ser Val Gln Glu Ser
1               5                   10                  15

Glu Asn Val Thr Ile Tyr Cys Asn Ser Ser Ser Val Phe Ser Ser Leu
            20                  25                  30

Gln Trp Tyr Arg Gln Glu Pro Gly Glu Gly Pro Thr Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Arg Ile Gln
65                  70                  75                  80

Pro Asn Asp Ser Gly Thr Tyr Phe Cys Ala Val Ala Gly Ser Gln Gly
                85                  90                  95

Asn Leu Ile Phe Gly Lys Gly Thr Lys Leu Ser Val Thr Asn
            100                 105                 110

<210> SEQ ID NO 104
<211> LENGTH: 112
<212> TYPE: PRT
<213> ORGANISM: Artificial sequence
<220> FEATURE:
<223> OTHER INFORMATION: Polypeptide

<400> SEQUENCE: 104

Asp Gly Gly Ile Thr Gln Ser Pro Lys Tyr Val Ser Val Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr

```
                35                  40                  45
Ser Gln Ile Val Asn Asp Phe Gln Lys Gly Asp Ile Ala Glu Gly Tyr
            50                  55                  60

Ser Val Ser Arg Glu Lys Lys Glu Ser Phe Pro Leu Thr Ile Thr Ser
65                  70                  75                  80

Val Thr Lys Ser Asp Ser Ala Leu Tyr Leu Cys Ala Ser Ser Ser Arg
                85                  90                  95

Ser Ser Tyr Glu Gln Tyr Phe Gly Pro Gly Thr Arg Leu Glu Val Asp
            100                 105                 110

<210> SEQ ID NO 105
<211> LENGTH: 110
<212> TYPE: PRT
<213> ORGANISM: Artificial sequence
<220> FEATURE:
<223> OTHER INFORMATION: Polypeptide

<400> SEQUENCE: 105

Thr Gln Leu Val Glu Gln Ser Pro Gln Ser Leu Asn Val Gln Glu Ser
1               5                   10                  15

Glu Asn Val Thr Ile Tyr Cys Asn Ser Ser Val Phe Ser Ser Leu
            20                  25                  30

Gln Trp Tyr Arg Gln Glu Pro Gly Glu Gly Pro Thr Leu Leu Val Thr
            35                  40                  45

Val Val Thr Gly Gly Glu Val Lys Lys Leu Lys Arg Leu Thr Phe Gln
        50                  55                  60

Phe Gly Asp Ala Arg Lys Asp Ser Ser Leu His Ile Glu Arg Ile Gln
65                  70                  75                  80

Pro Asn Asp Ser Gly Thr Tyr Phe Cys Ala Val Ala Gly Ser Gln Gly
                85                  90                  95

Asn Leu Ile Phe Gly Lys Gly Thr Lys Leu Ser Val Thr Asn
            100                 105                 110

<210> SEQ ID NO 106
<211> LENGTH: 112
<212> TYPE: PRT
<213> ORGANISM: Artificial sequence
<220> FEATURE:
<223> OTHER INFORMATION: Polypeptide

<400> SEQUENCE: 106

Asp Gly Gly Ile Thr Gln Ser Pro Lys Tyr Leu Ser Val Lys Thr Gly
1               5                   10                  15

Gln Ser Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
            35                  40                  45

Ser Gln Ile Val Asn Asp Phe Gln Lys Gly Asp Ile Ala Glu Arg Tyr
            50                  55                  60

Ser Val Ser Arg Glu Lys Lys Glu Ser Phe Pro Leu Thr Ile Thr Ser
65                  70                  75                  80

Val Thr Lys Ser Asp Ser Ala Val Tyr Leu Cys Ala Ser Ser Ser Arg
                85                  90                  95

Ser Ser Tyr Glu Gln Tyr Phe Gly Pro Gly Thr Arg Leu Glu Val Asp
            100                 105                 110

<210> SEQ ID NO 107
<211> LENGTH: 114
```

```
<212> TYPE: PRT
<213> ORGANISM: Artificial sequence
<220> FEATURE:
<223> OTHER INFORMATION: Polypeptide

<400> SEQUENCE: 107

Asp Gln Glu Val Thr Gln Ser Pro Ser Ser Leu Asn Val Pro Glu Gly
1               5                   10                  15

Glu Asn Val Ser Ile Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Val Arg Pro Tyr Gln Arg Glu Gln Thr Ser Gly Arg Leu Asn Ala
        50                  55                  60

Ser Leu Asp Lys Ser Ser Gly Arg Ser Thr Leu Tyr Ile Glu Arg Ile
65                  70                  75                  80

Gln Pro Asn Asp Ser Gly Thr Tyr Phe Cys Ala Val Arg Pro Gly Gly
                85                  90                  95

Ala Gly Ser Tyr Gln Leu Thr Phe Gly Lys Gly Thr Lys Leu Ser Val
                100                 105                 110

Thr Asp

<210> SEQ ID NO 108
<211> LENGTH: 112
<212> TYPE: PRT
<213> ORGANISM: Artificial sequence
<220> FEATURE:
<223> OTHER INFORMATION: Polypeptide

<400> SEQUENCE: 108

Lys Ala Gly Ile Thr Gln Thr Pro Arg Tyr Leu Ser Val Lys Thr Gly
1               5                   10                  15

Gln Ser Val Thr Leu Ser Cys Ser Pro Ile Ser Gly His Arg Ser Val
                20                  25                  30

Ser Trp Tyr Gln Gln Thr Pro Gly Gln Gly Leu Gln Phe Leu Phe Glu
            35                  40                  45

Tyr Phe Ser Glu Thr Gln Arg Asn Lys Gly Asn Phe Pro Gly Arg Phe
        50                  55                  60

Ser Gly Arg Gln Phe Ser Asn Ser Arg Ser Glu Leu Asn Ile Glu Ser
65                  70                  75                  80

Val Thr Pro Ser Asp Ser Ala Leu Tyr Leu Cys Ala Ser Ser Pro Asn
                85                  90                  95

Met Ala Asp Glu Gln Tyr Phe Gly Pro Gly Thr Arg Leu Glu Val Asp
                100                 105                 110
```